(12) United States Patent
Baumann et al.

(10) Patent No.: US 7,151,075 B2
(45) Date of Patent: Dec. 19, 2006

(54) 3-(4,5-DIHYDROISOXAZOLE-5-YL) BENZOYLPYRAZOLE

(75) Inventors: Ernst Baumann, Dudenhofen (DE); Wolfgang von Deyn, Neustadt (DE); Steffen Kudis, Mannheim (DE); Klaus Langemann, Worms (DE); Guido Mayer, Neustadt (DE); Ulf Misslitz, Neustadt (DE); Ulf Neidlein, Mannheim (DE); Helmut Walter, Obrigheim (DE); Karl-Otto Westphalen, Speyer (DE); Matthias Witschel, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/168,216

(22) PCT Filed: Dec. 19, 2000

(86) PCT No.: PCT/EP00/12950

§ 371 (c)(1),
(2), (4) Date: Jun. 19, 2002

(87) PCT Pub. No.: WO01/46182

PCT Pub. Date: Jun. 28, 2001

(65) Prior Publication Data

US 2003/0100590 A1    May 29, 2003

(30) Foreign Application Priority Data

Dec. 22, 1999 (DE) ................ 199 62 249
Mar. 7, 2000 (DE) ................ 100 10 551

(51) Int. Cl.
*A01N 43/80* (2006.01)
*C07D 413/10* (2006.01)

(52) U.S. Cl. .................... 504/271; 548/240

(58) Field of Classification Search ........... 548/240; 504/271
See application file for complete search history.

(56) References Cited

U.S. PATENT DOCUMENTS 5,536,698 A * 7/1996 Loher et al. ............ 504/106

5,846,907 A  12/1998  von Deyn
6,165,944 A  12/2000  von Deyn

FOREIGN PATENT DOCUMENTS

| CA | 2278331 | 7/1998 |
|----|---------|--------|
| EP | 509 533 | 10/1992 |
| EP | 891 972 | 1/1999 |
| EP | 900 795 | 3/1999 |
| WO | 99/21852 | 5/1992 |
| WO | 96/26206 | 8/1996 |
| WO | 98/21187 | 5/1998 |
| WO | 98/31681 | 7/1998 |
| WO | 98/31682 | 7/1998 |

OTHER PUBLICATIONS

Abstract WO 9921852-1.

* cited by examiner

Primary Examiner—Kamal A. Saeed
Assistant Examiner—Rebecca Anderson
(74) Attorney, Agent, or Firm—Novak Druce & Quigg LLP

(57) ABSTRACT

The invention relates to 3-(4,5-dihydroisoxazole-5-yl)benzoylpyrazole of the formula (I)

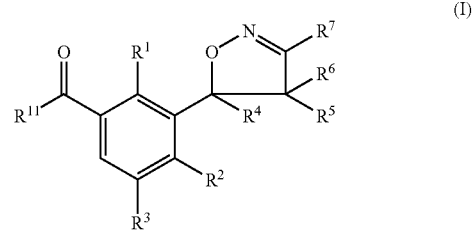

(I)

wherein the variables are as defined herein. The invention also relates to the agriculturally useful salts thereof, to methods and to intermediate products for preparing the 3-(4,5-dihydroisoxazole-5-yl)benzoylpyrazole, to agents containing them and to the use thereof for combating undesired plants.

12 Claims, No Drawings

3-(4,5-DIHYDROISOXAZOLE-5-YL)BENZOYLPYRAZOLE

This application is a 371 of PCT/EP00/12950 filed Dec. 19, 2000.

The present invention relates to 3-(4,5-dihydroisoxazol-5-yl)benzoylpyrazoles of the formula I

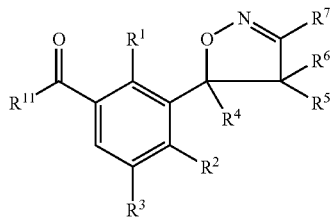

where:

$R^1$, $R^2$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

$R^3$ is hydrogen, halogen or $C_1$–$C_6$-alkyl;

$R^4$ is hydrogen or $C_1$–$C_4$-alkyl;

$R^5$, $R^6$ are hydrogen, halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, di($C_1$–$C_4$-alkyl)aminoimino-$C_1$–$C_4$-alkyl, hydroxyimino-$C_1$–$C_4$-alkyl, $C_1$–$C_6$-alkoxyimino-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, where the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

or $R^5$ and $R^6$ together form a $C_2$–$C_6$-alkanediyl chain which may be mono- to tetrasubstituted by $C_1$–$C_4$-alkyl and/or may be interrupted by oxygen or an unsubstituted or $C_1$–$C_4$-alkyl-substituted nitrogen;

$R^7$ is halogen, cyano, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, amino, $C_1$–$C_6$-alkylamino, di($C_1$–$C_6$-alkyl)amino, di($C_1$–$C_4$-alkoxy)methyl, hydroxyimino-$C_1$–$C_4$-alkyl, $C_1$–$C_6$-alkoxyimino-$C_1$–$C_4$-alkyl or $COR^8$;

$R^8$ is hydrogen, $C_1$–$C_4$-alkyl, $C_1$–$C_4$-haloalkyl, hydroxyl, $C_1$–$C_4$-alkoxy, $C_1$–$C_4$-alkoxy-$C_2$–$C_4$-alkoxy, $C_1$–$C_4$-haloalkoxy, $C_3$–$C_6$-alkenyloxy, $C_3$–$C_6$-alkynyloxy or $NR^9R^{10}$;

$R^9$ is hydrogen or $C_1$–$C_4$-alkyl;

$R^{10}$ is $C_1$–$C_4$-alkyl;

$R^{11}$ is a pyrazole, attached in the 4-position, of the formula II

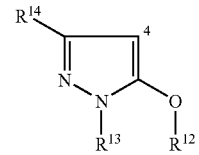

where $R^{12}$ is hydrogen, $C_1$–$C_4$-alkyl, $C_1$–$C_4$-haloalkyl, $C_3$–$C_6$-alkenyl, $C_3$–$C_4$-alkynyl, $C_1$–$C_4$-alkylcarbonyl, $C_1$–$C_4$-haloalkylcarbonyl, $C_1$–$C_4$-alkylsulfonyl, $C_1$–$C_4$-haloalkylsulfonyl, thienylmethyl, phenyl, benzyl, phenylcarbonyl, phenylsulfonyl or phenylcarbonylmethyl, where the phenyl radical of the five last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_1$–$C_6$-alkyl, $C_1$–$C_6$-haloalkyl or $C_3$–$C_6$-cycloalkyl;

$R^{14}$ is hydrogen, $C_1$–$C_6$-alkyl or $C_3$–$C_6$-cycloalkyl;

and their agriculturally useful salts.

Moreover, the invention relates to processes and intermediates for preparing compounds of the formula I, to compositions comprising them and to the use of these derivatives or of the compositions comprising them for controlling harmful plants.

Pyrazol-4-ylbenzoyl derivatives have been disclosed in the literature, for example in WO 96/26206.

However, the herbicidal properties of the prior-art compounds and their compatibility with crop plants are not entirely satisfactory. It is an object of the present invention to provide novel, in particular herbicidally active, compounds which have improved properties.

We have found that this object is achieved by the 3-(4,5-dihydroisoxazol-5-yl)benzoylpyrazoles of the formula I and by their herbicidal activity.

We have furthermore found herbicidal compositions which comprise the compounds I and which have very good herbicidal activity. Moreover, we have found processes for preparing these compositions and methods for controlling undesirable vegetation using the compounds I.

Depending on the substitution pattern, the compounds of the formula I can contain one or more chiral centers, in which case they can exist as enantiomer or diastereomer mixtures. The present invention relates both to the pure enantiomers or diastereomers and to the mixtures thereof.

The compounds of the formula I may also exist in the form of their agriculturally useful salts, the type of salt generally being of no importance. In general, suitable salts are the salts of those cations or the acid addition salts of those acids whose cations, or anions, respectively, do not adversely affect the herbicidal activity of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four hydrogen atoms to be replaced by $C_1$–$C_4$-alkyl or hydroxy-$C_1$–$C_4$-alkyl and/or a phenyl or benzyl, preferably ammonium, diisopropylammonium, tetramethylammonium, tetrabutylammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

The organic moieties mentioned for the substituents $R^1$–$R^{15}$ or as radicals on phenyl rings are collective terms for individual enumerations of the individual group members. All hydrocarbon chains, i.e. all alkyl, haloalkyl, cyanoalkyl, alkenyl, alkynyl, alkoxy, haloalkoxy, alkylthio, haloalkylthio, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkenyloxy, alkynyloxy, alkylamino, dialkylamino, alkoxyalkyl, dialkoxymethyl, dialkoxyalkyl, alkylthioalkyl, dialkylaminoalkyl, dialkylaminoiminoalkyl, hydroxyiminoalkyl, alkoxyiminoalkyl, alkoxycarbonylalkyl and alkoxyalkoxy moieties may be straight-chain or branched. Unless otherwise specified, halogenated substituents preferably carry one to five identical or different halogen atoms. The meaning of halogen is in each case fluorine, chlorine, bromine or iodine.

Examples of other meanings are:

$C_1$–$C_4$-alkyl and the alkyl moieties of $C_1$–$C_4$-alkylcarbonyl, di($C_1$–$C_4$-alkoxy)-$C_1$–$C_4$-alkyl, di($C_1$–$C_4$-alkyl) aminoimino-$C_4$-alkyl, $C_1$–$C_6$-alkoxyimino-$C_1$–$C_4$-alkyl and hydroxyimino-$C_1$–$C_4$-alkyl: for example methyl, ethyl, propyl, 1-methylethyl, butyl, 1-methylpropyl, 2-methylpropyl and 1,1-dimethylethyl;

$C_1$–$C_6$-alkyl: $C_1$–$C_4$-alkyl as mentioned above and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl and the haloalkyl moieties of $C_1$–$C_4$-haloalkylcarbonyl: a $C_1$–$C_4$-alkyl radical as mentioned above which is partially or fully substituted by fluorine, chlorine, bromine and/or iodine, i.e., for example chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 1-fluoroethyl, 1-chloroethyl, 1-bromomethyl, 1-iodoethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl: $C_1$–$C_4$-haloalkyl as mentioned above and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-cyanoalkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl;

$C_3$–$C_4$-alkenyl: for example prop-1-en-1-yl, prop-2-en-1-yl, 1-methylethen-1-yl, buten-1-yl, buten-2-yl, buten-3-yl, 1-methylprop-1-en-1-yl, 2-methylprop-1-en-1-yl, 1-methylprop-2-en-1-yl or 2-methylprop-2-en-1-yl;

$C_3$–$C_4$-alkynyl: for example prop-1-yn-1-yl, prop-2-yn-1-yl, but-1-yn-1-yl, but-1-yn-3-yl, but-1-yn-4-yl or but-2-yn-1-yl;

$C_1$–$C_4$-alkoxy and the alkoxy moieties of di($C_1$–$C_4$-alkoxy)methyl and di($C_1$–$C_4$-alkoxy)-$C_1$–$C_4$-alkyl: for example methoxy, ethoxy, propoxy, 1-methylethoxy, butoxy, 1-methylpropoxy, 2-methylpropoxy and 1,1-dimethylethoxy;

$C_1$–$C_6$-alkoxy and the alkoxy moieties of $C_1$–$C_6$-alkoxyimino-$C_1$–$C_4$-alkyl: $C_1$–$C_4$-alkoxy as mentioned above and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_6$-haloalkoxy: $C_1$–$C_4$-haloalkoxy as mentioned above and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$–$C_4$-alkylthio: for example methylthio, ethylthio, propylthio, 1-methylethylthio, butylthio, 1-methylpropylthio, 2-methylpropylthio and 1,1-dimethylethylthio;

$C_1$–$C_6$-alkylthio: $C_1$–$C_4$-alkylthio as mentioned above and, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$–$C_4$-haloalkylthio: a $C_1$–$C_4$-alkylthio radical as mentioned above, which is partially or fully substituted by fluorine, chlorine, bromine and/or iodine, i.e., for example fluoromethylthio, difluoromethylthio, trifluoromethylthio, chlorodifluoromethylthio, bromodifluoromethylthio, 2-fluorethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_6$-haloalkylthio: $C_1$–$C_4$-haloalkylthio as mentioned above and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$–$C_6$-haloalkylsulfinyl: a $C_1$–$C_6$-alkylsulfinyl radical as mentioned above which is partially or fully substituted by fluorine, chlorine, bromine and/or iodine, i.e., for example fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$–$C_4$-alkylsulfonyl ($C_1$–$C_4$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, and also for example pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_4$-haloalkylsulfonyl: a $C_1$–$C_4$-alkylsulfonyl radical as mentioned above which is partially or fully substituted by fluorine, chlorine, bromine and/or iodine, i.e., for example fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl and nonafluorobutylsulfonyl;

$C_1$–$C_6$-haloalkylsulfonyl: a $C_1$–$C_4$-haloalkylsulfonyl radical as mentioned above, and also 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl and 1,1-dimethoxycarbonyl;

$C_1$–$C_4$-haloalkoxycarbonyl: a $C_1$–$C_4$-alkoxycarbonyl radical as mentioned above which is partially or fully substituted by fluorine, chlorine, bromine and/or iodine, i.e., for example fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl and 4-iodobutoxycarbonyl;

$C_3$–$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy and 1-ethyl-2-methylprop-2-en-1-yloxy;

$C_3$–$C_6$-alkynyloxy: for example prop-1-yn-1-yloxy, prop-2-yn-1-yloxy, but-1-yn-1-yloxy, but-1-yn-3-yloxy, but-1-yn-4-yloxy, but-2-yn-1-yloxy, pent-1-yn-1-yloxy, pent-1-yn-3-yloxy, pent-1-yn-4-yloxy, pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, hex-1-yn-1-yloxy, hex-1-yn-3-yloxy, hex-1-yn-4-yloxy, hex-1-yn-5-yloxy, hex-1-yn-6-yloxy, hex-2-yn-1-yloxy, hex-2-yn-4-yloxy, hex-2-yn-5-yloxy, hex-2-yn-6-yloxy, hex-3-yn-1-yloxy, hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy and 4-methylpent-2-yn-5-yloxy;

$C_1$–$C_6$-alkylamino: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$–$C_4$-alkyl)amino and the dialkylamino moieties of di($C_1$–$C_4$-alkyl)aminoimino-$C_1$–$C_4$-alkyl: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di($C_1$–$C_6$-alkyl)amino: di($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

di($C_1$–$C_4$-alkyl)amino-$C_1$–$C_4$-alkyl: $C_1$–$C_4$-alkyl which is substituted by di($C_1$–$C_4$-alkyl)amino as mentioned above, i.e., for example N,N-dimethylaminomethyl, N,N-diethylaminomethyl, N,N-dipropylaminomethyl, N,N-di(1-methylethyl)aminomethyl, N,N-dibutylaminomethyl, N,N-di(1-methylpropyl)aminomethyl, N,N-di(2-methylpropyl)aminomethyl, N,N-di(1,1-dimethylethyl)aminomethyl, N-ethyl-N-methylaminomethyl, N-methyl-N-propylaminomethyl, N-methyl-N-(1-methylethyl)aminomethyl, N-butyl-N-methylaminomethyl, N-methyl-N-(1-methylpropyl)aminomethyl, N-methyl-N-(2-methylpropyl)aminomethyl, N-(1,1-dimethylethyl)-N-methylaminomethyl, N-ethyl-N-propylaminomethyl, N-ethyl-N-(1-methylethyl)aminomethyl, N-butyl-N-ethylaminomethyl, N-ethyl-N-(1-methylpropyl)aminomethyl, N-ethyl-N-(2-methylpropyl)aminomethyl, N-ethyl-N-(1,1-dimethylethyl)aminomethyl, N-(1-methylethyl)-N-propylaminomethyl, N-butyl-N-propylaminomethyl, N-(1-methylpropyl)-N-propylaminomethyl, N-(2-methylpropyl)-N-propylaminomethyl, N-(1,1-dimethylethyl)-N-propylaminomethyl, N-butyl-N-(1-methylethyl)aminomethyl, N-(1-methylethyl)-N-(1-methylpropyl)aminomethyl, N-(1-methylethyl)-N-(2-methylpropyl)aminomethyl, N-(1,1-dimethylethyl)-N-(1-methylethyl)aminomethyl, N-butyl-N-(1-methylpropyl)aminomethyl, N-butyl-N-(2-methylpropyl)aminomethyl, N-butyl-N-(1,1-dimethylethyl)aminomethyl, N-(1-methylpropyl)-N-(2-methylpropyl)aminomethyl, N-(1,1-dimethylethyl)-N-(1-methylpropyl)aminomethyl, N-(1,1-dimethylethyl)-N-(2-methylpropyl)aminomethyl, 2-(N,N-dimethylamino)ethyl, 2-(N,N-diethylamino)ethyl, 2-(N,N-dipropylamino)ethyl, 2-[N,N-di(1-methylethyl)amino]ethyl, 2-[N,N-dibutylamino]ethyl, 2-[N,N-di(1-methylpropyl)amino]ethyl, 2-[N,N-di(2-methylpropyl)amino]ethyl, 2-[N,N-di(1,1-dimethylethyl)amino]ethyl, 2-[N-ethyl-N-methylamino]ethyl, 2-[N-methyl-N-propylamino]ethyl, 2-[N-methyl-N-(1-methylethyl)amino]ethyl, 2-[N-butyl-N-methylamino]ethyl, 2-[N-methyl-N-(1-methylpropyl)amino]ethyl, 2-[N-methyl-N-(2-methylpropyl)amino]ethyl, 2-[N-(1,1-dimethylethyl)-N-methylamino]ethyl, 2-[N-ethyl-N-propylamino]ethyl, 2-[N-ethyl-N-(1-methylethyl)amino]ethyl, 2-[N-butyl-N-ethylamino]ethyl, 2-[N-ethyl-N-(1-methylpropyl)amino]ethyl, 2-[N-ethyl-N-(2-methylpropyl)amino]ethyl, 2-[N-ethyl-N-(1,1-dimethylethylamino]ethyl, 2-[N-(1-methylethyl)-N-propylamino]ethyl, 2-[N-butyl-N-propylamino]ethyl, 2-[N-(1-methylpropyl)-N-propylamino]ethyl, 2-[N-(2-methylpropyl)-N-propylamino]ethyl, 2-[N-(1,1-dimethylethyl)-N-propylamino]ethyl, 2-[N-butyl-N-(1-methylethyl)amino]ethyl, 2-[N-(1-methylethyl)-N-(1-methylpropyl)amino]ethyl, 2-[N-(1-methylethyl)-N-(2-methylpropyl)amino]ethyl, 2-[N-(1,1-dimethylethyl)-N-(1-methylethyl)amino]ethyl, 2-[N-butyl-N-(1-methylpropyl)amino]ethyl, 2-[N-butyl-N-(2-methylpropyl)amino]ethyl, 2-[N-butyl-N-(1,1-dimethylethyl)amino]ethyl, 2-[N-(1-methylpropyl)-N-(2-methylpropyl)amino]ethyl, 2-[N-(1,1-dimethylethyl)-N-(1-methylpropyl)amino]ethyl, 2-[N-(1,1-dimethylethyl)-N-(2-methylpropyl)amino]ethyl, 3-(N,N-dimethylamino)propyl, 3-(N,N-diethylamino)propyl, 4-(N,N-dimethylamino)butyl and 4-(N,N-diethylamino)butyl;

$C_1$–$C_4$-alkoxy-$C_1$–$C_4$-alkyl: $C_1$–$C_4$-alkyl which is substituted by $C_1$–$C_4$-alkoxy as mentioned above, i.e., for example methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl and 4-(1,1-dimethylethoxy)butyl;

$C_1$–$C_4$-alkylthio-$C_1$–$C_4$-alkyl: $C_1$–$C_4$-alkyl which is substituted by $C_1$–$C_4$-alkylthio as mentioned above, i.e., for example methylthiomethyl, ethylthiomethyl, propylthiomethyl, (1-methylethylthio)methyl, butylthiomethyl, (1-methylpropylthio)methyl, (2-methylpropylthio)methyl, (1,1-dimethylethylthio)methyl, 2-methylthioethyl, 2-ethylthioethyl, 2-(propylthio)ethyl, 2-(1-methylethylthio)ethyl, 2-(butylthio)ethyl, 2-(1-methylpropylthio)ethyl, 2-(2-methylpropylthio)ethyl, 2-(1,1-dimethylethylthio)ethyl, 2-(methylthio)propyl, 3-(methylthio)propyl, 2-(ethylthio)propyl, 3-(ethylthio)propyl, 3-(propylthio)propyl, 3-(butylthio)propyl, 4-(methylthio)butyl, 4-(ethylthio)butyl, 4-(propylthio)butyl and 4-(butylthio)butyl;

$C_1$–$C_4$-alkoxycarbonyl-$C_1$–$C_4$-alkyl: $C_1$–$C_4$-alkyl which is substituted by $C_1$–$C_4$-alkoxycarbonyl as mentioned above, i.e., for example methoxycarbonylmethyl, ethoxycarbonylmethyl, propoxycarbonylmethyl, (1-methylethoxycarbonyl)methyl, butoxycarbonylmethyl, (1-methylpropoxycarbonyl)methyl, (2-methylpropoxycarbonyl)methyl, (1,1-dimethylethoxycarbonyl)methyl, 2-(methoxycarbonyl)ethyl, 2-(ethoxycarbonyl)ethyl, 2-(propoxycarbonyl)ethyl, 2-(1-methylethoxycarbonyl)ethyl, 2-(butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(propoxycarbonyl)propyl, 2-(1-methylethoxycarbonyl)propyl, 2-(butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(propoxycarbonyl)propyl, 3-(1-methylethoxycarbonyl)propyl, 3-(butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(propoxycarbonyl)butyl, 2-(1-methylethoxycarbonyl)butyl, 2-(butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(propoxycarbonyl)butyl, 3-(1-methylethoxycarbonyl)butyl, 3-(butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(propoxycarbonyl)butyl, 4-(1-methylethoxycarbonyl)butyl, 4-(butoxycarbonyl)butyl, 4-(1-methylpropoxy)butoxy, 4-(2-methylpropoxy)butoxy and 4-(1,1-dimethylethoxycarbonyl)butyl;

$C_1$–$C_4$-alkoxy-$C_2$–$C_4$-alkoxy: $C_2$–$C_4$-alkoxy which is substituted by $C_1$–$C_4$-alkoxy as mentioned above, i.e., for example 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy) propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy) propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)-butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy and 4-(1,1-dimethylethoxy)butoxy;

$C_2$–$C_6$-alkanediyl: for example ethane-1,2-diyl, propane-1,3-diyl, butane-1,4-diyl, pentane-1,5-diyl and hexane-1,6-diyl;

$C_3$–$C_6$-cycloalkyl: for example cyclopropyl, cyclobutyl, cyclopentyl or cyclohexyl;

$C_3$–$C_8$-cycloalkyl: $C_3$–$C_6$-cycloalkyl as mentioned above, and also cycloheptyl and cyclooctyl.

All phenyl rings are preferably unsubstituted or have attached to them one to three halogen atoms and/or a nitro group, a cyano radical and/or one or two methyl, trifluoromethyl, methoxy or trifluoromethoxy substituents.

With a view to the use of the compounds of the formula I according to the invention as herbicides, the variables preferably have the following meanings, in each case alone or in combination:

$R^1$, $R^2$ are nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl; particularly preferably nitro, halogen, such as, for example, chlorine and bromine, $C_1$–$C_6$-alkyl, such as, for example, methyl and ethyl, $C_1$–$C_6$-alkoxy, such as, for example, methoxy and ethoxy, $C_1$–$C_6$-haloalkyl, such as, for example, difluoromethyl and trifluoromethyl, $C_1$–$C_6$-alkylthio, such as, for example, methylthio and ethylthio, $C_1$–$C_6$-alkylsulfinyl, such as, for example, methylsulfinyl and ethylsulfinyl, $C_1$–$C_6$-alkylsulfonyl, such as, for example, methylsulfonyl, ethylsulfonyl and propylsulfonyl, or $C_1$–$C_6$-haloalkylsulfonyl, such as, for example, trifluoromethylsulfonyl and pentafluoroethylsulfonyl;

$R^3$ is hydrogen;

$R^4$ is hydrogen;

$R^5$, $R^6$ are hydrogen, halogen, cyano, nitro, $C_1$–$C_4$-alkyl, $C_1$–$C_4$-alkoxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, where the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

or $R^5$ and $R^6$ together form a $C_2$–$C_6$-alkanediyl chain which may be mono- to tetrasubstituted by $C_1$–$C_4$-alkyl and/or may be interrupted by oxygen or an unsubstituted or $C_1$–$C_4$-alkyl-substituted nitrogen;

$R^5$ is particularly preferably hydrogen, halogen, cyano, nitro, $C_1$–$C_4$-alkyl, $C_1$–$C_4$-alkoxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, where the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

$R^6$ is particularly preferably hydrogen or $C_1$–$C_4$-alkyl;

very particularly preferably, $R^5$ is hydrogen, $C_1$–$C_4$-alkyl, $C_1$–$C_4$-haloalkyl, $C_1$–$C_4$-alkoxycarbonyl or $CONR^9R^{10}$;

very particularly preferably, $R^6$ is hydrogen or $C_1$–$C_4$-alkyl;

most preferably, $R^5$ is hydrogen or $C_1$–$C_4$-alkyl, in particular hydrogen;

most preferably, $R^6$ is hydrogen;

$R^7$ is halogen, $C_1$–$C_6$-alkyl, $C_1$–$C_6$-haloalkyl, $C_1$–$C_6$-alkoxy, $C_1$–$C_6$-alkylthio, $C_1$–$C_6$-alkylsulfinyl, $C_1$–$C_6$-alkylsulfonyl, amino, $C_1$–$C_6$-alkylamino, di($C_1$–$C_6$-alkyl)amino, di($C_1$–$C_4$-alkoxy)methyl or $COR^8$;

particularly preferably $C_1$–$C_4$-alkyl, such as, for example, methyl, ethyl, 1-methylethyl or 1,1-dimethylethyl, hydroxycarbonyl or $C_1$–$C_4$-alkoxycarbonyl, such as, for example, methoxycarbonyl or ethoxycarbonyl;

$R^8$ is $C_1$–$C_4$-alkyl, hydroxyl, $C_1$–$C_4$-alkoxy or $NR^9R^{10}$;

$R^9$ is hydrogen or $C_1$–$C_4$-alkyl;

$R^{10}$ is $C_1$–$C_4$-alkyl;

$R^{12}$ is hydrogen, $C_1$–$C_4$-alkyl, $C_1$–$C_4$-haloalkyl, $C_1$–$C_4$-alkylcarbonyl, $C_1$–$C_4$-haloalkylcarbonyl, $C_1$–$C_4$-alkylsulfonyl, $C_1$–$C_4$-haloalkylsulfonyl, phenyl, benzyl, phenylcarbonyl or phenylcarbonyl [sic] or phenylsulfonyl, where the phenyl radical of the five last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

is particularly preferably hydrogen, $C_1$–$C_4$-alkyl, $C_1$–$C_4$-alkylsulfonyl, $C_1$–$C_4$-haloalkylsulfonyl, phenyl, benzyl or phenylsulfonyl, where the phenyl radical of the three last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

is very particularly preferably hydrogen or $C_1$–$C_4$-alkylsulfonyl, $C_1$–$C_4$-haloalkylsulfonyl or phenylsulfonyl, where the phenyl radical may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

is likewise particularly preferably hydrogen, $C_1$–$C_4$-alkyl, $C_1$–$C_4$-alkylsulfonyl, $C_1$–$C_4$-haloalkylsulfonyl, thienylmethyl, phenyl, benzyl, phenylsulfonyl or phenylcarbonylmethyl, where the phenyl radical of the four last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_1$–$C_6$-alkyl or $C_3$–$C_6$-cycloalkyl;
particularly preferably methyl, ethyl, 1-methylethyl, 1,1-dimethylethyl or cyclopropyl;

$R^{14}$ is hydrogen or $C_1$–$C_6$-alkyl;
particularly preferably hydrogen or methyl.

The following embodiments of the 3-(4,5-dihydroisoxazol-5-yl)benzoylpyrazoles of the formula I are to be emphasized:

1. In a preferred embodiment of the 3-(4,5-dihydroisoxazol-5-yl)benzoylpyrazoles of the formula I, $R^1$ is nitro, halogen, $C_1$–$C_6$-alkyl, $C_1$–$C_6$-haloalkyl, $C_1$–$C_6$-alkoxy or $C_1$–$C_6$-haloalkoxy;
particularly preferably nitrogen, halogen, such as chlorine or bromine, $C_1$–$C_4$-alkyl, such as methyl or ethyl, $C_1$–$C_4$-haloalkyl, such as difluoromethyl or trifluoromethyl, $C_1$–$C_4$-alkoxy, such as methoxy or ethoxy, or $C_1$–$C_4$-haloalkoxy such as difluoromethoxy or trifluoromethoxy;
particularly preferably halogen, such as chlorine or bromine, $C_1$–$C_4$-alkyl, such as methyl or ethyl or $C_1$–$C_4$-alkoxy, such as methoxy or ethoxy;
most preferably halogen, such as chlorine or bromine, $C_1$–$C_4$-alkyl, such as methyl or ethyl;

$R^2$ is halogen, $C_1$–$C_6$-haloalkyl, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;
particularly preferably halogen, such as fluorine or chlorine, $C_1$–$C_4$-haloalkyl, such as difluoromethyl or trifluoromethyl, or $C_1$–$C_4$-alkylsulfonyl, such as methylsulfonyl or ethylsulfonyl;
very particularly preferably halogen, such as fluorine or chlorine, or $C_1$–$C_4$-alkylsulfonyl, such as methylsulfonyl or ethylsulfonyl.

2. In a further preferred embodiment of the 3-(4,5-dihydroisoxazol-5-yl)benzoylpyrazoles of the formula I,
$R^3$ is hydrogen.

3. In a further preferred embodiment of the 3-(4,5-dihydroisoxazol-5-yl)benzoylpyrazoles of the formula I,
$R^3$ is halogen or $C_1$–$C_4$-alkyl;
particularly preferably chlorine or methyl.

4. In a further [lacuna] embodiment of the 3-(4,5-dihydroisoxazol-5-yl)benzoylpyrazoles of the formula I,
$R^4$ is hydrogen;
$R^5$ is hydrogen, halogen, cyano, nitro, $C_1$–$C_4$-alkyl, $C_1$–$C_4$-alkoxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $C_1$–$C_4$-alkylcarbonyl, $C_1$–$C_4$-alkoxycarbonyl, CONR$^9$R$^{10}$, phenyl or benzyl, where the two last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy;
is particularly preferably hydrogen, $C_1$–$C_4$-alkyl, $C_1$–$C_4$-haloalkyl, $C_1$–$C_4$-alkoxycarbonyl or CONR$^9$R$^{10}$;
very particularly preferably hydrogen or $C_1$–$C_4$-alkyl, such as methyl or ethyl;
most preferably hydrogen;

$R^6$ is hydrogen or $C_1$–$C_4$-alkyl, such as methyl or ethyl;
particularly preferably hydrogen.

5. In a further preferred embodiment of the 3-(4,5-dihydroisoxazol-5-yl)benzoylpyrazoles of the formula I, $R^7$ is halogen, $C_1$–$C_6$-alkyl, $C_1$–$C_6$-haloalkyl, $C_1$–$C_6$-alkoxy, $C_1$–$C_6$-alkylthio, $C_1$–$C_6$-alkylsulfinyl, $C_1$–$C_6$-alkylsulfonyl, amino, $C_1$–$C_6$-alkylamino, di($C_1$–$C_6$-alkyl)amino, di($C_1$–$C_6$-alkoxy)methyl, formyl, $C_1$–$C_4$-alkylcarbonyl, $C_1$–$C_4$-haloalkylcarbonyl, hydroxycarbonyl, $C_1$–$C_4$-alkoxycarbonyl, $C_1$–$C_4$-haloalkoxycarbonyl or CONR$^9$R$^{10}$;
particularly preferably halogen, such as chlorine or bromine, $C_1$–$C_4$-alkyl, such as methyl, ethyl, 1-methylethyl or 1,1-dimethylethyl, $C_1$–$C_4$-alkoxy, such as methoxy or ethoxy, $C_1$–$C_4$-alkylthio, such as methylthio or ethylthio, $C_1$–$C_4$-alkylsulfinyl, such as methylsulfinyl or ethylsulfinyl, $C_1$–$C_4$-alkylsulfonyl, such as methylsulfonyl or ethylsulfonyl, amino, $C_1$–$C_4$-alkylamino, such as methylamino or ethylamino, di($C_1$–$C_4$-alkyl)amino, such as dimethylamino or diethylamino, di($C_1$–$C_4$-alkoxy)methyl, such as dimethoxymethyl or diethoxymethyl, $C_1$–$C_4$-alkylcarbonyl, such as methylcarbonyl or ethylcarbonyl, hydroxycarbonyl, $C_1$–$C_4$-alkoxycarbonyl, such as methoxycarbonyl or ethoxycarbonyl, or CONR$^9$R$^{10}$;
very particularly preferably $C_1$–$C_4$-alkyl, such as methyl, ethyl, 1-methylethyl or 1,1-dimethylethyl, hydroxycarbonyl or $C_1$–$C_4$-alkoxycarbonyl, such as methoxycarbonyl or ethoxycarbonyl;
most preferably $C_1$–$C_4$-alkyl, such as methyl, ethyl, 1-methylethyl or 1,1-dimethylethyl;

6. In a further preferred embodiment of the 3-(4,5-dihydroisoxazol-5-yl)benzoylpyrazoles of the formula I, $R^{12}$ is $C_1$–$C_4$-alkyl, $C_1$–$C_4$-haloalkyl, $C_1$–$C_4$-alkylcarbonyl, $C_1$–$C_4$-haloalkylcarbonyl, $C_1$–$C_4$-alkylsulfonyl, $C_1$–$C_4$-haloalkylsulfonyl, phenyl, benzyl, phenylcarbonyl or phenylsulfonyl, where the phenyl radical of the four last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy;
is particularly preferably $C_1$–$C_4$-alkyl, $C_1$–$C_4$-alkylsulfonyl, $C_1$–$C_4$-haloalkylsulfonyl, phenyl, benzyl or phenylsulfonyl, where the phenyl radical of the three last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy;
is very particularly preferably $C_1$–$C_4$-alkylsulfonyl, $C_1$–$C_4$-haloalkylsulfonyl or phenylsulfonyl, where the phenyl radical may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy;
is likewise particularly preferably benzyl, where the phenyl radical may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

7. In a further preferred embodiment of the 3-(4,5-dihydroisoxazol-5-yl)benzoylpyrazoles of the formula I, $R^{12}$ is $C_1$–$C_4$-alkyl, $C_3$–$C_4$-alkynyl, thienylmethyl, benzyl, phenylcarbonyl, phenylsulfonyl or phenylcarbonylmethyl, where the phenyl radical of the four last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

is particularly preferably thienylmethyl, such as 3-thienylmethyl, benzyl, phenylcarbonyl, phenylsulfonyl or phenylcarbonylmethyl, where the phenyl radical of the four last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy.

8. In a further preferred embodiment of the 3-(4,5-dihydroisoxazol-5-yl)benzoylpyrazoles of the formula I, $R^{12}$ is hydroxyl.

9. In a further preferred embodiment of the 3-(4,5-dihydroisoxazol-5-yl)benzoylpyrazoles of the formula I, $R^{13}$ is $C_1$–$C_4$-alkyl, such as methyl, ethyl, methylethyl or 1,1-dimethylethyl, or $C_3$–$C_6$-cycloalkyl, such as cyclopropyl;

particularly preferably $C_1$–$C_4$-alkyl, such as methyl, ethyl, 1-methylethyl or 1,1-dimethylethyl;

likewise preferably $C_3$–$C_6$-cycloalkyl, such as cyclopropyl;

$R^{14}$ is hydrogen or $C_1$–$C_4$-alkyl, such as, for example, methyl or ethyl;

particularly preferably hydrogen or methyl.

10. In a further preferred embodiment of the 3-(4,5-dihydroisoxazol-5-yl)benzoylpyrazoles of the formula I, $R^1$ is halogen $C_1$–$C_4$-alkyl or $C_1$–$C_4$-alkoxy;

$R^2$ is halogen or $C_1$–$C_4$-alkylsulfonyl;

$R^3$, $R^4$ and $R^6$ are hydrogen;

$R^5$ is hydrogen or $C_1$–$C_4$-alkyl; in particular hydrogen $R^7$ is $C_1$–$C_4$-alkyl, di($C_1$–$C_4$-alkoxy)methyl, hydroxycarbonyl or $C_1$–$C_4$-alkoxycarbonyl;

$R^{12}$ is hydrogen, $C_3$–$C_4$-alkynyl, thienylmethyl, benzyl, phenylcarbonyl, phenylsulfonyl or phenylcarbonylmethyl, where the phenyl radical of the four last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_1$–$C_4$-alkyl, $C_1$–$C_4$-haloalkyl or cyclopropyl;

in particular $C_1$–$C_4$-alkyl or cyclopropyl;

$R^{14}$ is hydrogen, $C_1$–$C_4$-alkyl or cyclopropyl;

in particular hydrogen or $C_1$–$C_4$-alkyl.

Most particular preference is given to the 3-(4,5-dihydroisoxazol-5-yl)benzoylpyrazoles of the formula Ia1 (≡I where $R^1$=Cl; $R^2$=SO$_2$CH$_3$; $R^3$, $R^4$, $R^{12}$, $R^{14}$=H; $R^{13}$=CH$_3$), in particular to the compounds Ia1.1 to Ia1.64, where the radical definitions $R^1$ to $R^{14}$ are of particular importance for the compounds according to the invention, not only in combination with one another but in each case also on their own.

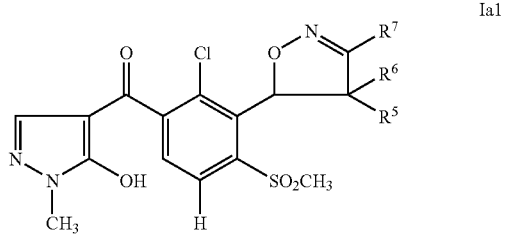

Ia1

TABLE 1

| No. | $R^5$ | $R^6$ | $R^7$ |
|---|---|---|---|
| Ia1.1 | H | H | CH$_3$ |
| Ia1.2 | Cl | H | CH$_3$ |
| Ia1.3 | Br | H | CH$_3$ |
| Ia1.4 | CN | H | CH$_3$ |
| Ia1.5 | NO$_2$ | H | CH$_3$ |
| Ia1.6 | CH$_3$ | H | CH$_3$ |
| Ia1.7 | CH$_2$CH$_3$ | H | CH$_3$ |
| Ia1.8 | CH(CH$_3$)$_2$ | H | CH$_3$ |
| Ia1.9 | C(CH$_3$)3 | H | CH$_3$ |
| Ia1.10 | CHO | H | CH$_3$ |
| Ia1.11 | CH=NOH | H | CH$_3$ |
| Ia1.12 | CH=NOCH$_3$ | H | CH$_3$ |
| Ia1.13 | CH=NOCH$_2$CH$_3$ | H | CH$_3$ |
| Ia1.14 | COCH$_3$ | H | CH$_3$ |
| Ia1.15 | C(=NOH)CH$_3$ | H | CH$_3$ |
| Ia1.16 | C(=NOCH$_3$)CH$_3$ | H | CH$_3$ |
| Ia1.17 | C(=NOCH$_2$CH$_3$)CH$_3$ | H | CH$_3$ |
| Ia1.18 | CH=NN(CH$_3$)$_2$ | H | CH$_3$ |
| Ia1.19 | C[=NN(CH$_3$)$_2$]CH$_3$ | H | CH$_3$ |
| Ia1.20 | COOH | H | CH$_3$ |
| Ia1.21 | COOCH$_3$ | H | CH$_3$ |
| Ia1.22 | COOCH$_2$CH$_3$ | H | CH$_3$ |
| Ia1.23 | OCH$_3$ | H | CH$_3$ |
| Ia1.24 | OCH$_2$CH$_3$ | H | CH$_3$ |
| Ia1.25 | SCH$_3$ | H | CH$_3$ |
| Ia1.26 | CH$_2$F | H | CH$_3$ |
| Ia1.27 | CHF$_2$ | H | CH$_3$ |
| Ia1.28 | CF$_3$ | H | CH$_3$ |
| Ia1.29 | CF$_2$CF$_3$ | H | CH$_3$ |
| Ia1.30 | CH$_2$Cl | H | CH$_3$ |
| Ia1.31 | CH$_2$CN | H | CH$_3$ |
| Ia1.32 | CH$_2$—CH$_2$ | | CH$_3$ |
| Ia1.33 | CH$_2$—CH$_2$—CH$_2$ | | CH$_3$ |
| Ia1.34 | CH$_2$—CH$_2$—CH$_2$—CH$_2$ | | CH$_3$ |
| Ia1.35 | CH$_2$—CH$_2$—CH$_2$—CH$_2$—CH$_2$ | | CH$_3$ |
| Ia1.36 | CH$_3$ | CH$_3$ | CH$_3$ |
| Ia1.37 | CH$_3$ | CH$_2$CH$_3$ | CH$_3$ |
| Ia1.38 | CF$_3$ | COCH$_3$ | CH$_3$ |
| Ia1.39 | CF$_3$ | COOCH$_3$ | CH$_3$ |
| Ia1.40 | CN | COCH$_3$ | CH$_3$ |
| Ia1.41 | CN | COOCH$_3$ | CH$_3$ |
| Ia1.42 | CN | CN | CH$_3$ |
| Ia1.43 | COCH$_3$ | COCH$_3$ | CH$_3$ |
| Ia1.44 | COCH$_3$ | COOCH$_3$ | CH$_3$ |
| Ia1.45 | H | H | CH$_2$CH$_3$ |
| Ia1.46 | H | H | CH(CH$_3$)$_2$ |
| Ia1.47 | H | H | C(CH$_3$)$_3$ |
| Ia1.48 | H | H | Cl |
| Ia1.49 | H | H | OCH$_3$ |
| Ia1.50 | H | H | SCH$_3$ |
| Ia1.51 | H | H | SOCH$_3$ |
| Ia1.52 | H | H | SO$_2$CH$_3$ |
| Ia1.53 | H | H | CN |
| Ia1.54 | H | H | CHO |
| Ia1.55 | H | H | CH=NOH |
| Ia1.56 | H | H | CH=NOCH$_3$ |

TABLE 1-continued

| No. | $R^5$ | $R^6$ | $R^7$ |
|---|---|---|---|
| Ia1.57 | H | H | CH=NOCH$_2$CH$_3$ |
| Ia1.58 | H | H | COCH$_3$ |
| Ia1.59 | H | H | C(=NOH)CH$_3$ |
| Ia1.60 | H | H | C(=NOCH$_3$)CH$_3$ |
| Ia1.61 | H | H | COOH |
| Ia1.62 | H | H | COOCH$_3$ |
| Ia1.63 | H | H | COOCH$_2$CH$_3$ |
| Ia1.64 | H | H | CH(OCH$_2$CH$_3$)$_2$ |

Particular preference is likewise given to the compounds Ia2, in particular to the compounds Ia2.1–Ia2.64 which differ from compounds Ia1.1–Ia1.64 in that $R^{13}$ is ethyl.

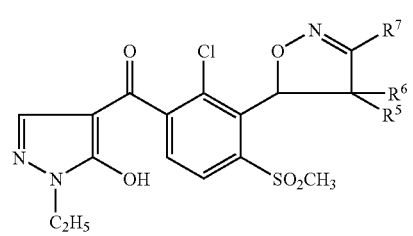

Ia2

Particular preference is likewise given to the compounds Ia3, in particular to the compounds Ia3.1–Ia3.64 which differ from compounds Ia1.1–Ia1.64 in that $R^{13}$ is isopropyl.

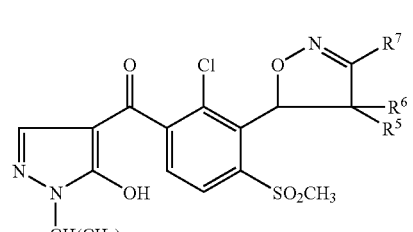

Ia3

Particular preference is likewise given to the compounds Ia4, in particular to the compounds Ia4.1–Ia4.64 which differ from compounds Ia1.1–Ia1.64 in that $R^{13}$ is tert-butyl.

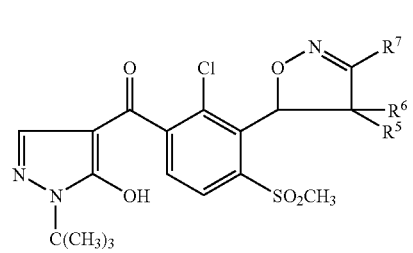

Ia4

Particular preference is likewise given to the compounds Ia5, in particular to the compounds Ia5.1–Ia5.64 which differ from compounds Ia1.1–Ia1.64 in that $R^{14}$ is methyl.

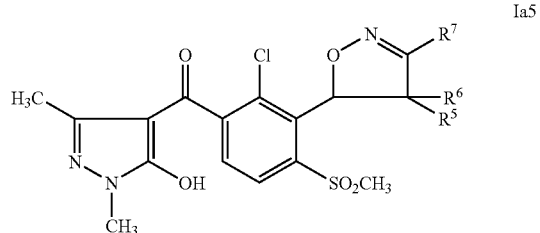

Ia5

Particular preference is likewise given to the compounds Ia6, in particular to the compounds Ia6.1–Ia6.64 which differ from compounds Ia1.1–Ia1.64 in that $R^{13}$ is ethyl and $R^{14}$ is methyl.

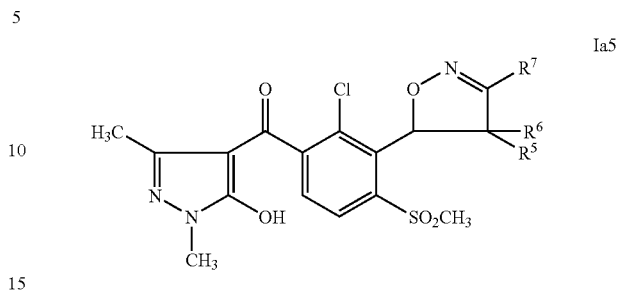

Ia6

Particular preference is likewise given to the compounds Ia7, in particular to the compounds Ia7.1–Ia7.64 which differ from compounds Ia1.1–Ia1.64 in that $R^{13}$ is isopropyl and $R^{14}$ is methyl.

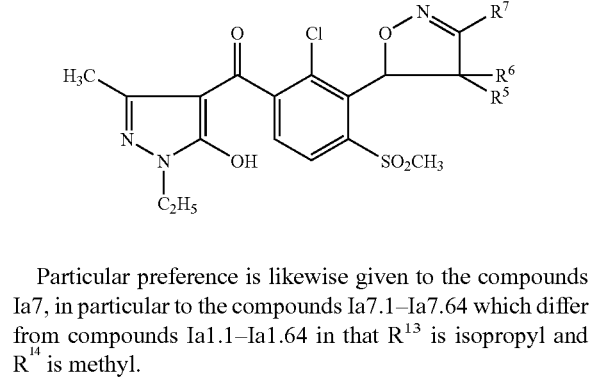

Ia7

Particular preference is likewise given to the compounds Ia8, in particular to the compounds Ia8.1–Ia8.64 which differ from compounds Ia1.1–Ia1.64 in that $R^{13}$ is tert-butyl and $R^{14}$ is methyl.

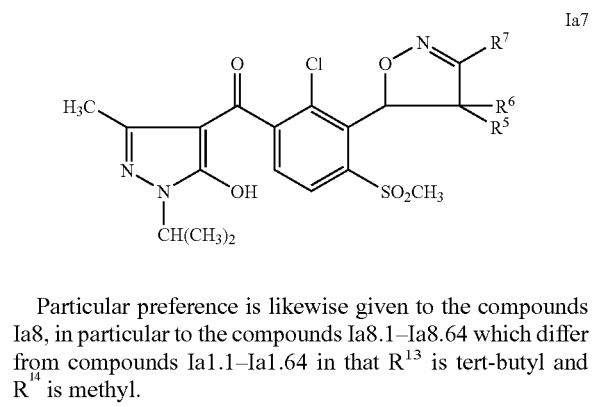

Ia8

Particular preference is likewise given to the compounds Ia9, in particular to the compounds Ia9.1–Ia9.64 which differ from compounds Ia1.1–Ia1.64 in that $R^1$ is methyl.

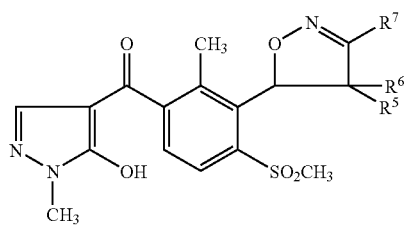

Ia9

Particular preference is likewise given to the compounds Ia10, in particular to the compounds Ia10.1–Ia10.64 which differ from compounds Ia1.1–Ia1.64 in that $R^1$ is methyl and $R^{13}$ is ethyl.

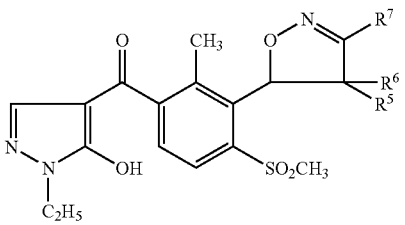

Ia10

Particular preference is likewise given to the compounds Ia11, in particular to the compounds Ia11.1–Ia11.64 which differ from compounds Ia1.1–Ia1.64 in that $R^1$ is methyl and $R^{13}$ is isopropyl.

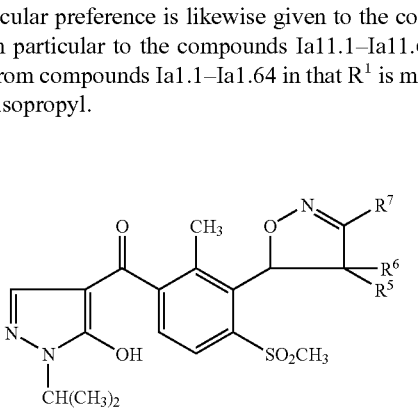

Ia11

Particular preference is likewise given to the compounds Ia12, in particular to the compounds Ia12.1–Ia12.64 which differ from compounds Ia1.1–Ia1.64 in that $R^1$ is methyl and $R^{13}$ is tert-butyl.

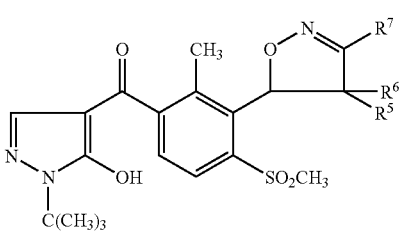

Ia12

Particular preference is likewise given to the compounds Ia13, in particular to the compounds Ia13.1–Ia13.64 which differ from compounds Ia1.1–Ia1.64 in that $R^1$ and $R^{14}$ are methyl.

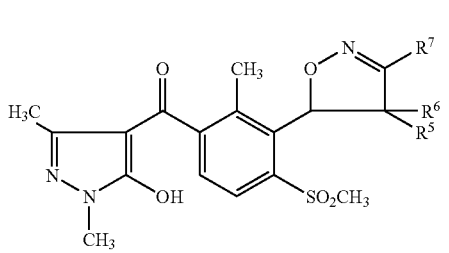

Ia13

Particular preference is likewise given to the compounds Ia14, in particular to the compounds Ia14.1–Ia14.64 which differ from compounds Ia1.1–Ia1.64 in that $R^1$ and $R^{14}$ are methyl and $R^{13}$ is ethyl.

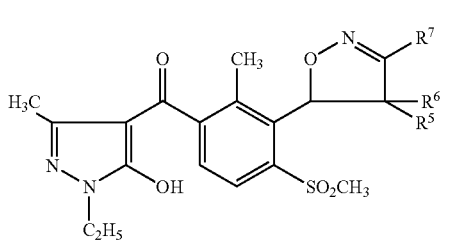

Ia14

Particular preference is likewise given to the compounds Ia15, in particular to the compounds Ia15.1–Ia15.64 which differ from compounds Ia1.1–Ia1.64 in that $R^1$ and $R^{14}$ are methyl and $R^{13}$ is isopropyl.

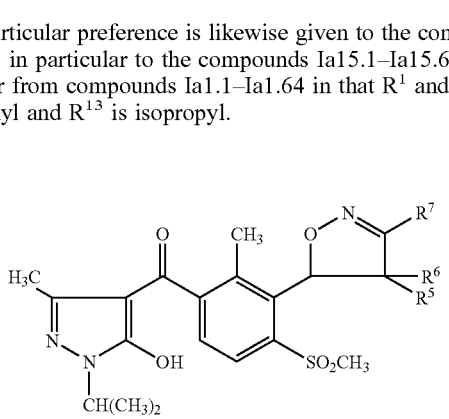

Ia15

Particular preference is likewise given to the compounds Ia16, in particular to the compounds Ia16.1–Ia16.64 which differ from compounds Ia1.1–Ia1.64 in that $R^1$ and $R^{14}$ are methyl and $R^{13}$ is tert-butyl.

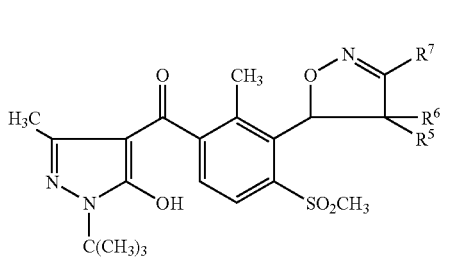

Ia16

Particular preference is likewise given to the compounds Ia17, in particular to the compounds Ia17.1–Ia17.64 which differ from compounds Ia1.1–Ia1.64 in that $R^1$ is trifluoromethyl.

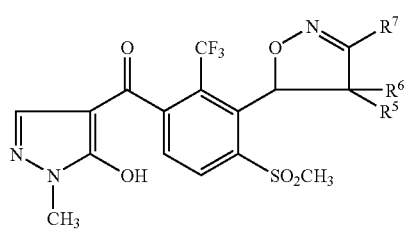

Ia17

Particular preference is likewise given to the compounds Ia18, in particular to the compounds Ia18.1–Ia18.64 which differ from compounds Ia1.1–Ia1.64 in that $R^1$ is trifluoromethyl and $R^{13}$ is ethyl.

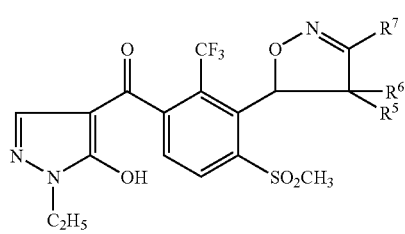

Ia18

Particular preference is likewise given to the compounds Ia19, in particular to the compounds Ia19.1–Ia19.64 which differ from compounds Ia1.1–Ia1.64 in that $R^1$ is trifluoromethyl and $R^{13}$ is isopropyl.

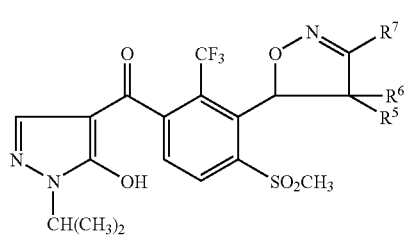

Ia19

Particular preference is likewise given to the compounds Ia20, in particular to the compounds Ia20.1–Ia20.64 which differ from compounds Ia1.1–Ia1.64 in that $R^1$ is trifluoromethyl and $R^{13}$ is tert-butyl.

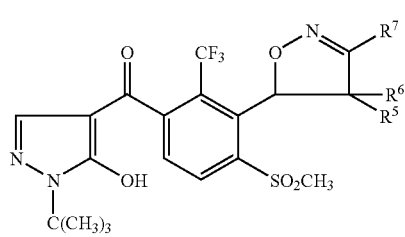

Ia20

Particular preference is likewise given to the compounds Ia21, in particular to the compounds Ia21.1–Ia21.64 which differ from compounds Ia1.1–Ia1.64 in that $R^1$ is trifluoromethyl and $R^{14}$ is methyl.

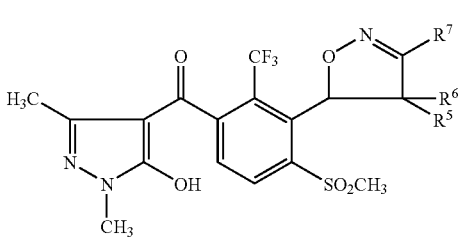

Ia21

Particular preference is likewise given to the compounds Ia22, in particular to the compounds Ia22.1–Ia22.64 which differ from compounds Ia1.1–Ia1.64 in that $R^1$ is trifluoromethyl, $R^{13}$ is ethyl and $R^{14}$ is methyl.

Ia22

Particular preference is likewise given to the compounds Ia23, in particular to the compounds Ia23.1–Ia23.64 which differ from compounds Ia1.1–Ia1.64 in that $R^1$ is trifluoromethyl, $R^{13}$ is isopropyl and $R^{14}$ is methyl.

Ia23

Particular preference is likewise given to the compounds Ia24, in particular to the compounds Ia24.1–Ia24.64 which differ from compounds Ia1.1–Ia1.64 in that $R^1$ is trifluoromethyl, $R^{13}$ is tert-butyl and $R^{14}$ is methyl.

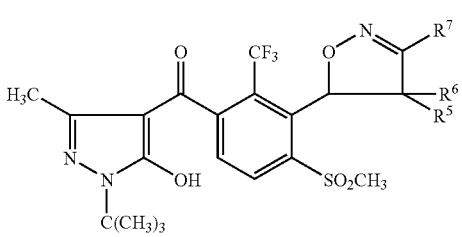

Ia24

Particular preference is likewise given to the compounds Ia25, in particular to the compounds Ia25.1–Ia25.64 which differ from compounds Ia1.1–Ia1.64 in that $R^1$ is methoxy.

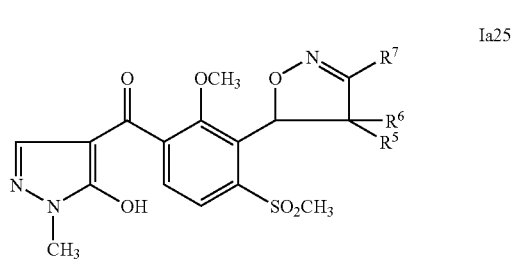
Ia25

Particular preference is likewise given to the compounds Ia26, in particular to the compounds Ia26.1–Ia26.64 which differ from compounds Ia1.1–Ia1.64 in that $R^1$ is methoxy and $R^{13}$ is ethyl.

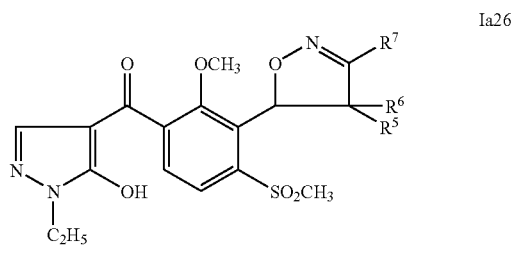
Ia26

Particular preference is likewise given to the compounds Ia27, in particular to the compounds Ia27.1–Ia27.64 which differ from compounds Ia1.1–Ia1.64 in that $R^1$ is methoxy and $R^{13}$ is isopropyl.

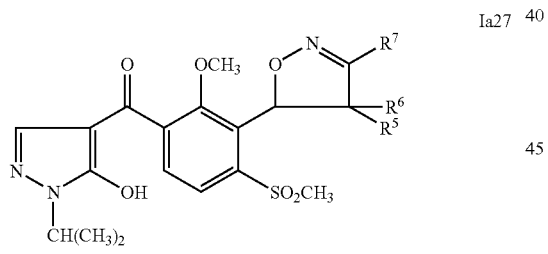
Ia27

Particular preference is likewise given to the compounds Ia28, in particular to the compounds Ia28.1–Ia28.64 which differ from compounds Ia1.1–Ia1.64 in that $R^1$ is methoxy and $R^{13}$ is tert-butyl.

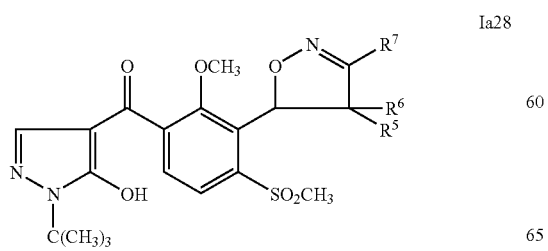
Ia28

Particular preference is likewise given to the compounds Ia29, in particular to the compounds Ia29.1–Ia29.64 which differ from compounds Ia1.1–Ia1.64 in that $R^1$ is methoxy and $R^{14}$ is methyl.

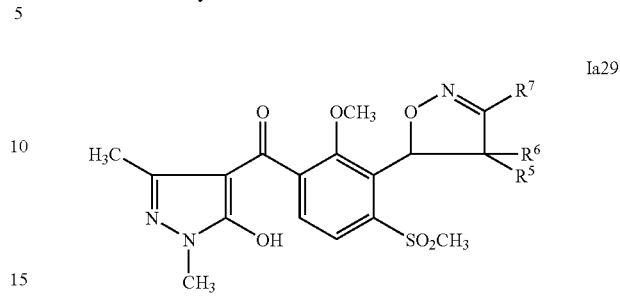
Ia29

Particular preference is likewise given to the compounds Ia30, in particular to the compounds Ia30.1–Ia30.64 which differ from compounds Ia1.1–Ia1.64 in that $R^1$ is methoxy, $R^{13}$ is ethyl and $R^{14}$ is methyl.

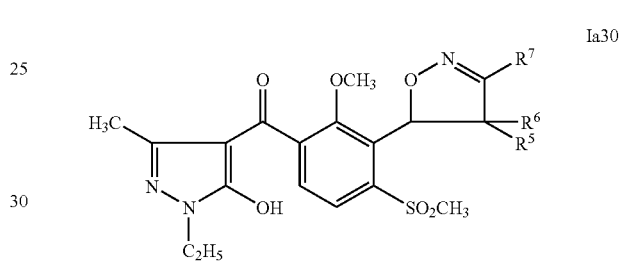
Ia30

Particular preference is likewise given to the compounds Ia31, in particular to the compounds Ia31.1–Ia31.64 which differ from compounds Ia1.1–Ia1.64 in that $R^1$ is methoxy, $R^{13}$ is isopropyl and $R^{14}$ is methyl.

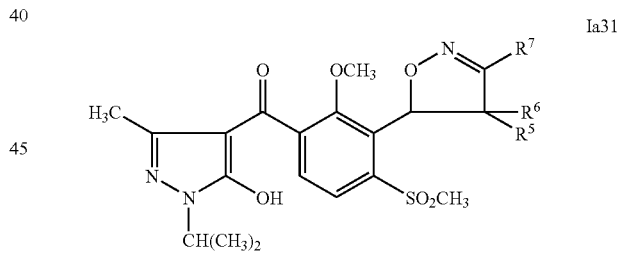
Ia31

Particular preference is likewise given to the compounds Ia32, in particular to the compounds Ia32.1–Ia32.64 which differ from compounds Ia1.1–Ia1.64 in that $R^1$ is methoxy, $R^{13}$ is tert-butyl and $R^{14}$ is methyl.

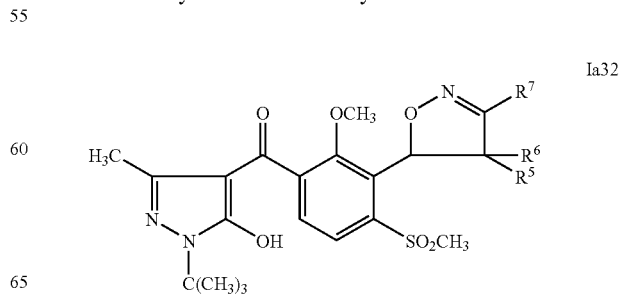
Ia32

Particular preference is likewise given to the compounds Ia33, in particular to the compounds Ia33.1–Ia33.64 which differ from compounds Ia1.1–Ia1.64 in that $R^2$ is ethylsulfonyl.

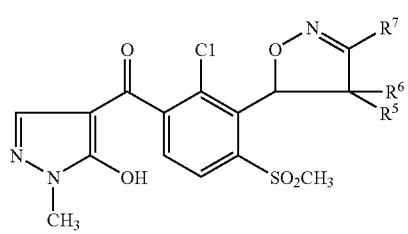

Ia33

Particular preference is likewise given to the compounds Ia34, in particular to the compounds Ia34.1–Ia34.64 which differ from compounds Ia1.1–Ia1.64 in that $R^2$ is ethylsulfonyl and $R^{13}$ is ethyl.

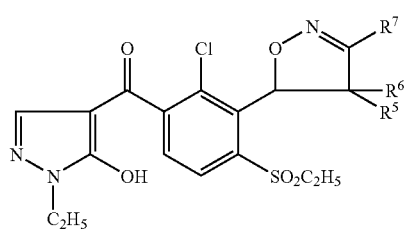

Ia34

Particular preference is likewise given to the compounds Ia35, in particular to the compounds Ia35.1–Ia35.64 which differ from compounds Ia1.1–Ia1.64 in that $R^2$ is ethylsulfonyl and $R^{13}$ is ethyl.

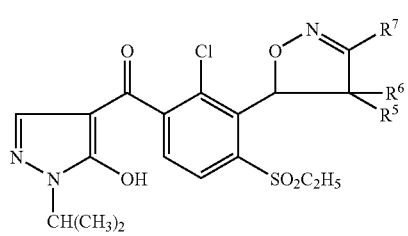

Ia35

Particular preference is likewise given to the compounds Ia36, in particular to the compounds Ia36.1–Ia36.64 which differ from compounds Ia1.1–Ia1.64 in that $R^2$ is ethylsulfonyl and $R^{13}$ is tert-butyl.

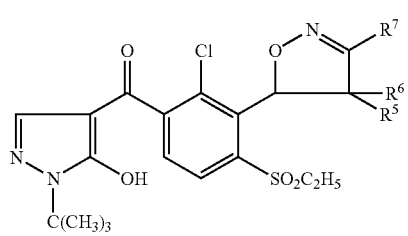

Ia36

Particular preference is likewise given to the compounds Ia37, in particular to the compounds Ia37.1–Ia37.64 which differ from compounds Ia1.1–Ia1.64 in that $R^2$ is ethylsulfonyl and $R^{14}$ is ethyl.

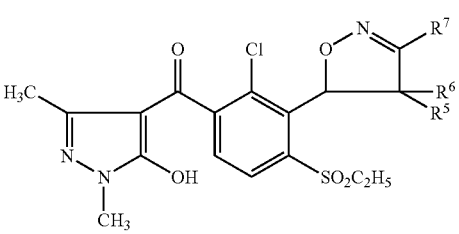

Ia37

Particular preference is likewise given to the compounds Ia38, in particular to the compounds Ia38.1–Ia38.64 which differ from compounds Ia1.1–Ia1.64 in that $R^2$ is ethylsulfonyl, $R^{13}$ is ethyl and $R^{14}$ is methyl.

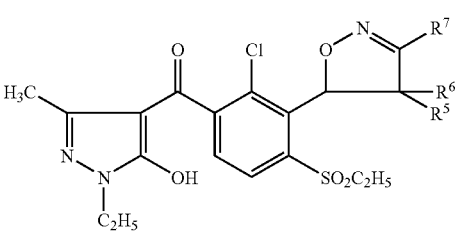

Ia38

Particular preference is likewise given to the compounds Ia39, in particular to the compounds Ia39.1–Ia39.64 which differ from compounds Ia1.1–Ia1.64 in that $R^2$ is ethylsulfonyl, $R^{13}$ is isopropyl and $R^{14}$ is methyl.

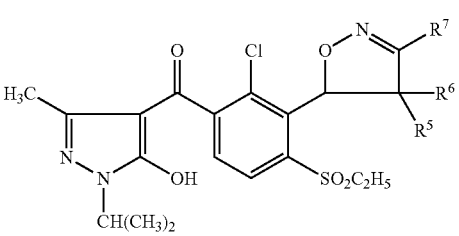

Ia39

Particular preference is likewise given to the compounds Ia40, in particular to the compounds Ia40.1–Ia40.64 which differ from compounds Ia1.1–Ia1.64 in that $R^2$ is ethylsulfonyl, $R^{13}$ is tert-butyl and $R^{14}$ is methyl.

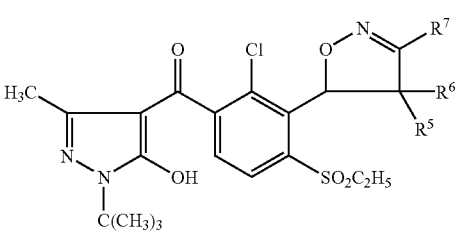

Ia40

Particular preference is likewise given to the compounds Ia41, in particular to the compounds Ia41.1–Ia41.64 which differ from compounds Ia1.1–Ia1.64 in that $R^1$ is methyl and $R^2$ is ethylsulfonyl.

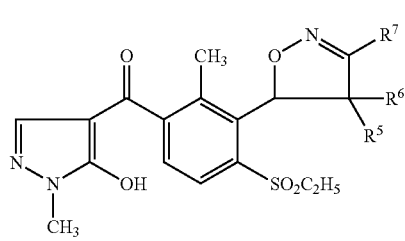

Ia41

Particular preference is likewise given to the compounds Ia42, in particular to the compounds Ia42.1–Ia42.64 which differ from compounds Ia1.1–Ia1.64 in that $R^1$ is methyl, $R^2$ is ethylsulfonyl and $R^{13}$ is ethyl.

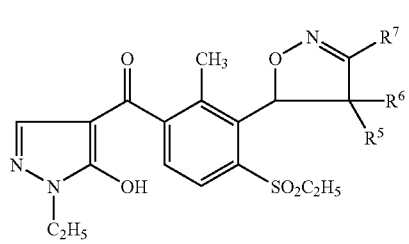

Ia42

Particular preference is likewise given to the compounds Ia43, in particular to the compounds Ia43.1–Ia43.64 which differ from compounds Ia1.1–Ia1.64 in that $R^1$ is methyl, $R^2$ is ethylsulfonyl and $R^{13}$ is isopropyl.

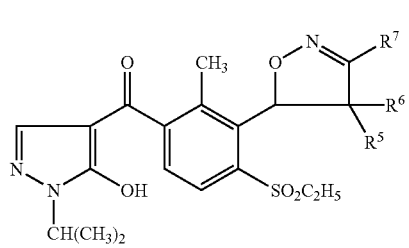

Ia43

Particular preference is likewise given to the compounds Ia44, in particular to the compounds Ia44.1–Ia44.64 which differ from compounds Ia1.1–Ia1.64 in that $R^1$ is methyl, $R^2$ is ethylsulfonyl and $R^{13}$ is tert-butyl.

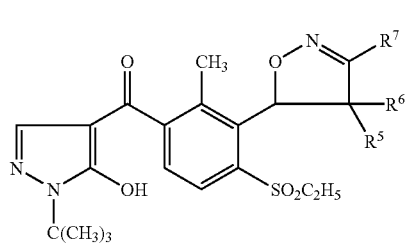

Ia44

Particular preference is likewise given to the compounds Ia45, in particular to the compounds Ia45.1–Ia45.64 which differ from compounds Ia1.1–Ia1.64 in that $R^1$ and $R^{14}$ are methyl and $R^2$ is ethylsulfonyl.

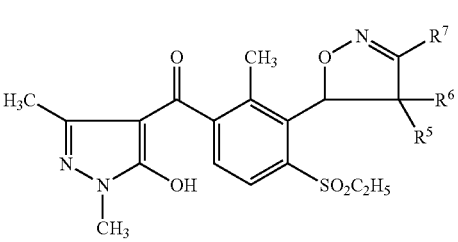

Ia45

Particular preference is likewise given to the compounds Ia46, in particular to the compounds Ia46.1–Ia46.64 which differ from compounds Ia1.1–Ia1.64 in that $R^1$ and $R^{14}$ are methyl, $R^2$ is ethylsulfonyl and $R^{13}$ is ethyl.

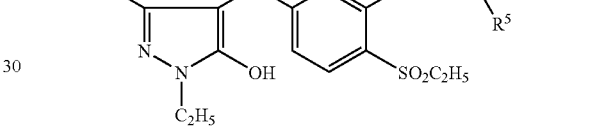

Ia46

Particular preference is likewise given to the compounds Ia47, in particular to the compounds Ia47.1–Ia47.64 which differ from compounds Ia1.1–Ia1.64 in that $R^1$ and $R^{14}$ are methyl, $R^2$ is ethylsulfonyl and $R^{13}$ is isopropyl.

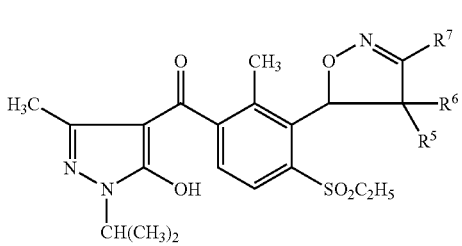

Ia47

Particular preference is likewise given to the compounds Ia48, in particular to the compounds Ia48.1–Ia48.64 which differ from compounds Ia1.1–Ia1.64 in that $R^1$ and $R^{14}$ are methyl, $R^2$ is ethylsulfonyl and $R^{13}$ is tert-butyl.

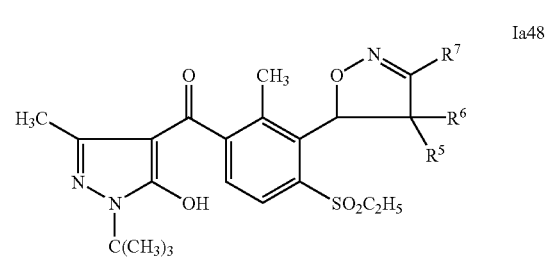

Ia48

Particular preference is likewise given to the compounds Ia49, in particular to the compounds Ia49.1–Ia49.64 which differ from compounds Ia1.1–Ia1.64 in that $R^1$ is trifluoromethyl and $R^2$ is ethylsulfonyl.

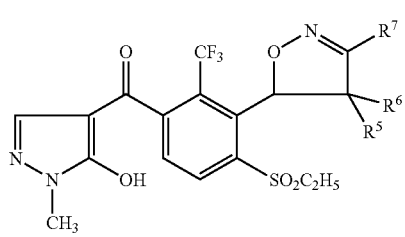

Ia49

Particular preference is likewise given to the compounds Ia50, in particular to the compounds Ia50.1–Ia50.64 which differ from compounds Ia1.1–Ia1.64 in that $R^1$ is trifluoromethyl, $R^2$ is ethylsulfonyl and $R^{13}$ is ethyl.

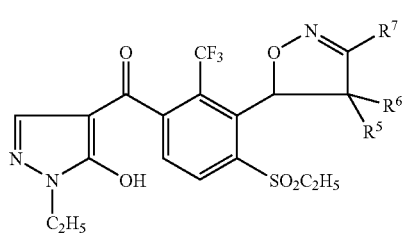

Ia50

Particular preference is likewise given to the compounds Ia51, in particular to the compounds Ia51.1–Ia51.64 which differ from compounds Ia1.1–Ia1.64 in that $R^1$ is trifluoromethyl, $R^2$ is ethylsulfonyl and $R^{13}$ is isopropyl.

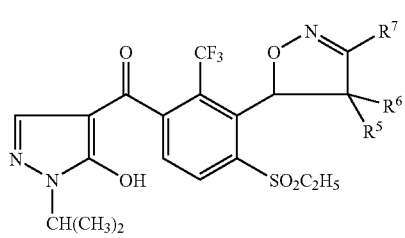

Ia51

Particular preference is likewise given to the compounds Ia52, in particular to the compounds Ia52.1–Ia52.64 which differ from compounds Ia1.1–Ia1.64 in that $R^1$ is trifluoromethyl, $R^2$ is ethylsulfonyl and $R^{13}$ is tert-butyl.

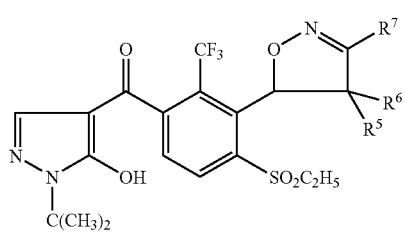

Ia52

Particular preference is likewise given to the compounds Ia53, in particular to the compounds Ia53.1–Ia53.64 which differ from compounds Ia1.1–Ia1.64 in that $R^1$ is trifluoromethyl, $R^2$ is ethylsulfonyl and $R^{14}$ is methyl.

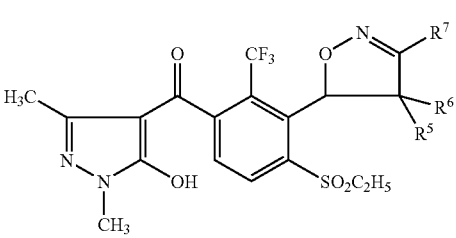

Ia53

Particular preference is likewise given to the compounds Ia54, in particular to the compounds Ia54.1–Ia54.64 which differ from compounds Ia1.1–Ia1.64 in that $R^1$ is trifluoromethyl, $R^2$ is ethylsulfonyl, $R^{13}$ is ethyl and $R^{14}$ is methyl.

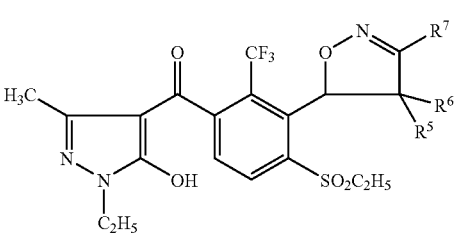

Ia54

Particular preference is likewise given to the compounds Ia55, in particular to the compounds Ia55.1–Ia55.64 which differ from compounds Ia1.1–Ia1.64 in that $R^1$ is trifluoromethyl, $R^2$ is ethylsulfonyl, $R^{13}$ is isopropyl and $R^{14}$ is methyl.

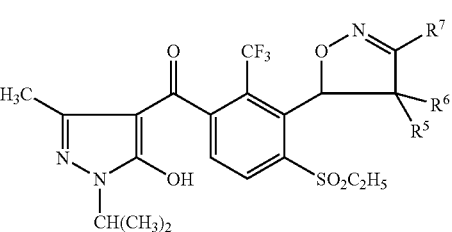

Ia55

Particular preference is likewise given to the compounds Ia56, in particular to the compounds Ia56.1–Ia56.64 which differ from compounds Ia1.1–Ia1.64 in that $R^1$ is trifluoromethyl, $R^2$ is ethylsulfonyl, $R^{13}$ is tert-butyl and $R^{14}$ is methyl.

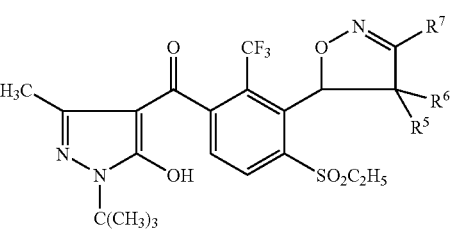

Ia56

Particular preference is likewise given to the compounds Ia57, in particular to the compounds Ia57.1–Ia57.64 which differ from compounds Ia1.1–Ia1.64 in that $R^1$ is methoxy and $R^2$ is ethylsulfonyl.

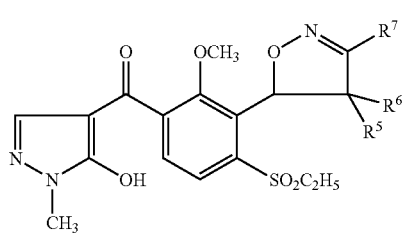

Ia57

Particular preference is likewise given to the compounds Ia58, in particular to the compounds Ia58.1–Ia58.64 which differ from compounds Ia1.1–Ia1.64 in that $R^1$ is methoxy, $R^2$ is ethylsulfonyl and $R^{13}$ is ethyl.

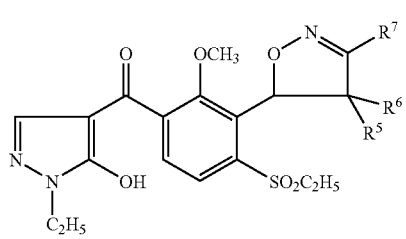

Ia58

Particular preference is likewise given to the compounds Ia59, in particular to the compounds Ia59.1–Ia59.64 which differ from compounds Ia1.1–Ia1.64 in that $R^1$ is methoxy, $R^2$ is ethylsulfonyl and $R^{13}$ is isopropyl.

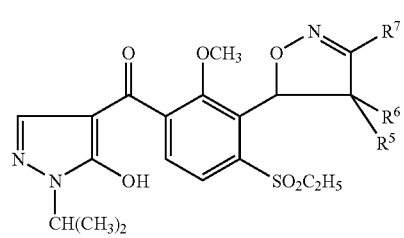

Ia59

Particular preference is likewise given to the compounds Ia60, in particular to the compounds Ia60.1–Ia60.64 which differ from compounds Ia1.1–Ia1.64 in that $R^1$ is methoxy, $R^2$ is ethylsulfonyl and $R^{13}$ is tert-butyl.

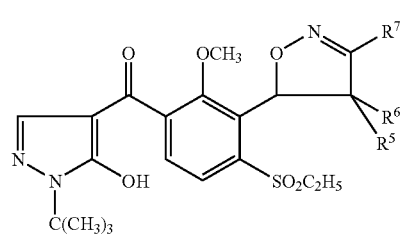

Ia60

Particular preference is likewise given to the compounds Ia61, in particular to the compounds Ia61.1–Ia61.64 which differ from compounds Ia1.1–Ia1.64 in that $R^1$ is methoxy, $R^2$ is ethylsulfonyl and $R^{14}$ is methyl.

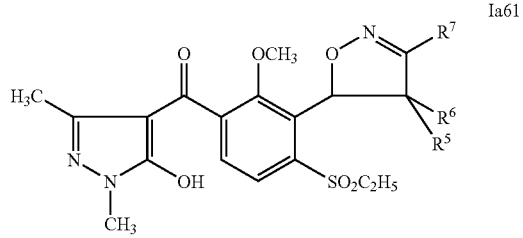

Ia61

Particular preference is likewise given to the compounds Ia62, in particular to the compounds Ia62.1–Ia62.64 which differ from compounds Ia1.1–Ia1.64 in that $R^1$ is methoxy, $R^2$ is ethylsulfonyl, $R^{13}$ is ethyl and $R^{14}$ is methyl.

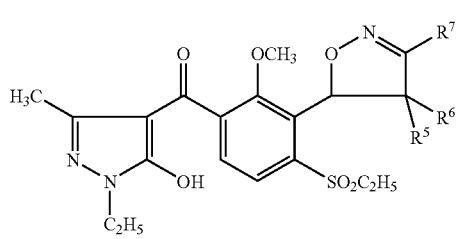

Ia62

Particular preference is likewise given to the compounds Ia63, in particular to the compounds Ia63.1–Ia63.64 which differ from compounds Ia1.1–Ia1.64 in that $R^1$ is methoxy, $R^2$ is ethylsulfonyl, $R^{13}$ is isopropyl and $R^{14}$ is methyl.

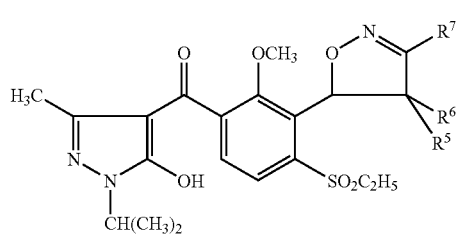

Ia63

Particular preference is likewise given to the compounds Ia64, in particular to the compounds Ia64.1–Ia64.64 which differ from compounds Ia1.1–Ia1.64 in that $R^1$ is methoxy, $R^2$ is ethylsulfonyl, $R^{13}$ is tert-butyl and $R^{14}$ is methyl.

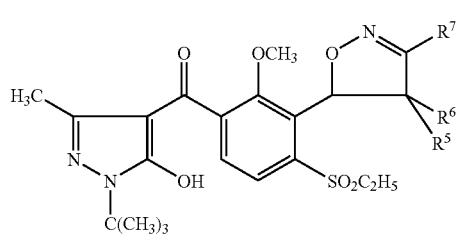

Ia64

Particular preference is likewise given to the compounds Ia65, in particular to the compounds Ia65.1–Ia65.64 which differ from compounds Ia1.1–Ia1.64 in that $R^2$ is chlorine.

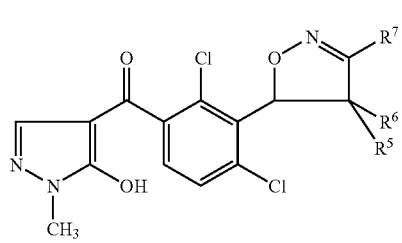

Ia65

Particular preference is likewise given to the compounds Ia66, in particular to the compounds Ia66.1–Ia66.64 which differ from compounds Ia1.1–Ia1.64 in that $R^2$ is chlorine and $R^{13}$ is ethyl.

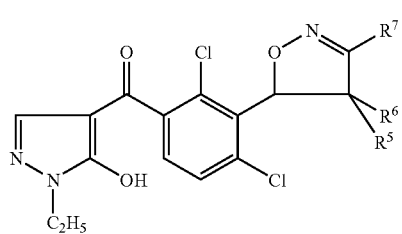

Ia66

Particular preference is likewise given to the compounds Ia67, in particular to the compounds Ia67.1–Ia67.64 which differ from compounds Ia1.1–Ia1.64 in that $R^2$ is chlorine and $R^{13}$ is isopropyl.

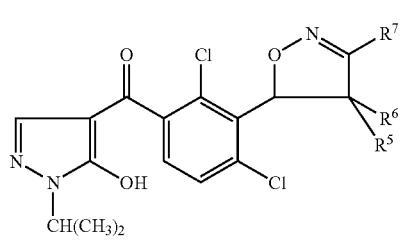

Ia67

Particular preference is likewise given to the compounds Ia68, in particular to the compounds Ia68.1–Ia68.64 which differ from compounds Ia1.1–Ia1.64 in that $R^2$ is chlorine and $R^{13}$ is tert-butyl.

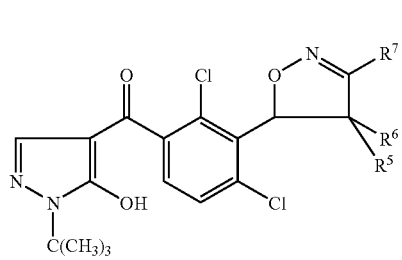

Ia68

Particular preference is likewise given to the compounds Ia69, in particular to the compounds Ia69.1–Ia69.64 which differ from compounds Ia1.1–Ia1.64 in that $R^2$ is chlorine and $R^{14}$ is methyl.

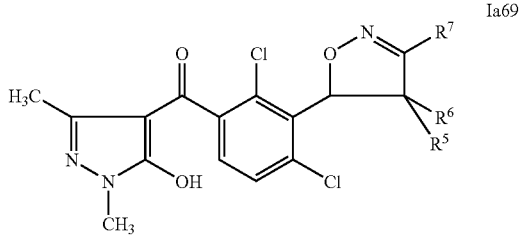

Ia69

Particular preference is likewise given to the compounds Ia70, in particular to the compounds Ia70.1–Ia70.64 which differ from compounds Ia1.1–Ia1.64 in that $R^2$ is chlorine, $R^{13}$ is ethyl and $R^{14}$ is methyl.

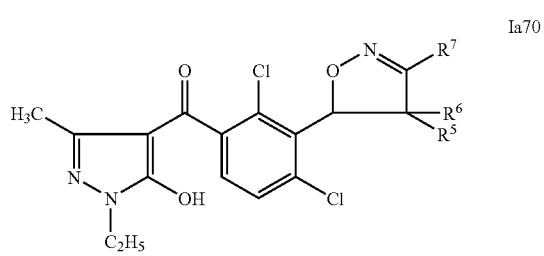

Ia70

Particular preference is likewise given to the compounds Ia71, in particular to the compounds Ia71.1–Ia71.64 which differ from compounds Ia1.1–Ia1.64 in that $R^2$ is chlorine, $R^{13}$ is isopropyl and $R^{14}$ is methyl.

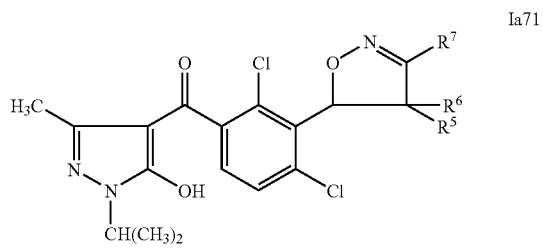

Ia71

Particular preference is likewise given to the compounds Ia72, in particular to the compounds Ia72.1–Ia72.64 which differ from compounds Ia1.1–Ia1.64 in that $R^2$ is chlorine, $R^{13}$ is tert-butyl and $R^{14}$ is methyl.

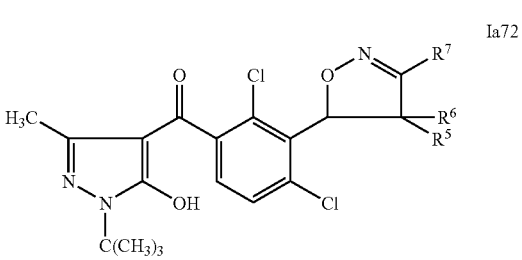

Ia72

Particular preference is likewise given to the compounds Ia73, in particular to the compounds Ia73.1–Ia73.64 which differ from compounds Ia1.1–Ia1.64 in that $R^1$ is methyl and $R^2$ is chlorine.

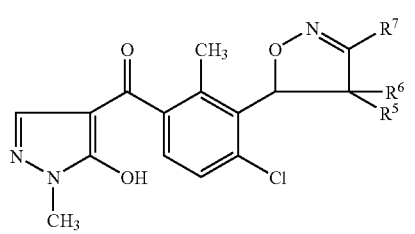

Ia73

Particular preference is likewise given to the compounds Ia74, in particular to the compounds Ia74.1–Ia74.64 which differ from compounds Ia1.1–Ia1.64 in that $R^1$ is methyl, $R^2$ is chlorine and $R^{13}$ is ethyl.

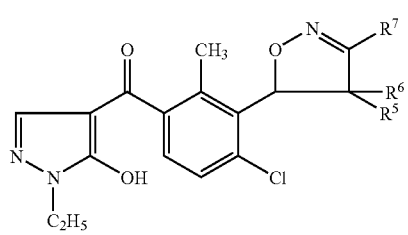

Ia74

Particular preference is likewise given to the compounds Ia75, in particular to the compounds Ia75.1–Ia75.64 which differ from compounds Ia1.1–Ia1.64 in that $R^1$ is methyl, $R^2$ is chlorine and $R^{13}$ is isopropyl.

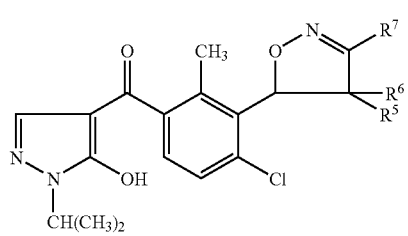

Ia75

Particular preference is likewise given to the compounds Ia76, in particular to the compounds Ia76.1–Ia76.64 which differ from compounds Ia1.1–Ia1.64 in that $R^1$ is methyl, $R^2$ is chlorine and $R^{13}$ is tert-butyl.

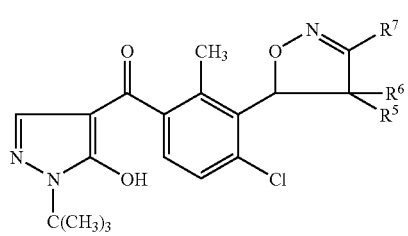

Ia76

Particular preference is likewise given to the compounds Ia77, in particular to the compounds Ia77.1–Ia77.64 which differ from compounds Ia1.1–Ia1.64 in that $R^1$ and $R^{14}$ are methyl and $R^2$ is chlorine.

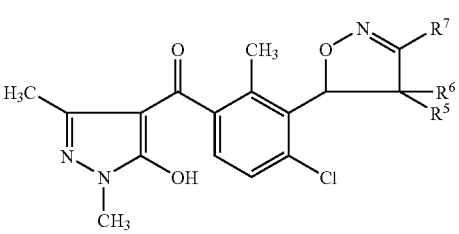

Ia77

Particular preference is likewise given to the compounds Ia78, in particular to the compounds Ia78.1–Ia78.64 which differ from compounds Ia1.1–Ia1.64 in that $R^1$ and $R^{14}$ are methyl, $R^2$ is chlorine and $R^{13}$ is ethyl.

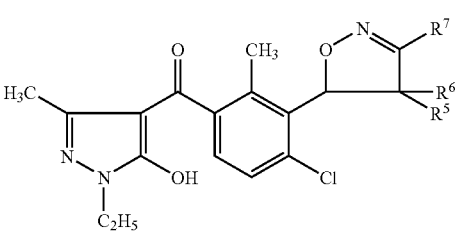

Ia78

Particular preference is likewise given to the compounds Ia79, in particular to the compounds Ia79.1–Ia79.64 which differ from compounds Ia1.1–Ia1.64 in that $R^1$ and $R^{14}$ are methyl, $R^2$ is chlorine and $R^{13}$ is isopropyl.

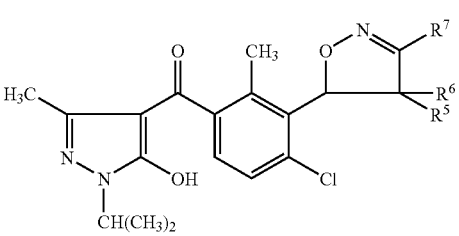

Ia79

Particular preference is likewise given to the compounds Ia80, in particular to the compounds Ia80.1–Ia80.64 which differ from compounds Ia1.1–Ia1.64 in that $R^1$ and $R^{14}$ are methyl, $R^2$ is chlorine and $R^{13}$ is tert-butyl.

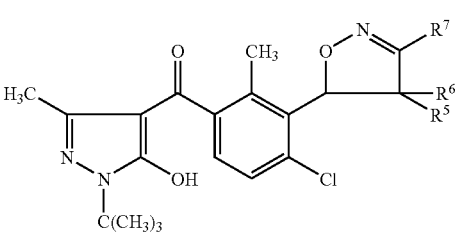

Ia80

Particular preference is likewise given to the compounds Ia81, in particular to the compounds Ia81.1–Ia81.64 which differ from compounds Ia1.1–Ia1.64 in that $R^1$ is trifluoromethyl and $R^2$ is chlorine.

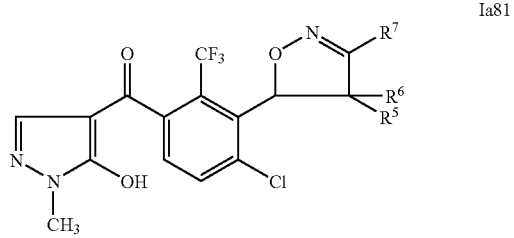

Ia81

Particular preference is likewise given to the compounds Ia82, in particular to the compounds Ia82.1–Ia82.64 which differ from compounds Ia1.1–Ia1.64 in that $R^1$ is trifluoromethyl, $R^2$ is chlorine and $R^{13}$ is ethyl.

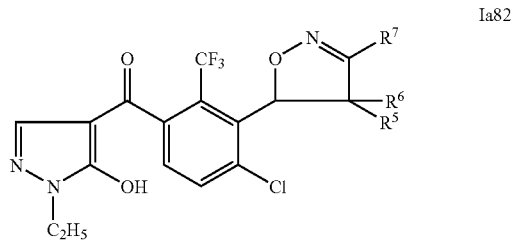

Ia82

Particular preference is likewise given to the compounds Ia83, in particular to the compounds Ia83.1–Ia83.64 which differ from compounds Ia1.1–Ia1.64 in that $R^1$ is trifluoromethyl, $R^2$ is chlorine and $R^{13}$ is isopropyl.

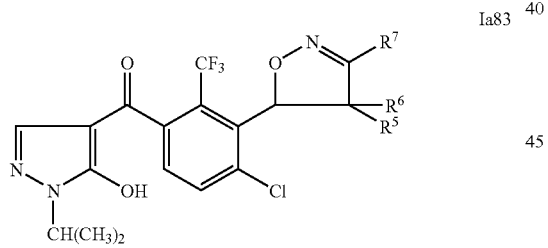

Ia83

Particular preference is likewise given to the compounds Ia84, in particular to the compounds Ia84.1–Ia84.64 which differ from compounds Ia1.1–Ia1.64 in that $R^1$ is trifluoromethyl, $R^2$ is chlorine and $R^{13}$ is tert-butyl.

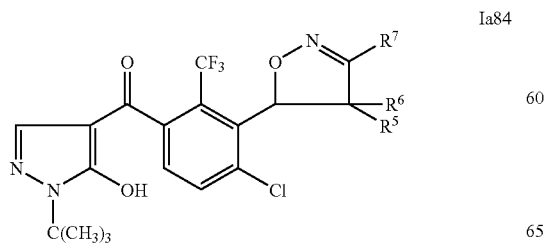

Ia84

Particular preference is likewise given to the compounds Ia85, in particular to the compounds Ia85.1–Ia85.64 which differ from compounds Ia1.1–Ia1.64 in that $R^1$ is trifluoromethyl, $R^2$ is chlorine and $R^{14}$ is methyl.

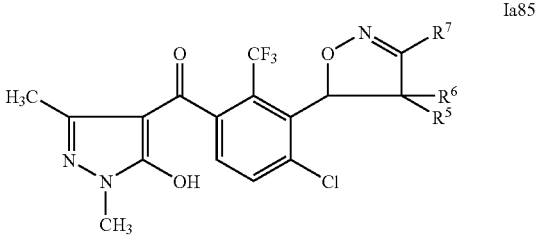

Ia85

Particular preference is likewise given to the compounds Ia86, in particular to the compounds Ia86.1–Ia86.64 which differ from compounds Ia1.1–Ia1.64 in that $R^1$ is trifluoromethyl, $R^2$ is chlorine, $R^{13}$ is ethyl and $R^{14}$ is methyl.

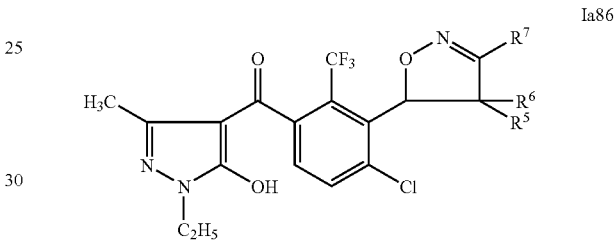

Ia86

Particular preference is likewise given to the compounds Ia87, in particular to the compounds Ia87.1–Ia87.64 which differ from compounds Ia1.1–Ia1.64 in that $R^1$ is trifluoromethyl, $R^2$ is chlorine, $R^{13}$ is isopropyl and $R^{14}$ is methyl.

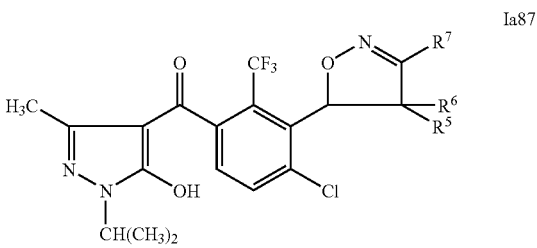

Ia87

Particular preference is likewise given to the compounds Ia88, in particular to the compounds Ia88.1–Ia88.64 which differ from compounds Ia1.1–Ia1.64 in that $R^1$ is trifluoromethyl, $R^2$ is chlorine, $R^{13}$ is tert-butyl and $R^{14}$ is methyl.

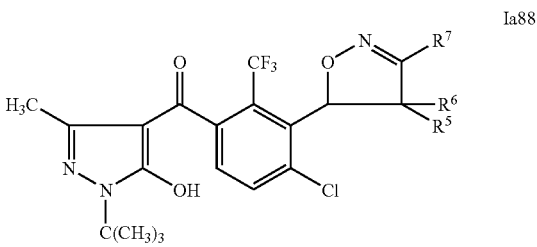

Ia88

Particular preference is likewise given to the compounds Ia89, in particular to the compounds Ia89.1–Ia89.64 which differ from compounds Ia1.1–Ia1.64 in that $R^1$ is methoxy and $R^2$ is chlorine.

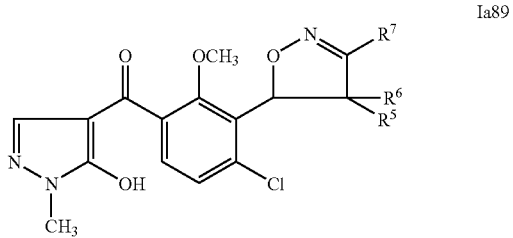

Ia89

Particular preference is likewise given to the compounds Ia90, in particular to the compounds Ia90.1–Ia90.64 which differ from compounds Ia1.1–Ia1.64 in that $R^1$ is methoxy, $R^2$ is chlorine and $R^{13}$ is ethyl.

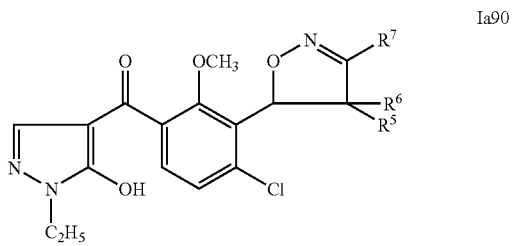

Ia90

Particular preference is likewise given to the compounds Ia91, in particular to the compounds Ia91.1–Ia91.64 which differ from compounds Ia1.1–Ia1.64 in that $R^1$ is methoxy, $R^2$ is chlorine and $R^{13}$ is isopropyl.

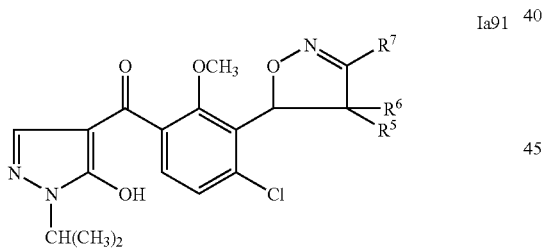

Ia91

Particular preference is likewise given to the compounds Ia92, in particular to the compounds Ia92.1–Ia92.64 which differ from compounds Ia1.1–Ia1.64 in that $R^1$ is methoxy, $R^2$ is chlorine and $R^{13}$ is tert-butyl.

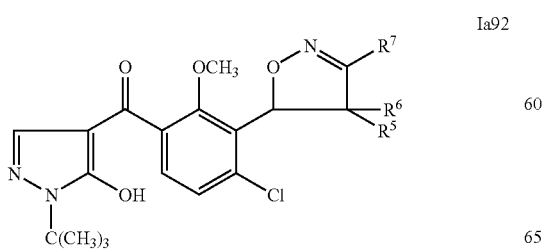

Ia92

Particular preference is likewise given to the compounds Ia93, in particular to the compounds Ia93.1–Ia93.64 which differ from compounds Ia1.1–Ia1.64 in that $R^1$ is methoxy, $R^2$ is chlorine and $R^{14}$ is methyl.

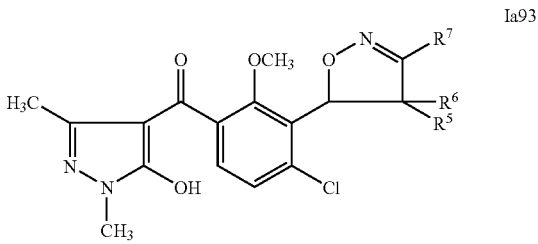

Ia93

Particular preference is likewise given to the compounds Ia94, in particular to the compounds Ia94.1–Ia94.64 which differ from compounds Ia1.1–Ia1.64 in that $R^1$ is methoxy, $R^2$ is chlorine, $R^{13}$ is ethyl and $R^{14}$ is methyl.

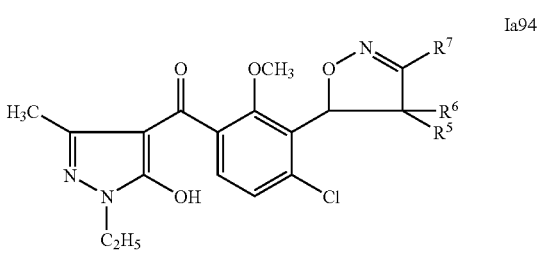

Ia94

Particular preference is likewise given to the compounds Ia95, in particular to the compounds Ia95.1–Ia95.64 which differ from compounds Ia1.1–Ia1.64 in that $R^1$ is methoxy, $R^2$ is chlorine, $R^{13}$ is isopropyl and $R^{14}$ is methyl.

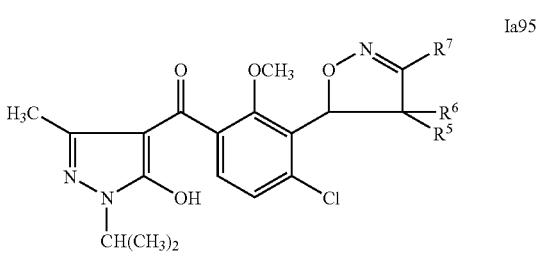

Ia95

Particular preference is likewise given to the compounds Ia96, in particular to the compounds Ia96.1–Ia96.64 which differ from compounds Ia1.1–Ia1.64 in that $R^1$ is methoxy, $R^2$ is chlorine, $R^{13}$ is tert-butyl and $R^{14}$ is methyl.

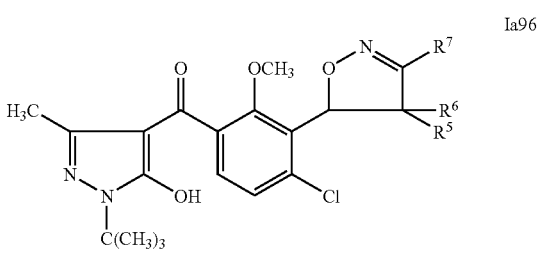

Ia96

Particular preference is likewise given to the compounds Ia97, in particular to the compounds Ia97.1–Ia97.64 which differ from compounds Ia1.1–Ia1.64 in that $R^2$ is trifluoromethyl.

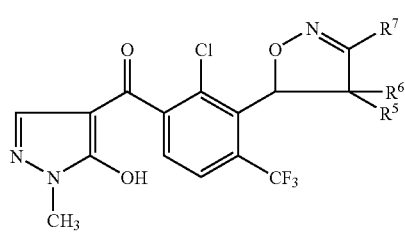

Ia97

Particular preference is likewise given to the compounds Ia98, in particular to the compounds Ia98.1–Ia98.64 which differ from compounds Ia1.1–Ia1.64 in that $R^2$ is trifluoromethyl and $R^{13}$ is ethyl.

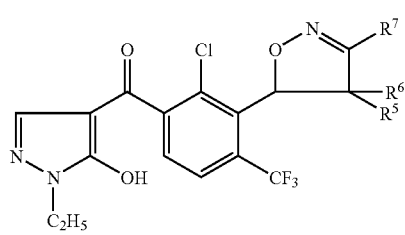

Ia98

Particular preference is likewise given to the compounds Ia99, in particular to the compounds Ia99.1–Ia99.64 which differ from compounds Ia1.1–Ia1.64 in that $R^2$ is trifluoromethyl and $R^{13}$ is ethyl.

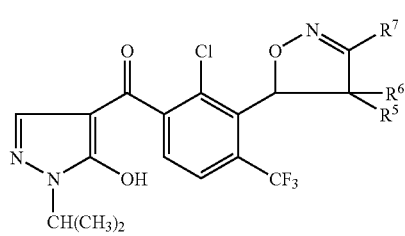

Ia99

Particular preference is likewise given to the compounds Ia100, in particular to the compounds Ia100.1–Ia100.64 which differ from compounds Ia1.1–Ia1.64 in that $R^2$ is trifluoromethyl and $R^{13}$ is tert-butyl.

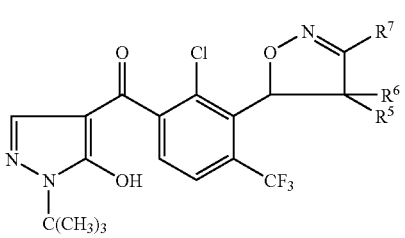

Ia100

Particular preference is likewise given to the compounds Ia101, in particular to the compounds Ia101.1–Ia101.64 which differ from compounds Ia1.1–Ia1.64 in that $R^2$ is trifluoromethyl and $R^{14}$ is methyl.

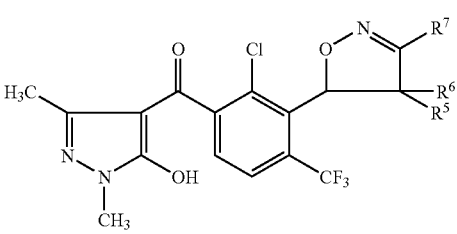

Ia101

Particular preference is likewise given to the compounds Ia102, in particular to the compounds Ia102.1–Ia102.64 which differ from compounds Ia1.1–Ia1.64 in that $R^2$ is trifluoromethyl, $R^{13}$ is ethyl and $R^{14}$ is methyl.

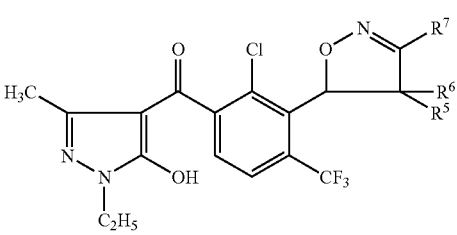

Ia102

Particular preference is likewise given to the compounds Ia103, in particular to the compounds Ia103.1–Ia103.64 which differ from compounds Ia1.1–Ia1.64 in that $R^2$ is trifluoromethyl, $R^{13}$ is isopropyl and $R^{14}$ is methyl.

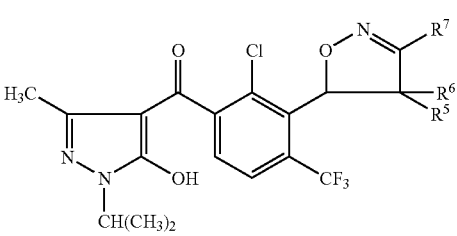

Ia103

Particular preference is likewise given to the compounds Ia104, in particular to the compounds Ia104.1–Ia104.64 which differ from compounds Ia1.1–Ia1.64 in that $R^2$ is trifluoromethyl, $R^{13}$ is tert-butyl and $R^{14}$ is methyl.

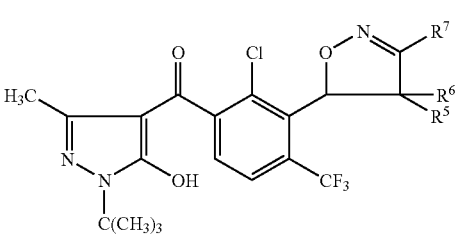

Ia104

Particular preference is likewise given to the compounds Ia105, in particular to the compounds Ia105.1–Ia105.64 which differ from compounds Ia1.1–Ia1.64 in that $R^1$ is methyl and $R^2$ is trifluoromethyl.

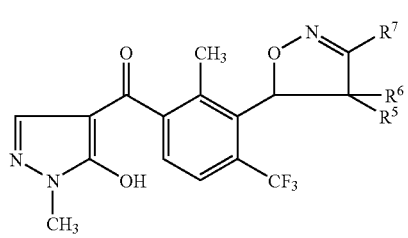

Ia105

Particular preference is likewise given to the compounds Ia106, in particular to the compounds Ia106.1–Ia106.64 which differ from compounds Ia1.1–Ia1.64 in that $R^1$ is methyl, $R^2$ is trifluoromethyl and $R^{13}$ is ethyl.

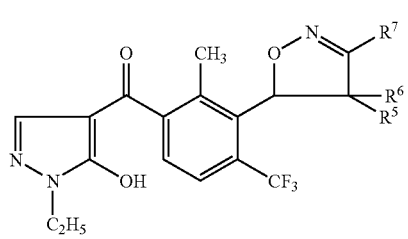

Ia106

Particular preference is likewise given to the compounds Ia107, in particular to the compounds Ia107.1–Ia107.64 which differ from compounds Ia1.1–Ia1.64 in that $R^1$ is methyl, $R^2$ is trifluoromethyl and $R^{13}$ is isopropyl.

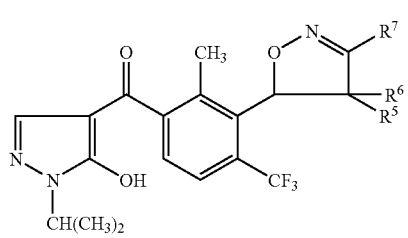

Ia107

Particular preference is likewise given to the compounds Ia108, in particular to the compounds Ia108.1–Ia108.64 which differ from compounds Ia1.1–Ia1.64 in that $R^1$ is methyl, $R^2$ is trifluoromethyl and $R^{13}$ is tert-butyl.

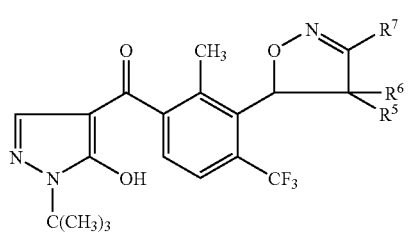

Ia108

Particular preference is likewise given to the compounds Ia109, in particular to the compounds Ia109.1–Ia109.64 which differ from compounds Ia1.1–Ia1.64 in that $R^1$ and $R^{14}$ are methyl and $R^2$ is trifluoromethyl.

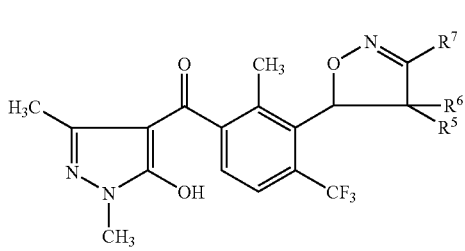

Ia109

Particular preference is likewise given to the compounds Ia110, in particular to the compounds Ia110.1–Ia110.64 which differ from compounds Ia1.1–Ia1.64 in that $R^1$ and $R^{14}$ are methyl, $R^2$ is trifluoromethyl and $R^{13}$ is ethyl.

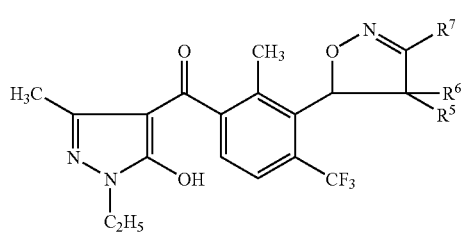

Ia110

Particular preference is likewise given to the compounds Ia111, in particular to the compounds Ia111.1–Ia111.64 which differ from compounds Ia1.1–Ia1.64 in that $R^1$ and $R^{14}$ are methyl, $R^2$ is trifluoromethyl and $R^{13}$ is isopropyl.

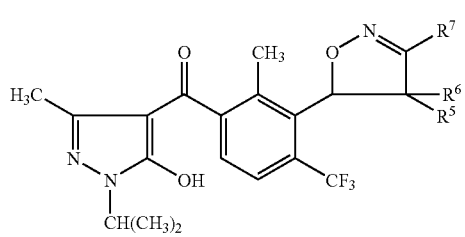

Ia111

Particular preference is likewise given to the compounds Ia112, in particular to the compounds Ia112.1–Ia112.64 which differ from compounds Ia1.1–Ia1.64 in that $R^1$ and $R^{14}$ are methyl, $R^2$ is trifluoromethyl and $R^{13}$ is tert-butyl.

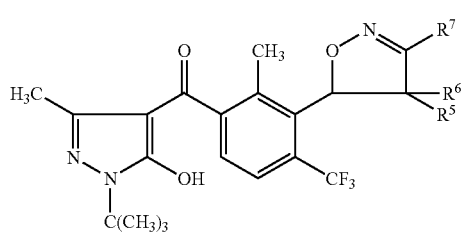

Ia112

Particular preference is likewise given to the compounds Ia113, in particular to the compounds Ia113.1–Ia113.64 which differ from compounds Ia1.1–Ia1.64 in that $R^1$ and $R^2$ are trifluoromethyl.

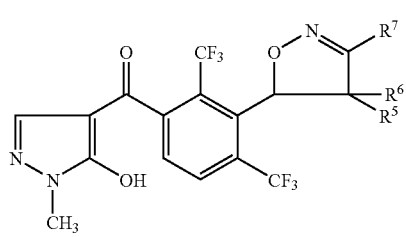

Ia113

Particular preference is likewise given to the compounds Ia114, in particular to the compounds Ia114.1–Ia114.64 which differ from compounds Ia1.1–Ia1.64 in that $R^1$ and $R^2$ are trifluoromethyl and $R^{13}$ is ethyl.

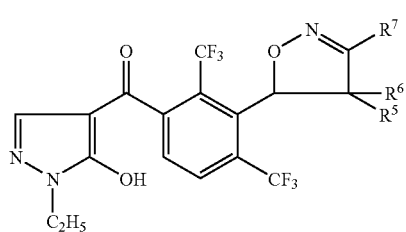

Ia114

Particular preference is likewise given to the compounds Ia115, in particular to the compounds Ia115.1–Ia115.64 which differ from compounds Ia1.1–Ia1.64 in that $R^1$ and $R^2$ are trifluoromethyl and $R^{13}$ is isopropyl.

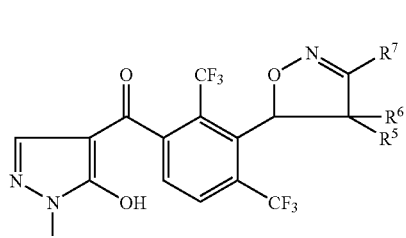

Ia115

Particular preference is likewise given to the compounds Ia116, in particular to the compounds Ia116.1–Ia116.64 which differ from compounds Ia1.1–Ia1.64 in that $R^1$ and $R^2$ are trifluoromethyl and $R^{13}$ is tert-butyl.

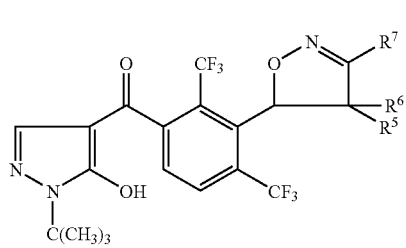

Ia116

Particular preference is likewise given to the compounds Ia117, in particular to the compounds Ia117.1–Ia117.64 which differ from compounds Ia1.1–Ia1.64 in that $R^1$ and $R^2$ are trifluoromethyl and $R^{14}$ is methyl.

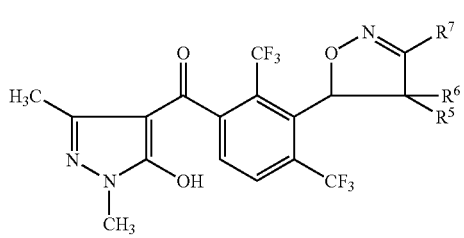

Ia117

Particular preference is likewise given to the compounds Ia118, in particular to the compounds Ia118.1–Ia118.64 which differ from compounds Ia1.1–Ia1.64 in that $R^1$ and $R^2$ are trifluoromethyl, $R^{13}$ is ethyl and $R^{14}$ is methyl.

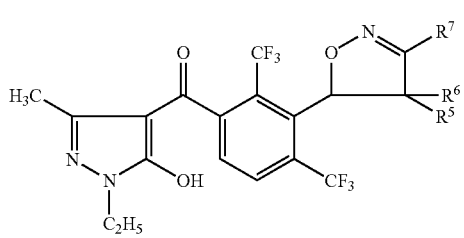

Ia118

Particular preference is likewise given to the compounds Ia119, in particular to the compounds Ia119.1–Ia119.64 which differ from compounds Ia1.1–Ia1.64 in that $R^1$ and $R^2$ are trifluoromethyl, $R^{13}$ is isopropyl and $R^{14}$ is methyl.

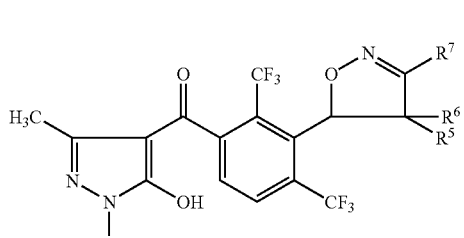

Ia119

Particular preference is likewise given to the compounds Ia120, in particular to the compounds Ia120.1–Ia120.64 which differ from compounds Ia1.1–Ia1.64 in that $R^1$ and $R^2$ are trifluoromethyl, $R^{13}$ is tert-butyl and $R^{14}$ is methyl.

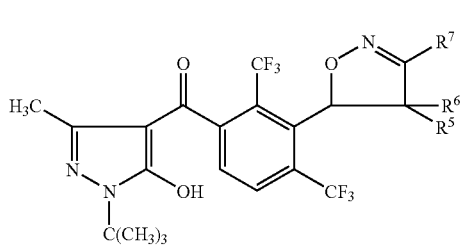

Ia120

Particular preference is likewise given to the compounds Ia121, in particular to the compounds Ia121.1–Ia121.64 which differ from compounds Ia1.1–Ia1.64 in that $R^1$ is methoxy and $R^2$ is trifluoromethyl.

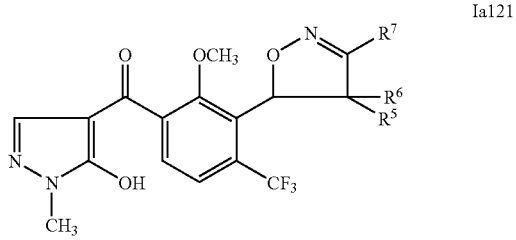

Ia121

Particular preference is likewise given to the compounds Ia122, in particular to the compounds Ia122.1–Ia122.64 which differ from compounds Ia1.1–Ia1.64 in that $R^1$ is methoxy, $R^2$ is trifluoromethyl and $R^{13}$ is ethyl.

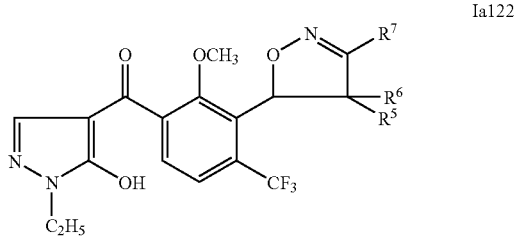

Ia122

Particular preference is likewise given to the compounds Ia123, in particular to the compounds Ia123.1–Ia123.64 which differ from compounds Ia1.1–Ia1.64 in that $R^1$ is methoxy, $R^2$ is trifluoromethyl and $R^{13}$ is isopropyl.

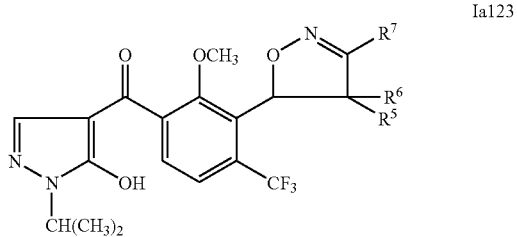

Ia123

Particular preference is likewise given to the compounds Ia124, in particular to the compounds Ia124.1–Ia124.64 which differ from compounds Ia1.1–Ia1.64 in that $R^1$ is methoxy, $R^2$ is trifluoromethyl and $R^{13}$ is tert-butyl.

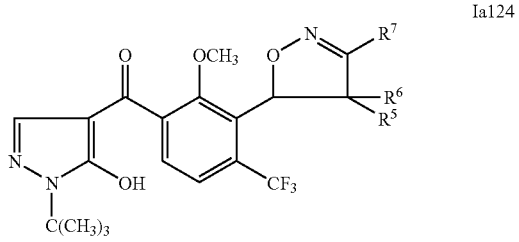

Ia124

Particular preference is likewise given to the compounds Ia125, in particular to the compounds Ia125.1–Ia125.64 which differ from compounds Ia1.1–Ia1.64 in that $R^1$ is methoxy, $R^2$ is trifluoromethyl and $R^{14}$ is methyl.

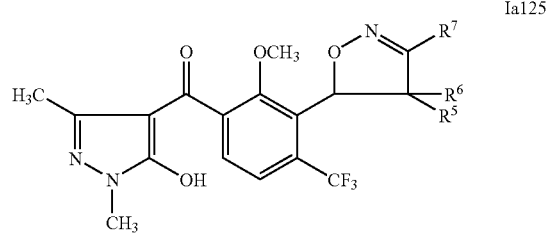

Ia125

Particular preference is likewise given to the compounds Ia126, in particular to the compounds Ia126.1–Ia126.64 which differ from compounds Ia1.1–Ia1.64 in that $R^1$ is methoxy, $R^2$ is trifluoromethyl, $R^{13}$ is ethyl and $R^{14}$ is methyl.

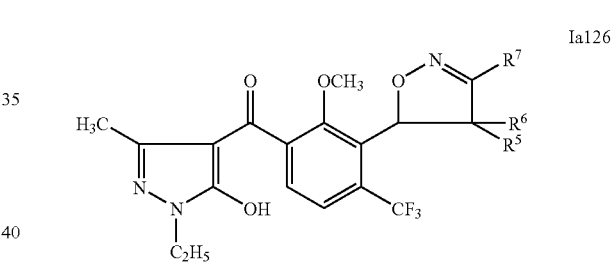

Ia126

Particular preference is likewise given to the compounds Ia127, in particular to the compounds Ia127.1–Ia127.64 which differ from compounds Ia1.1–Ia1.64 in that $R^1$ is methoxy, $R^2$ is trifluoromethyl, $R^{13}$ is isopropyl and $R^{14}$ is methyl.

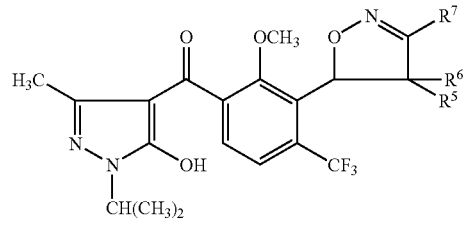

Ia127

Particular preference is likewise given to the compounds Ia128, in particular to the compounds Ia128.1–Ia128.64 which differ from compounds Ia1.1–Ia1.64 in that $R^1$ is methoxy, $R^2$ is trifluoromethyl, $R^{13}$ is tert-butyl and $R^{14}$ is methyl.

Particular preference is likewise given to the compounds Ia129, in particular to the compounds Ia129.1–Ia129.64 which differ from compounds Ia1.1–Ia1.64 in that $R^3$ is chlorine.

Particular preference is likewise given to the compounds Ia130, in particular to the compounds Ia130.1–Ia130.64 which differ from compounds Ia1.1–Ia1.64 in that $R^3$ is chlorine and $R^{13}$ is ethyl.

Particular preference is likewise given to the compounds Ia131, in particular to the compounds Ia131.1–Ia131.64 which differ from compounds Ia1.1–Ia1.64 in that $R^3$ is chlorine and $R^{13}$ is isopropyl.

Particular preference is likewise given to the compounds Ia132, in particular to the compounds Ia132.1–Ia132.64 which differ from compounds Ia1.1–Ia1.64 in that $R^3$ is chlorine and $R^{13}$ is tert-butyl.

Particular preference is likewise given to the compounds Ia133, in particular to the compounds Ia133.1–Ia133.64 which differ from compounds Ia1.1–Ia1.64 in that $R^3$ is chlorine and $R^{14}$ is methyl.

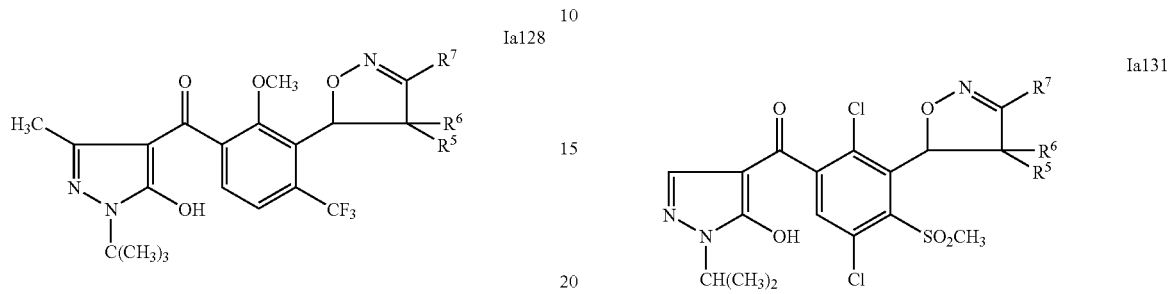

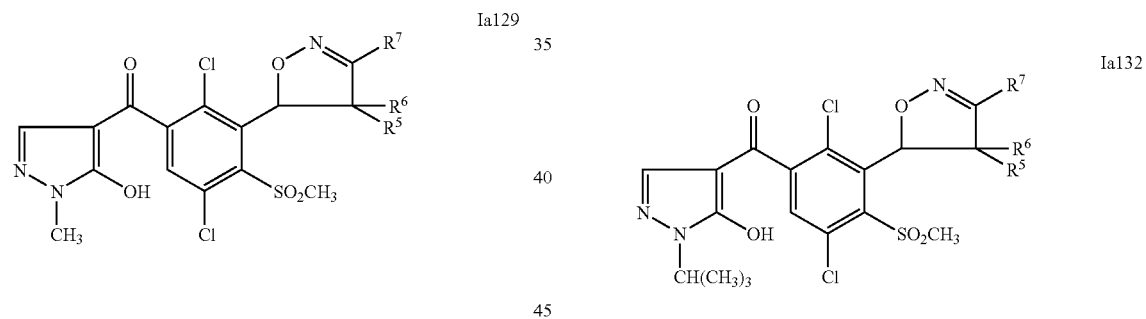

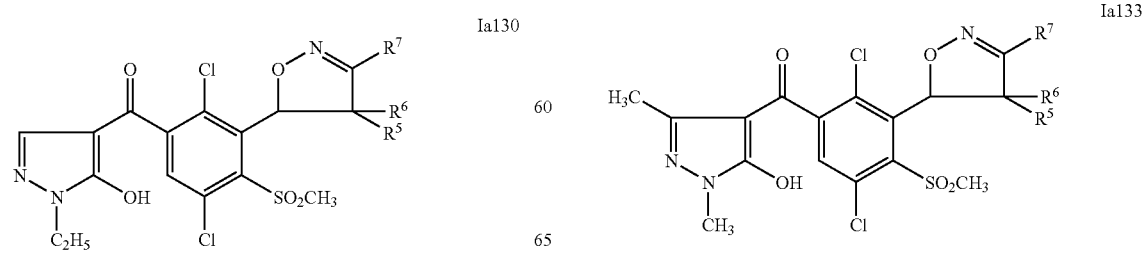

Particular preference is likewise given to the compounds Ia134, in particular to the compounds Ia134.1–Ia134.64 which differ from compounds Ia1.1–Ia1.64 in that $R^3$ is chlorine, $R^{13}$ is ethyl and $R^{14}$ is methyl.

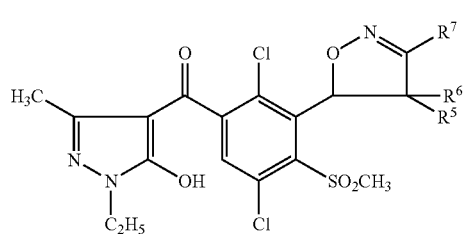
Ia134

Particular preference is likewise given to the compounds Ia135, in particular to the compounds Ia135.1–Ia135.64 which differ from compounds Ia1.1–Ia1.64 in that $R^3$ is chlorine, $R^{13}$ is isopropyl and $R^{14}$ is methyl.

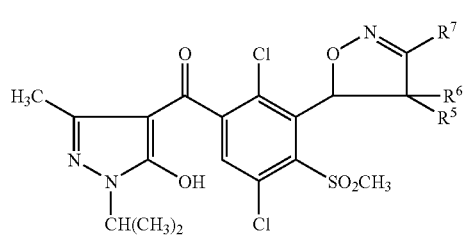
Ia135

Particular preference is likewise given to the compounds Ia136, in particular to the compounds Ia136.1–Ia136.64 which differ from compounds Ia1.1–Ia1.64 in that $R^3$ is chlorine, $R^{13}$ is tert-butyl and $R^{14}$ is methyl.

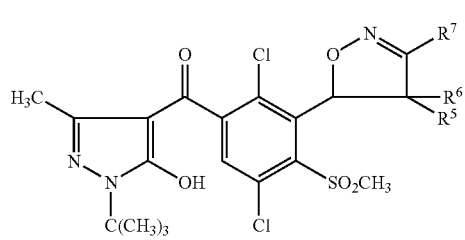
Ia136

Particular preference is likewise given to the compounds Ia137, in particular to the compounds Ia137.1–Ia137.64 which differ from compounds Ia1.1–Ia1.64 in that $R^1$ is methyl and $R^3$ is chlorine.

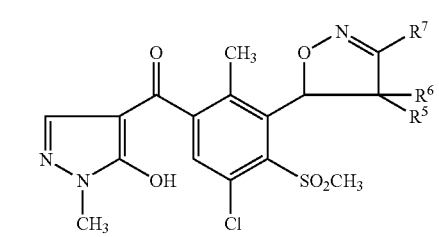
Ia137

Particular preference is likewise given to the compounds Ia138, in particular to the compounds Ia138.1–Ia138.64 which differ from compounds Ia1.1–Ia1.64 in that $R^1$ is methyl, $R^3$ is chlorine and $R^{13}$ is ethyl.

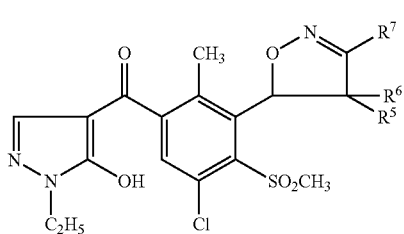
Ia138

Particular preference is likewise given to the compounds Ia139, in particular to the compounds Ia139.1–Ia139.64 which differ from compounds Ia1.1–Ia1.64 in that $R^1$ is methyl, $R^3$ is chlorine and $R^{13}$ is isopropyl.

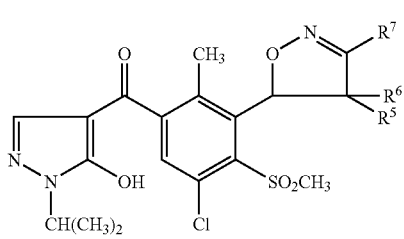
Ia139

Particular preference is likewise given to the compounds Ia140, in particular to the compounds Ia140.1–Ia140.64 which differ from compounds Ia1.1–Ia1.64 in that $R^1$ is methyl, $R^3$ is chlorine and $R^{13}$ is tert-butyl.

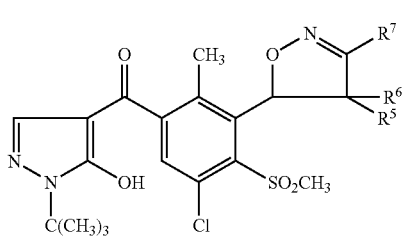
Ia140

Particular preference is likewise given to the compounds Ia141, in particular to the compounds Ia141.1–Ia141.64 which differ from compounds Ia1.1–Ia1.64 in that $R^1$ and $R^{14}$ are methyl and $R^3$ is chlorine.

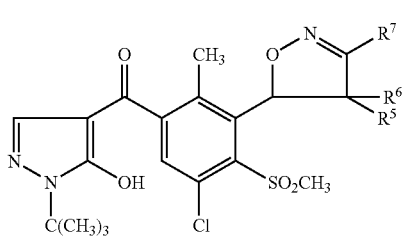
Ia141

Particular preference is likewise given to the compounds Ia142, in particular to the compounds Ia142.1–Ia142.64 which differ from compounds Ia1.1–Ia1.64 in that $R^1$ and $R^{14}$ are methyl, $R^3$ is chlorine and $R^{13}$ is ethyl.

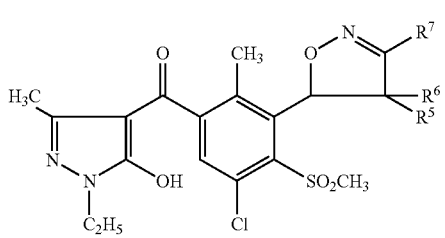

Ia142

Particular preference is likewise given to the compounds Ia143, in particular to the compounds Ia143.1–Ia143.64 which differ from compounds Ia1.1–Ia1.64 in that $R^1$ and $R^{14}$ are methyl, $R^3$ is chlorine and $R^{13}$ is isopropyl.

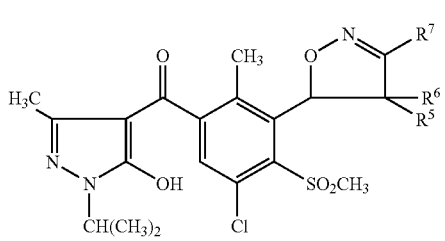

Ia143

Particular preference is likewise given to the compounds Ia144, in particular to the compounds Ia144.1–Ia144.64 which differ from compounds Ia1.1–Ia1.64 in that $R^1$ and $R^{14}$ are methyl, $R^3$ is chlorine and $R^{13}$ is tert-butyl.

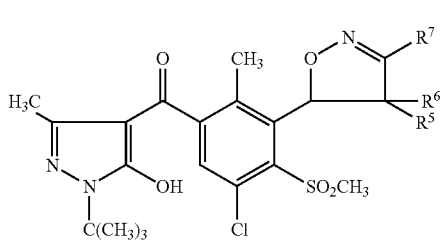

Ia144

Particular preference is likewise given to the compounds Ia145, in particular to the compounds Ia145.1–Ia145.64 which differ from compounds Ia1.1–Ia1.64 in that $R^2$ is ethylsulfonyl and $R^3$ is chlorine.

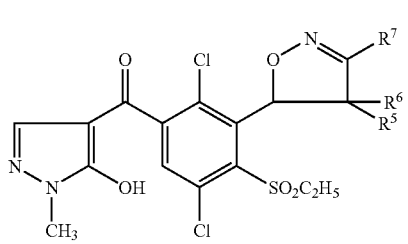

Ia145

Particular preference is likewise given to the compounds Ia146, in particular to the compounds Ia146.1–Ia146.64 which differ from compounds Ia1.1–Ia1.64 in that $R^2$ is ethylsulfonyl, $R^3$ is chlorine and $R^{13}$ is ethyl.

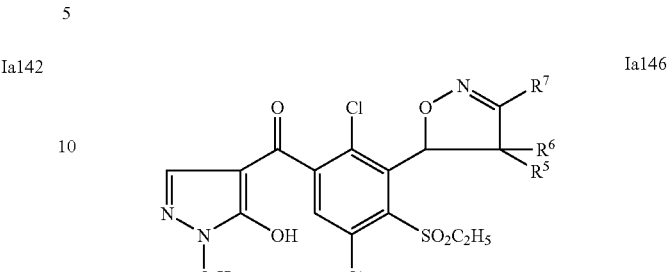

Ia146

Particular preference is likewise given to the compounds Ia147, in particular to the compounds Ia147.1–Ia147.64 which differ from compounds Ia1.1–Ia1.64 in that $R^2$ is ethylsulfonyl, $R^3$ is chlorine and $R^{13}$ is isopropyl.

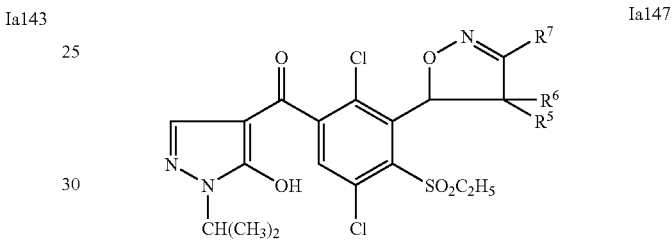

Ia147

Particular preference is likewise given to the compounds Ia148, in particular to the compounds Ia148.1–Ia148.64 which differ from compounds Ia1.1–Ia1.64 in that $R^2$ is ethylsulfonyl, $R^3$ is chlorine and $R^{13}$ is tert-butyl.

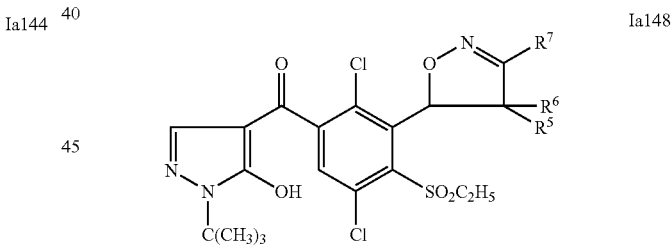

Ia148

Particular preference is likewise given to the compounds Ia149, in particular to the compounds Ia149.1–Ia149.64 which differ from compounds Ia1.1–Ia1.64 in that $R^2$ is ethylsulfonyl, $R^3$ is chlorine and $R^{14}$ is methyl.

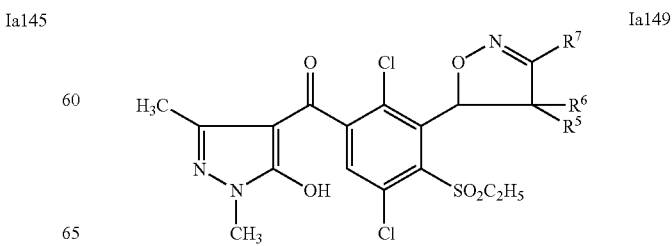

Ia149

Particular preference is likewise given to the compounds Ia150, in particular to the compounds Ia150.1–Ia150.64 which differ from compounds Ia1.1–Ia1.64 in that $R^2$ is ethylsulfonyl, $R^3$ is chlorine, $R^{13}$ is ethyl and $R^{14}$ is methyl.

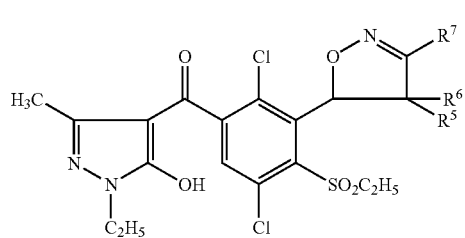

Particular preference is likewise given to the compounds Ia151, in particular to the compounds Ia151.1–Ia151.64 which differ from compounds Ia1.1–Ia1.64 in that $R^2$ is ethylsulfonyl, $R^3$ is chlorine, $R^{13}$ is isopropyl and $R^{14}$ is methyl.

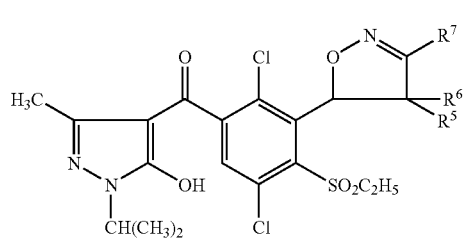

Particular preference is likewise given to the compounds Ia152, in particular to the compounds Ia152.1–Ia152.64 which differ from compounds Ia1.1–Ia1.64 in that $R^2$ is ethylsulfonyl, $R^3$ is chlorine, $R^{13}$ is tert-butyl and $R^{14}$ is methyl.

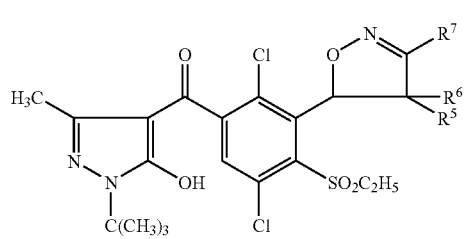

Particular preference is likewise given to the compounds Ia153, in particular to the compounds Ia153.1–Ia153.64 which differ from compounds Ia1.1–Ia1.64 in that $R^1$ is methyl and $R^2$ is ethylsulfonyl and $R^3$ is chlorine.

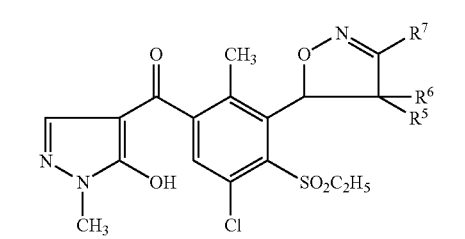

Particular preference is likewise given to the compounds Ia154, in particular to the compounds Ia154.1–Ia154.64 which differ from compounds Ia1.1–Ia1.64 in that $R^1$ is methyl $R^2$ is ethylsulfonyl, $R^3$ is chlorine and $R^{13}$ is ethyl.

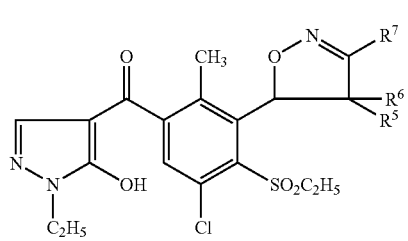

Particular preference is likewise given to the compounds Ia155, in particular to the compounds Ia155.1–Ia155.64 which differ from compounds Ia1.1–Ia1.64 in that $R^1$ is methyl, $R^2$ is ethylsulfonyl, $R^3$ is chlorine and $R^{13}$ is isopropyl.

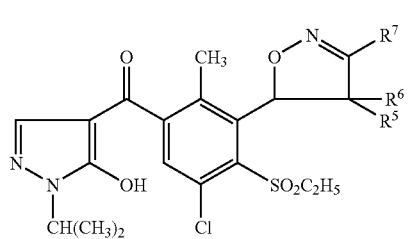

Particular preference is likewise given to the compounds Ia156, in particular to the compounds Ia156.1–Ia156.64 which differ from compounds Ia1.1–Ia1.64 in that $R^1$ is methyl, $R^2$ is ethylsulfonyl, $R^3$ is chlorine and $R^{13}$ is tert-butyl.

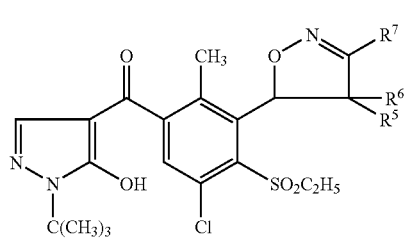

Particular preference is likewise given to the compounds Ia157, in particular to the compounds Ia157.1–Ia157.64 which differ from compounds Ia1.1–Ia1.64 in that $R^1$ and $R^{14}$ are methyl, $R^2$ is ethylsulfonyl and $R^3$ is chlorine.

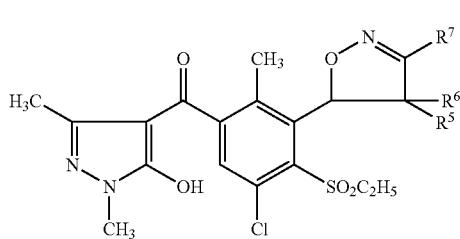

Particular preference is likewise given to the compounds Ia158, in particular to the compounds Ia158.1–Ia158.64 which differ from compounds Ia1.1–Ia1.64 in that $R^1$ and $R^{14}$ are methyl, $R^2$ is ethylsulfonyl, $R^3$ is chlorine and $R^{13}$ is ethyl.

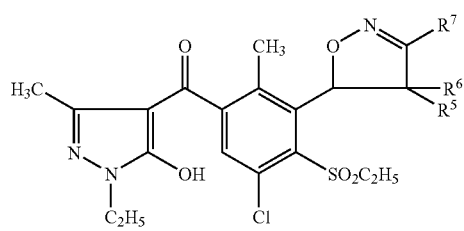

Ia158

Particular preference is likewise given to the compounds Ia159, in particular to the compounds Ia159.1–Ia159.64 which differ from compounds Ia1.1–Ia1.64 in that $R^1$ and $R^{14}$ are methyl, $R^2$ is ethylsulfonyl, $R^3$ is chlorine and $R^{13}$ is isopropyl.

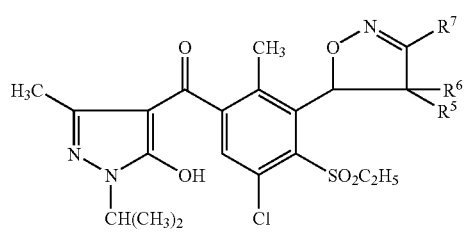

Ia159

Particular preference is likewise given to the compounds Ia160, in particular to the compounds Ia160.1–Ia160.64 which differ from compounds Ia1.1–Ia1.64 in that $R^1$ and $R^{14}$ are methyl, $R^2$ is ethylsulfonyl, $R^3$ is chlorine and $R^{13}$ is tert-butyl.

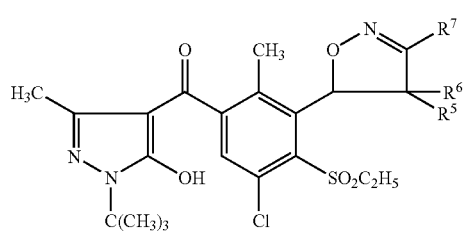

Ia160

Particular preference is likewise given to the compounds Ia161, in particular to the compounds Ia161.1–Ia161.64 which differ from compounds Ia1.1–Ia1.64 in that $R^2$ and $R^3$ are chlorine.

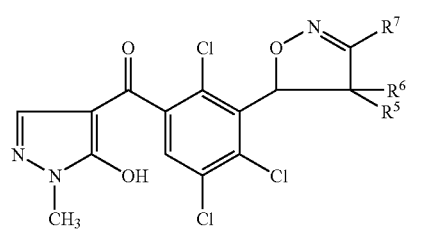

Ia161

Particular preference is likewise given to the compounds Ia162, in particular to the compounds Ia162.1–Ia162.64 which differ from compounds Ia1.1–Ia1.64 in that $R^2$ and $R^3$ are chlorine and $R^{13}$ is ethyl.

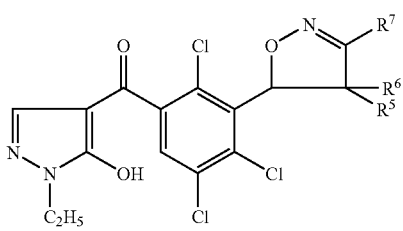

Ia162

Particular preference is likewise given to the compounds Ia163, in particular to the compounds Ia163.1–Ia163.64 which differ from compounds Ia1.1–Ia1.64 in that $R^2$ and $R^3$ are chlorine and $R^{13}$ is isopropyl.

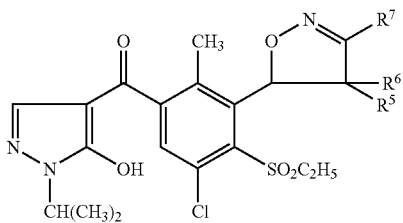

Ia163

Particular preference is likewise given to the compounds Ia164, in particular to the compounds Ia164.1–Ia164.64 which differ from compounds Ia1.1–Ia1.64 in that $R^2$ and $R^3$ are chlorine and $R^{13}$ is tert-butyl.

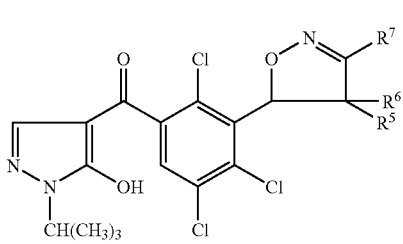

Ia164

Particular preference is likewise given to the compounds Ia165, in particular to the compounds Ia165.1–Ia165.64 which differ from compounds Ia1.1–Ia1.64 in that $R^2$ and $R^3$ are chlorine and $R^{14}$ is methyl.

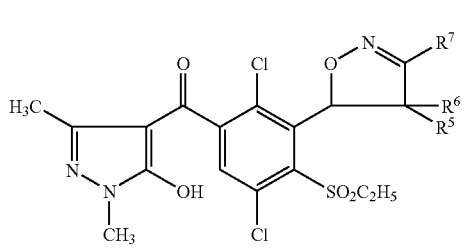

Ia165

Particular preference is likewise given to the compounds Ia166, in particular to the compounds Ia166.1–Ia166.64 which differ from compounds Ia1.1–Ia1.64 in that $R^2$ and $R^3$ are chlorine, $R^{13}$ is ethyl and $R^{14}$ is methyl.

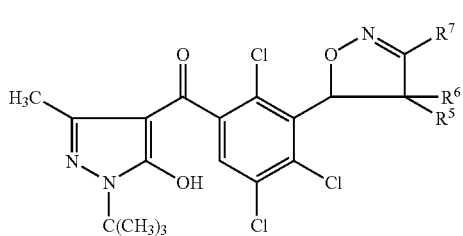

Ia166

Particular preference is likewise given to the compounds Ia167, in particular to the compounds Ia167.1–Ia167.64 which differ from compounds Ia1.1–Ia1.64 in that $R^2$ and $R^3$ are chlorine, $R^{13}$ is isopropyl and $R^{14}$ is methyl.

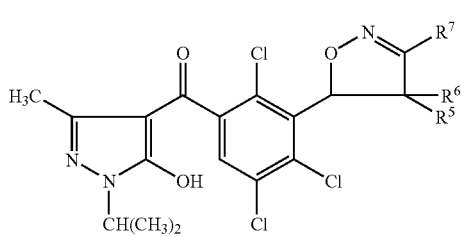

Ia167

Particular preference is likewise given to the compounds Ia168, in particular to the compounds Ia168.1–Ia168.64 which differ from compounds Ia1.1–Ia1.64 in that $R^2$ and $R^3$ are chlorine, $R^{13}$ is tert-butyl and $R^{14}$ is methyl.

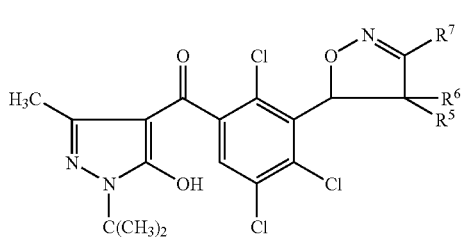

Ia168

Particular preference is likewise given to the compounds Ia169, in particular to the compounds Ia169.1–Ia169.64 which differ from compounds Ia1.1–Ia1.64 in that $R^1$ is methyl and $R^2$ and $R^3$ are chlorine.

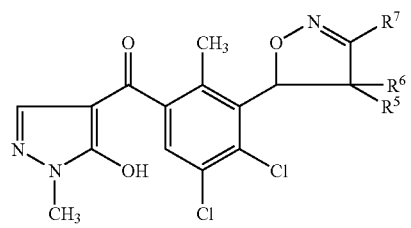

Ia169

Particular preference is likewise given to the compounds Ia170, in particular to the compounds Ia170.1–Ia170.64 which differ from compounds Ia1.1–Ia1.64 in that $R^1$ is methyl, $R^2$ and $R^3$ are chlorine and $R^{13}$ is ethyl.

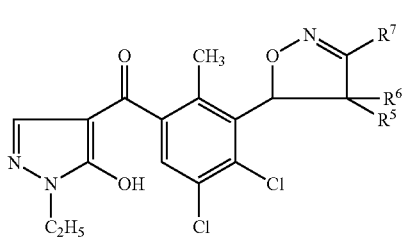

Ia170

Particular preference is likewise given to the compounds Ia171, in particular to the compounds Ia171.1–Ia171.64 which differ from compounds Ia1.1–Ia1.64 in that $R^1$ is methyl, $R^2$ and $R^3$ are chlorine and $R^{13}$ is isopropyl.

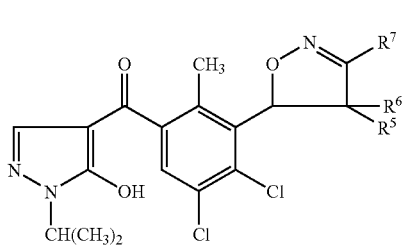

Ia171

Particular preference is likewise given to the compounds Ia172, in particular to the compounds Ia172.1–Ia172.64 which differ from compounds Ia1.1–Ia1.64 in that $R^1$ is methyl, $R^2$ and $R^3$ are chlorine and $R^{13}$ is tert-butyl.

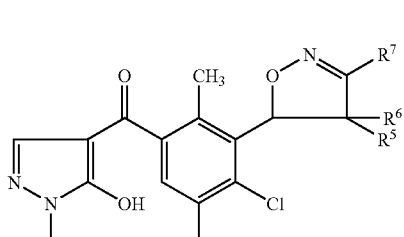

Ia172

Particular preference is likewise given to the compounds Ia173, in particular to the compounds Ia173.1–Ia173.64 which differ from compounds Ia1.1–Ia1.64 in that $R^1$ and $R^{14}$ are methyl and $R^2$ and $R^3$ are chlorine.

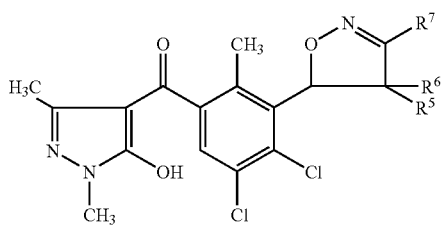

Ia173

Particular preference is likewise given to the compounds Ia174, in particular to the compounds Ia174.1–Ia174.64 which differ from compounds Ia1.1–Ia1.64 in that $R^1$ and $R^{14}$ are methyl, $R^2$ and $R^3$ are chlorine and $R^{13}$ is ethyl.

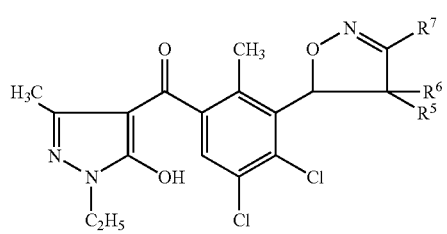

Ia174

Particular preference is likewise given to the compounds Ia175, in particular to the compounds Ia175.1–Ia175.64 which differ from compounds Ia1.1–Ia1.64 in that $R^1$ and $R^{14}$ are methyl, $R^2$ and $R^3$ are chlorine and $R^{13}$ is isopropyl.

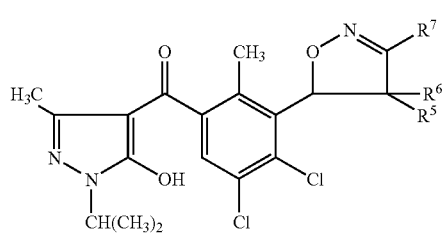

Ia175

Particular preference is likewise given to the compounds Ia176, in particular to the compounds Ia176.1–Ia176.64 which differ from compounds Ia1.1–Ia1.64 in that $R^1$ and $R^{14}$ are methyl, $R^2$ and $R^3$ are chlorine and $R^{13}$ is tert-butyl.

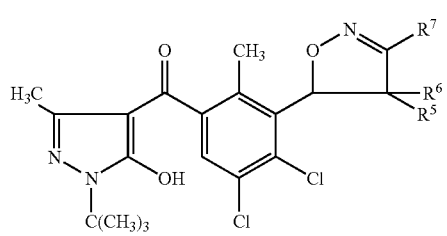

Ia176

Particular preference is likewise given to the compounds Ia177, in particular to the compounds Ia177.1–Ia177.64 which differ from compounds Ia1.1–Ia1.64 in that $R^1$ is chlorine and $R^3$ is methyl.

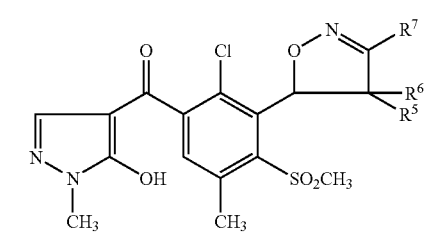

Ia177

Particular preference is likewise given to the compounds Ia178, in particular to the compounds Ia178.1–Ia178.64 which differ from compounds Ia1.1–Ia1.64 in that $R^3$ is methyl and $R^{13}$ is ethyl.

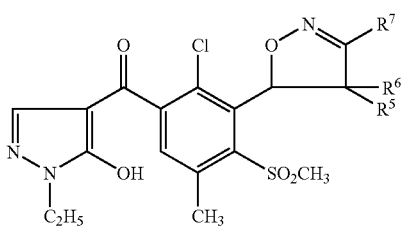

Ia178

Particular preference is likewise given to the compounds Ia179, in particular to the compounds Ia179.1–Ia178.64 [sic] which differ from compounds Ia1.1–Ia1.64 in that $R^3$ is methyl and $R^{13}$ is isopropyl.

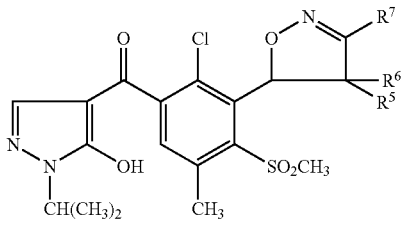

Ia179

Particular preference is likewise given to the compounds Ia180, in particular to the compounds Ia180.1–Ia180.64 which differ from compounds Ia1.1–Ia1.64 in that $R^3$ is methyl and $R^{13}$ is tert-butyl.

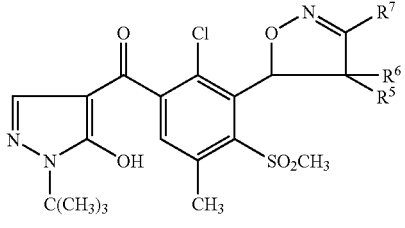

Ia180

Particular preference is likewise given to the compounds Ia181, in particular to the compounds Ia181.1–Ia181.64 which differ from compounds Ia1.1–Ia1.64 in that $R^3$ is methyl and $R^{14}$ is methyl.

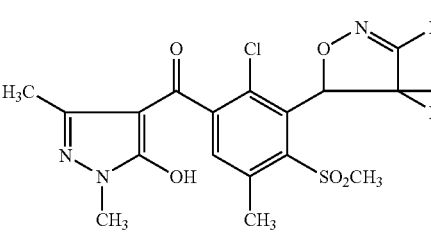

Ia181

Particular preference is likewise given to the compounds Ia182, in particular to the compounds Ia182.1–Ia182.64 which differ from compounds Ia1.1–Ia1.64 in that $R^3$ is methyl, $R^{13}$ is ethyl and $R^{14}$ is methyl.

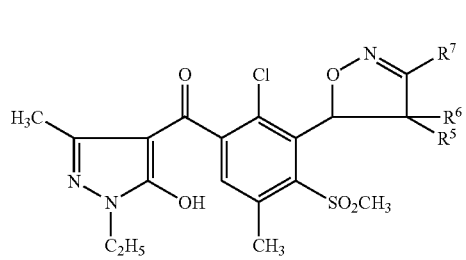

Ia182

Particular preference is likewise given to the compounds Ia183, in particular to the compounds Ia183.1–Ia183.64 which differ from compounds Ia1.1–Ia1.64 in that $R^3$ is methyl, $R^{13}$ is isopropyl and $R^{14}$ is methyl.

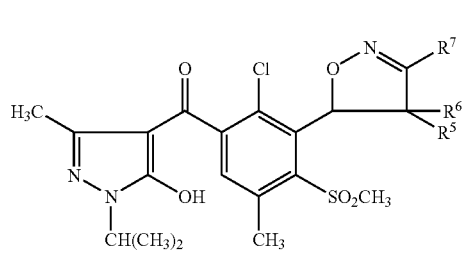

Ia183

Particular preference is likewise given to the compounds Ia184, in particular to the compounds Ia184.1–Ia184.64 which differ from compounds Ia1.1–Ia1.64 in that $R^3$ is methyl, $R^{13}$ is tert-butyl and $R^{14}$ is methyl.

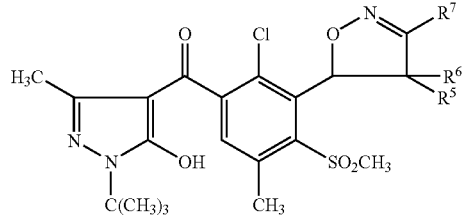

Ia184

Particular preference is likewise given to the compounds Ia185, in particular to the compounds Ia185.1–Ia185.64 which differ from compounds Ia1.1–Ia1.64 in that $R^1$ and $R^3$ are methyl.

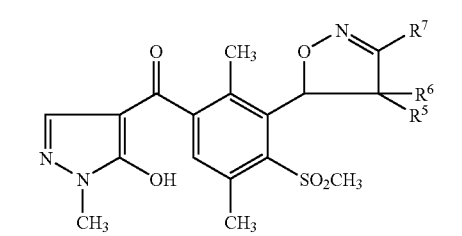

Ia185

Particular preference is likewise given to the compounds Ia186, in particular to the compounds Ia186.1–Ia186.64 which differ from compounds Ia1.1–Ia1.64 in that $R^1$ and $R^3$ are methyl and $R^{13}$ is ethyl.

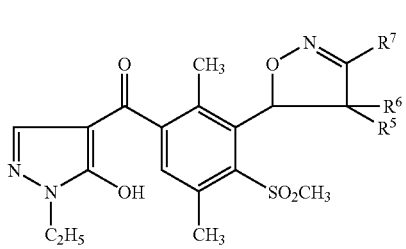

Ia186

Particular preference is likewise given to the compounds Ia187, in particular to the compounds Ia187.1–Ia187.64 which differ from compounds Ia1.1–Ia1.64 in that $R^1$ and $R^3$ are methyl and $R^{13}$ is isopropyl.

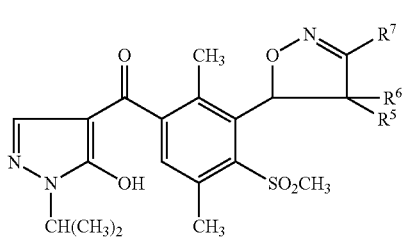

Ia187

Particular preference is likewise given to the compounds Ia188, in particular to the compounds Ia188.1–Ia188.64 which differ from compounds Ia1.1–Ia1.64 in that $R^1$ and $R^3$ are methyl and $R^{13}$ is tert-butyl.

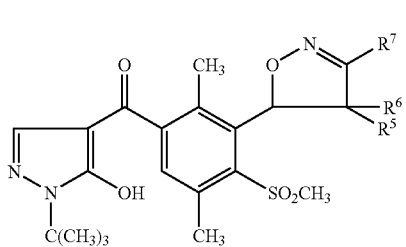

Ia188

Particular preference is likewise given to the compounds Ia189, in particular to the compounds Ia189.1–Ia189.64 which differ from compounds Ia1.1–Ia1.64 in that $R^1$, $R^3$ and $R^{14}$ are methyl.

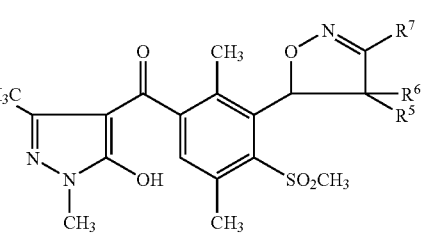

Ia189

Particular preference is likewise given to the compounds Ia190, in particular to the compounds Ia190.1–Ia190.64 which differ from compounds Ia1.1–Ia1.64 in that $R^1$, $R^3$ and $R^{14}$ are methyl and $R^{13}$ is ethyl.

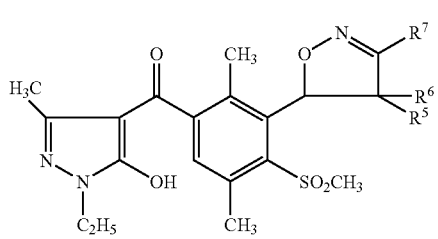

Ia190

Particular preference is likewise given to the compounds Ia191, in particular to the compounds Ia191.1–Ia191.64 which differ from compounds Ia1.1–Ia1.64 in that $R^1$, $R^3$ and $R^{14}$ are methyl and $R^{13}$ is isopropyl.

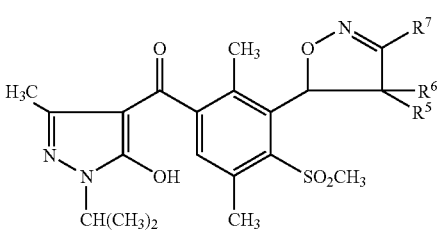

Ia191

Particular preference is likewise given to the compounds Ia192, in particular to the compounds Ia192.1–Ia192.64 which differ from compounds Ia1.1–Ia1.64 in that $R^1$, $R^3$ and $R^{14}$ are methyl and $R^{13}$ is tert-butyl.

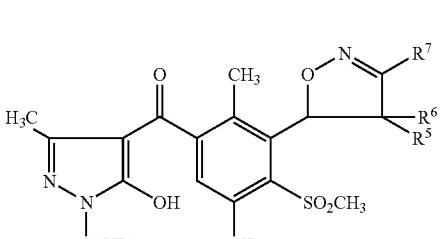

Ia192

Particular preference is likewise given to the compounds Ia193, in particular to the compounds Ia193.1–Ia193.64 which differ from compounds Ia1.1–Ia1.64 in that $R^2$ is ethylsulfonyl and $R^3$ is methyl.

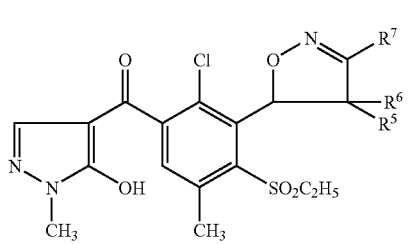

Ia193

Particular preference is likewise given to the compounds Ia194, in particular to the compounds Ia194.1–Ia194.64 which differ from compounds Ia1.1–Ia1.64 in that $R^2$ is ethylsulfonyl, $R^3$ is methyl and $R^{13}$ is ethyl.

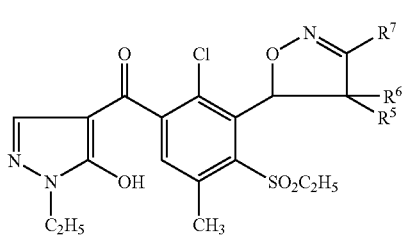

Ia194

Particular preference is likewise given to the compounds Ia195, in particular to the compounds Ia195.1–Ia195.64 which differ from compounds Ia1.1–Ia1.64 in that $R^2$ is ethylsulfonyl, $R^3$ is methyl and $R^{13}$ is isopropyl.

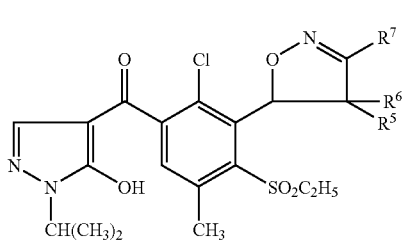

Ia195

Particular preference is likewise given to the compounds Ia196, in particular to the compounds Ia196.1–Ia196.64 which differ from compounds Ia1.1–Ia1.64 in that $R^2$ is ethylsulfonyl, $R^3$ is methyl and $R^{13}$ is tert-butyl.

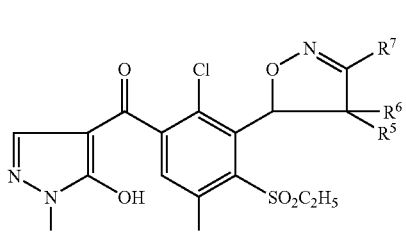

Ia196

Particular preference is likewise given to the compounds Ia97, in particular to the compounds Ia197.1–Ia197.64 which differ from compounds Ia1.1–Ia1.64 in that $R^2$ is ethylsulfonyl, $R^3$ is methyl and $R^{14}$ is methyl.

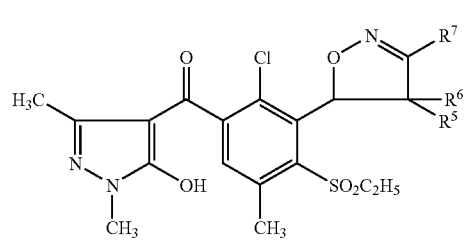

Ia197

Particular preference is likewise given to the compounds Ia198, in particular to the compounds Ia198.1–Ia198.64 which differ from compounds Ia1.1–Ia1.64 in that $R^2$ is ethylsulfonyl, $R^3$ is methyl and $R^{13}$ is ethyl and $R^{14}$ is methyl.

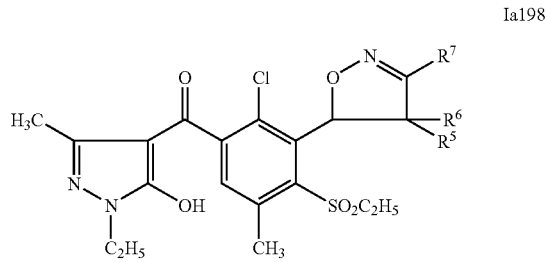

Ia198

Particular preference is likewise given to the compounds Ia199, in particular to the compounds Ia199.1–Ia199.64 which differ from compounds Ia1.1–Ia1.64 in that $R^2$ is ethylsulfonyl, $R^3$ is methyl, $R^{13}$ is isopropyl and $R^{14}$ is methyl.

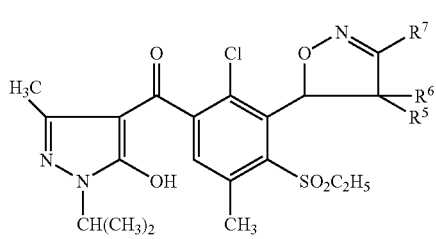

Ia199

Particular preference is likewise given to the compounds Ia200, in particular to the compounds Ia200.1–Ia200.64 which differ from compounds Ia1.1–Ia1.64 in that $R^2$ is ethylsulfonyl, $R^3$ is methyl, $R^{13}$ is tert-butyl and $R^{14}$ is methyl.

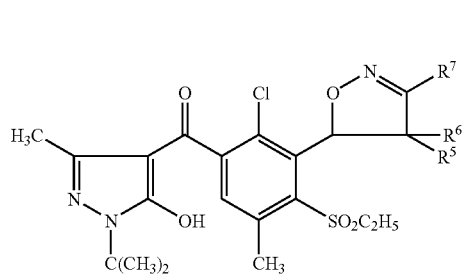

Ia200

Particular preference is likewise given to the compounds Ia201, in particular to the compounds Ia201.1–Ia201.64 which differ from compounds Ia1.1–Ia1.64 in that $R^1$ and $R^3$ are methyl and $R^2$ is ethylsulfonyl.

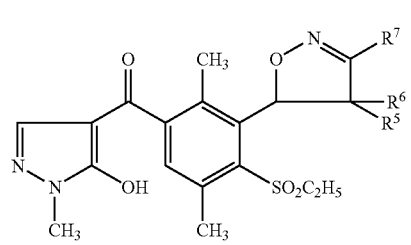

Ia201

Particular preference is likewise given to the compounds Ia202, in particular to the compounds Ia202.1–Ia202.64 which differ from compounds Ia1.1–Ia1.64 in that $R^1$ and $R^3$ are methyl, $R^2$ is ethylsulfonyl and $R^{13}$ is ethyl.

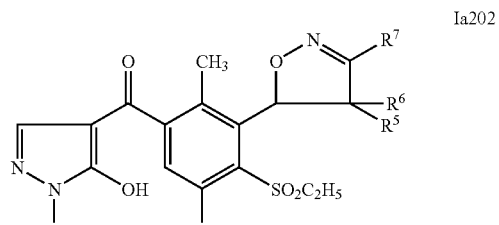

Ia202

Particular preference is likewise given to the compounds Ia203, in particular to the compounds Ia203.1–Ia203.64 which differ from compounds Ia1.1–Ia1.64 in that $R^1$ and $R^3$ are methyl, $R^2$ is ethylsulfonyl and $R^{13}$ is isopropyl.

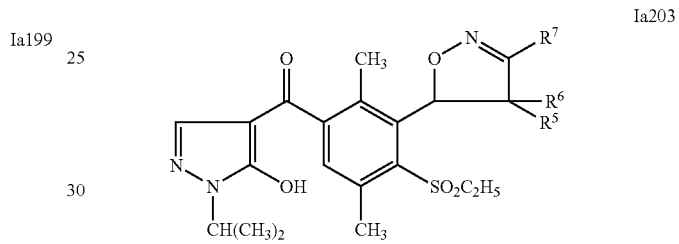

Ia203

Particular preference is likewise given to the compounds Ia204, in particular to the compounds Ia204.1–Ia204.64 which differ from compounds Ia1.1–Ia1.64 in that $R^1$ and $R^3$ are methyl, $R^2$ is ethylsulfonyl and $R^{13}$ is tert-butyl.

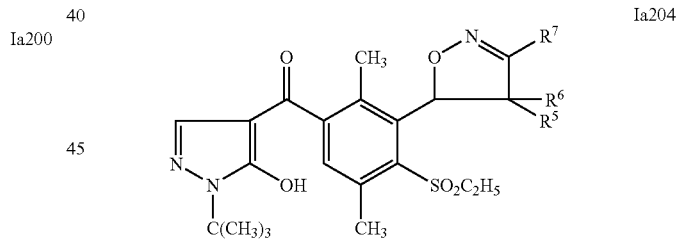

Ia204

Particular preference is likewise given to the compounds Ia205, in particular to the compounds Ia205.1–Ia205.64 which differ from compounds Ia1.1–Ia1.64 in that $R^1$, $R^3$ and $R^{14}$ are methyl and $R^2$ is ethylsulfonyl.

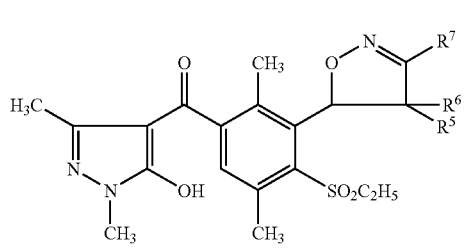

Ia205

Particular preference is likewise given to the compounds Ia206, in particular to the compounds Ia206.1–Ia206.64 which differ from compounds Ia1.1–Ia1.64 in that $R^1$, $R^3$ and $R^{14}$ are methyl, $R^2$ is ethylsulfonyl and $R^{13}$ is ethyl.

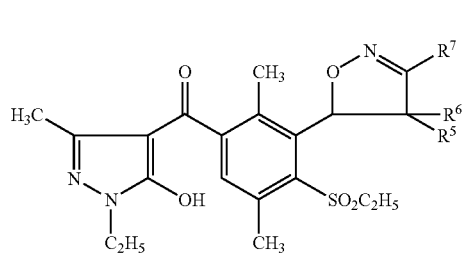
Ia206

Particular preference is likewise given to the compounds Ia207, in particular to the compounds Ia207.1–Ia207.64 which differ from compounds Ia1.1–Ia1.64 in that $R^1$, $R^3$ and $R^{14}$ are methyl, $R^2$ is ethylsulfonyl and $R^{13}$ is isopropyl.

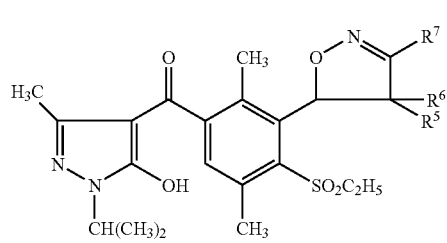
Ia207

Particular preference is likewise given to the compounds Ia208, in particular to the compounds Ia208.1–Ia208.64 which differ from compounds Ia1.1–Ia1.64 in that $R^1$, $R^3$ and $R^{14}$ are methyl, $R^2$ is ethylsulfonyl and $R^{13}$ is tert-butyl.

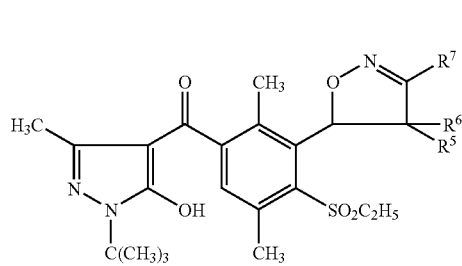
Ia208

Particular preference is likewise given to the compounds Ia209, in particular to the compounds Ia209.1–Ia209.64 which differ from compounds Ia1.1–Ia1.64 in that $R^2$ is chlorine and $R^3$ is methyl.

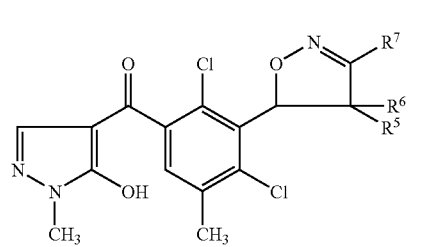
Ia209

Particular preference is likewise given to the compounds Ia210, in particular to the compounds Ia210.1–Ia210.64 which differ from compounds Ia1.1–Ia1.64 in that $R^2$ is chlorine, $R^3$ is methyl and $R^{13}$ is ethyl.

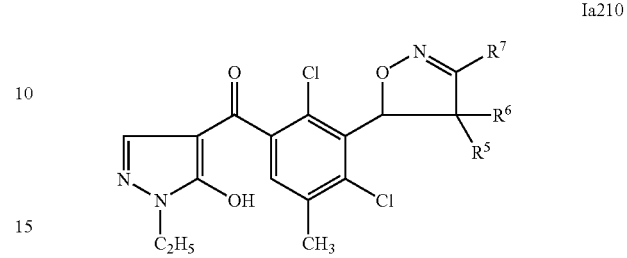
Ia210

Particular preference is likewise given to the compounds Ia211, in particular to the compounds Ia211.1–Ia211.64 which differ from compounds Ia1.1–Ia1.64 in that $R^2$ is chlorine, $R^3$ is methyl and $R^{13}$ is isopropyl.

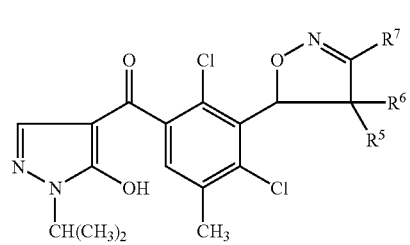
Ia211

Particular preference is likewise given to the compounds Ia212, in particular to the compounds Ia212.1–Ia212.64 which differ from compounds Ia1.1–Ia1.64 in that $R^2$ is chlorine, $R^3$ is methyl and $R^{13}$ is tert-butyl.

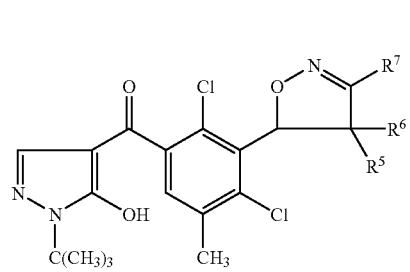
Ia212

Particular preference is likewise given to the compounds Ia213, in particular to the compounds Ia213.1–Ia213.64 which differ from compounds Ia1.1–Ia1.64 in that $R^2$ is chlorine, $R^3$ is methyl and $R^{14}$ is methyl.

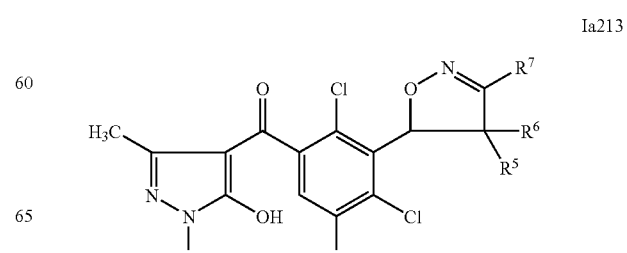
Ia213

Particular preference is likewise given to the compounds Ia214, in particular to the compounds Ia214.1–Ia214.64 which differ from compounds Ia1.1–Ia1.64 in that $R^2$ is chlorine, $R^3$ is methyl, $R^{13}$ is ethyl and $R^{14}$ is methyl.

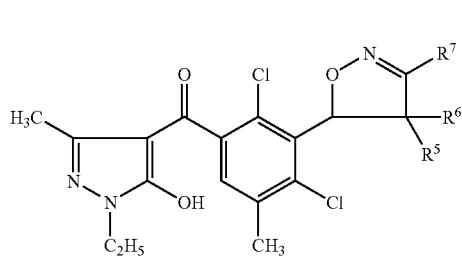

Ia214

Particular preference is likewise given to the compounds Ia215, in particular to the compounds Ia215.1–Ia215.64 which differ from compounds Ia1.1–Ia1.64 in that $R^2$ is chlorine, $R^3$ is methyl, $R^{13}$ is isopropyl and $R^{14}$ is methyl.

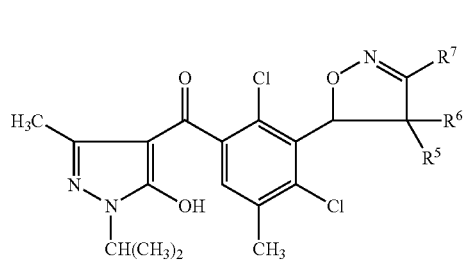

Ia215

Particular preference is likewise given to the compounds Ia216, in particular to the compounds Ia216.1–Ia216.64 which differ from compounds Ia1.1–Ia1.64 in that $R^2$ is chlorine, $R^3$ is methyl, $R^{13}$ is tert-butyl and $R^{14}$ is methyl.

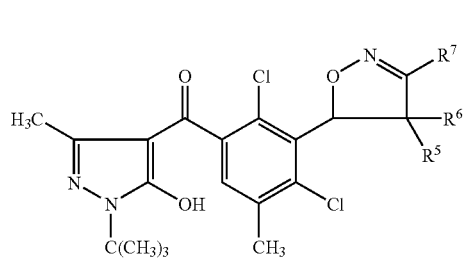

Ia216

Particular preference is likewise given to the compounds Ia217, in particular to the compounds Ia217.1–Ia217.64 which differ from compounds Ia1.1–Ia1.64 in that $R^1$ and $R^3$ are methyl and $R^2$ is chlorine.

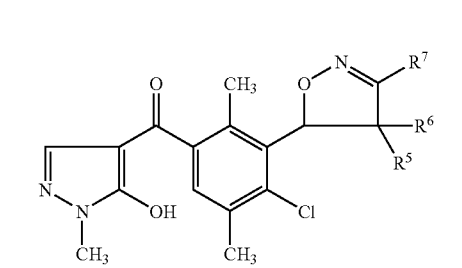

Ia217

Particular preference is likewise given to the compounds Ia218, in particular to the compounds Ia218.1–Ia218.64 which differ from compounds Ia1.1–Ia1.64 in that $R^1$ and $R^3$ are methyl, $R^2$ is chlorine and $R^{13}$ is ethyl.

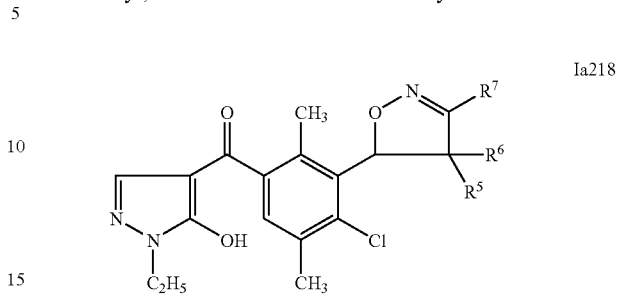

Ia218

Particular preference is likewise given to the compounds Ia219, in particular to the compounds Ia219.1–Ia219.64 which differ from compounds Ia1.1–Ia1.64 in that $R^1$ and $R^3$ are methyl, $R^2$ is chlorine and $R^{13}$ is isopropyl.

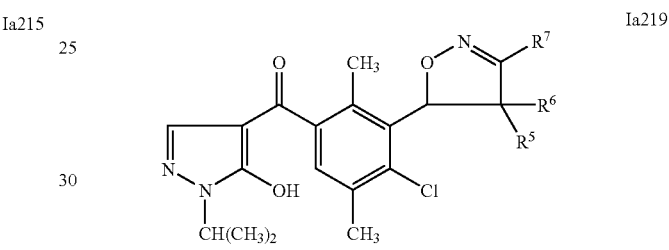

Ia219

Particular preference is likewise given to the compounds Ia220, in particular to the compounds Ia220.1–Ia220.64 which differ from compounds Ia1.1–Ia1.64 in that $R^1$ and $R^3$ are methyl, $R^2$ is chlorine and $R^{13}$ is tert-butyl.

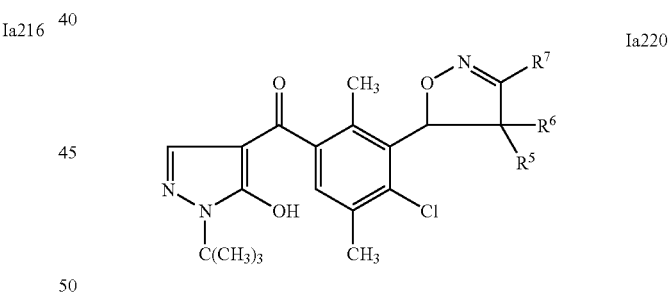

Ia220

Particular preference is likewise given to the compounds Ia221, in particular to the compounds Ia221.1–Ia221.64 which differ from compounds Ia1.1–Ia1.64 in that $R^1$, $R^3$ and $R^{14}$ are methyl and $R^2$ is chlorine.

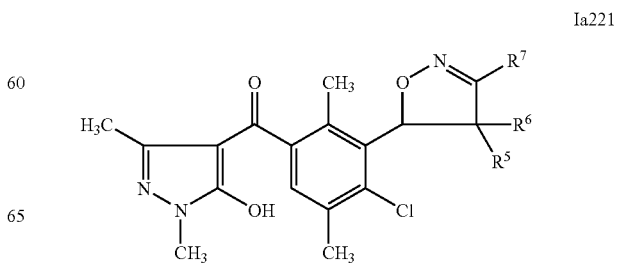

Ia221

Particular preference is likewise given to the compounds Ia222, in particular to the compounds Ia222.1–Ia222.64 which differ from compounds Ia1.1–Ia1.64 in that $R^1$, $R^3$ and $R^{14}$ are methyl, $R^2$ is chlorine and $R^{13}$ is ethyl.

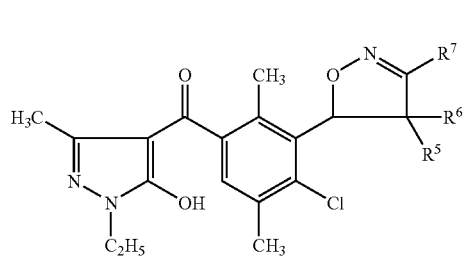

Ia222

Particular preference is likewise given to the compounds Ia223, in particular to the compounds Ia223.1–Ia223.64 which differ from compounds Ia1.1–Ia1.64 in that $R^1$, $R^3$ and $R^{14}$ are methyl, $R^2$ is chlorine and $R^{13}$ is isopropyl.

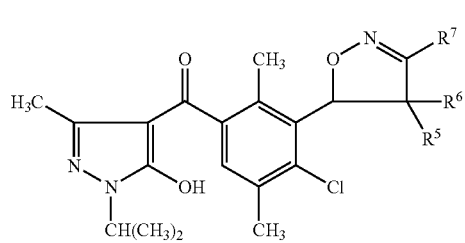

Ia223

Particular preference is likewise given to the compounds Ia224, in particular to the compounds Ia224.1–Ia224.64 which differ from compounds Ia1.1–Ia1.64 in that $R^1$, $R^3$ and $R^{14}$ are methyl, $R^2$ is chlorine and $R^{13}$ is tert-butyl.

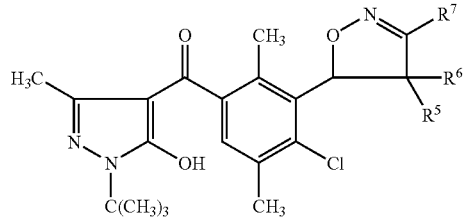

Ia224

Particular preference is likewise given to the compounds Ia225, in particular to the compounds Ia225.1–Ia225.64 which differ from compounds Ia1.1–Ia1.64 in that $R^{12}$ is methylsulfonyl.

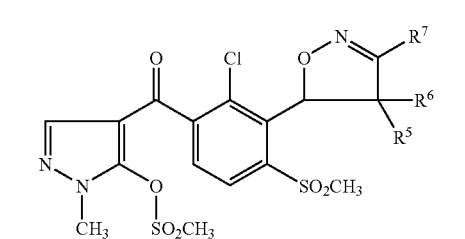

Ia225

Particular preference is likewise given to the compounds Ia226, in particular to the compounds Ia226.1–Ia226.64 which differ from compounds Ia1.1–Ia1.64 in that $R^{12}$ is methylsulfonyl and $R^{13}$ is ethyl.

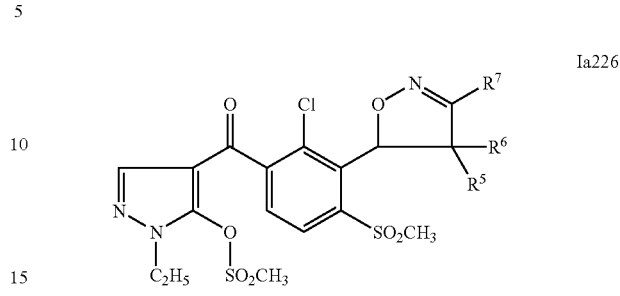

Ia226

Particular preference is likewise given to the compounds Ia227, in particular to the compounds Ia227.1–Ia227.64 which differ from compounds Ia1.1–Ia1.64 in that $R^{12}$ is methylsulfonyl and $R^{13}$ is isopropyl.

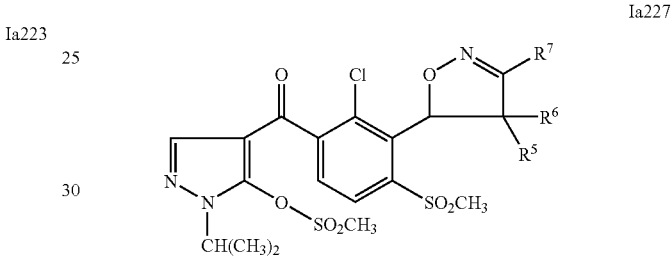

Ia227

Particular preference is likewise given to the compounds Ia228, in particular to the compounds Ia228.1–Ia228.64 which differ from compounds Ia1.1–Ia1.64 in that $R^{12}$ is methylsulfonyl and $R^{13}$ is tert-butyl.

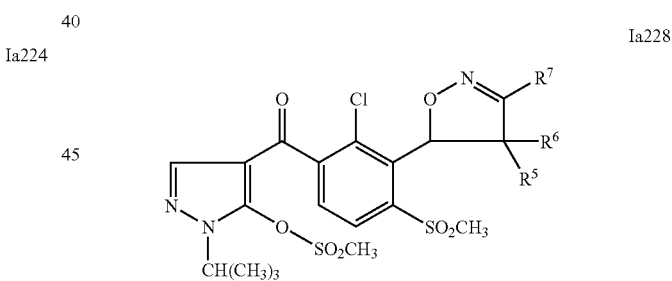

Ia228

Particular preference is likewise given to the compounds Ia229, in particular to the compounds Ia229.1–Ia229.64 which differ from compounds Ia1.1–Ia1.64 in that $R^{12}$ is methylsulfonyl and $R^{14}$ is methyl.

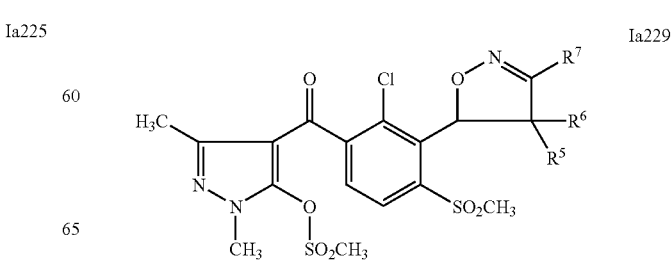

Ia229

Particular preference is likewise given to the compounds Ia230, in particular to the compounds Ia230.1–Ia230.64 which differ from compounds Ia1.1–Ia1.64 in that $R^{12}$ is methylsulfonyl, $R^{13}$ is ethyl and $R^{14}$ is methyl.

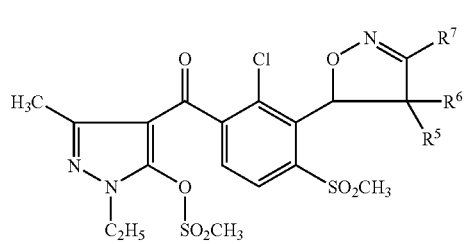

Ia230

Particular preference is likewise given to the compounds Ia231, in particular to the compounds Ia231.1–Ia231.64 which differ from compounds Ia1.1–Ia1.64 in that $R^{12}$ is methylsulfonyl, $R^{13}$ is isopropyl and $R^{14}$ is methyl.

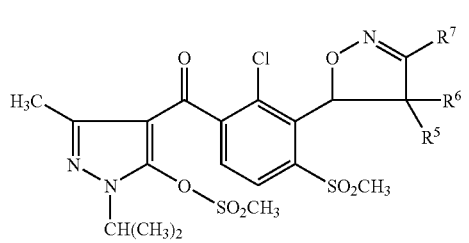

Ia231

Particular preference is likewise given to the compounds Ia232, in particular to the compounds Ia232.1–Ia232.64 which differ from compounds Ia1.1–Ia1.64 in that $R^{12}$ is methylsulfonyl, $R^{13}$ is tert-butyl and $R^{14}$ is methyl.

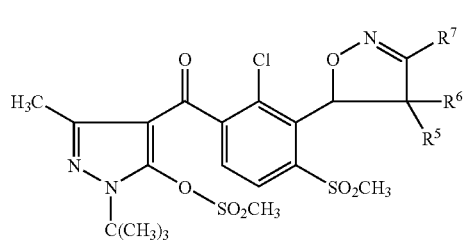

Ia232

Particular preference is likewise given to the compounds Ia233, in particular to the compounds Ia233.1–Ia233.64 which differ from compounds Ia1.1–Ia1.64 in that $R^1$ is methyl and $R^{12}$ is methylsulfonyl.

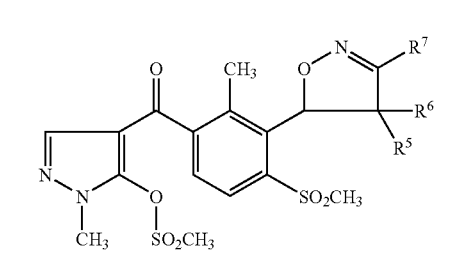

Ia233

Particular preference is likewise given to the compounds Ia234, in particular to the compounds Ia234.1–Ia234.64 which differ from compounds Ia1.1–Ia1.64 in that $R^1$ is methyl, $R^{12}$ is methylsulfonyl and $R^{13}$ is ethyl.

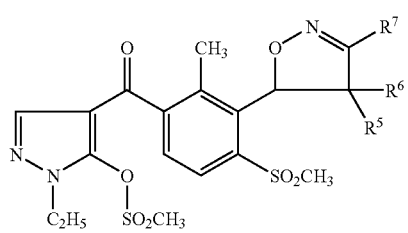

Ia234

Particular preference is likewise given to the compounds Ia235, in particular to the compounds Ia235.1–Ia235.64 which differ from compounds Ia1.1–Ia1.64 in that $R^1$ is methyl, $R^{12}$ is methylsulfonyl and $R^{13}$ is isopropyl.

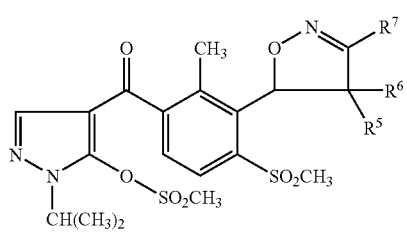

Ia235

Particular preference is likewise given to the compounds Ia236, in particular to the compounds Ia236.1–Ia236.64 which differ from compounds Ia1.1–Ia1.64 in that $R^1$ is methyl, $R^{12}$ is methylsulfonyl and $R^{13}$ is tert-butyl.

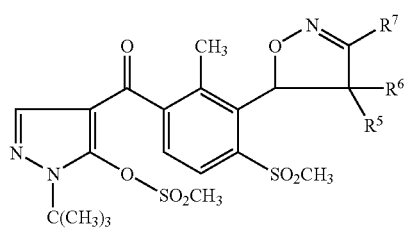

Ia236

Particular preference is likewise given to the compounds Ia237, in particular to the compounds Ia237.1–Ia273.64 [sic] which differ from compounds Ia1.1–Ia1.64 in that $R^1$ and $R^{14}$ are methyl and $R^{12}$ is methylsulfonyl.

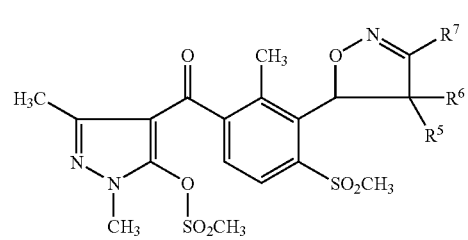

Ia237

Particular preference is likewise given to the compounds Ia238, in particular to the compounds Ia238.1–Ia238.64 which differ from compounds Ia1.1–Ia1.64 in that $R^1$ and $R^{14}$ are methyl, $R^{12}$ is methylsulfonyl and $R^{13}$ is ethyl.

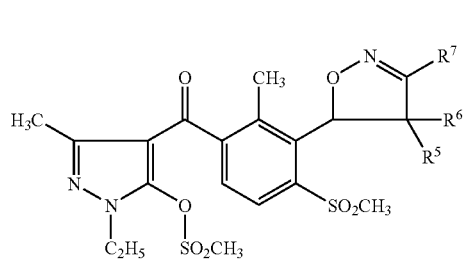

Ia238

Particular preference is likewise given to the compounds Ia239, in particular to the compounds Ia239.1–Ia239.64 which differ from compounds Ia1.1–Ia1.64 in that $R^1$ and $R^{14}$ are methyl, $R^{12}$ is methylsulfonyl and $R^{13}$ is isopropyl.

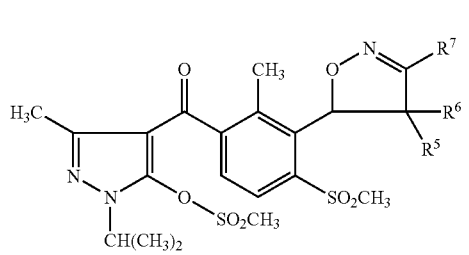

Ia239

Particular preference is likewise given to the compounds Ia240, in particular to the compounds Ia240.1–Ia240.64 which differ from compounds Ia1.1–Ia1.64 in that $R^1$ and $R^{14}$ are methyl, $R^{12}$ is methylsulfonyl and $R^{13}$ is tert-butyl.

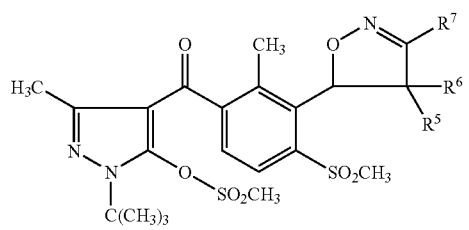

Ia240

Particular preference is likewise given to the compounds Ia241, in particular to the compounds Ia241.1–Ia241.64 which differ from compounds Ia1.1–Ia1.64 in that $R^2$ is ethylsulfonyl and $R^{12}$ is methylsulfonyl.

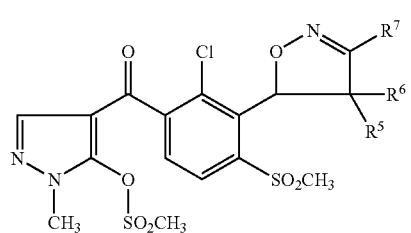

Ia241

Particular preference is likewise given to the compounds Ia242, in particular to the compounds Ia242.1–Ia242.64 which differ from compounds Ia1.1–Ia1.64 in that $R^2$ is ethylsulfonyl, $R^{12}$ is methylsulfonyl and $R^{13}$ is ethyl.

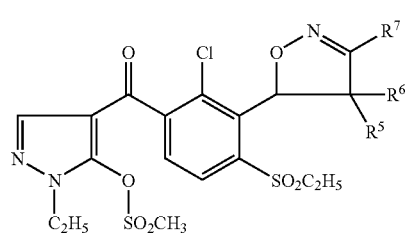

Ia242

Particular preference is likewise given to the compounds Ia243, in particular to the compounds Ia243.1–Ia243.64 which differ from compounds Ia1.1–Ia1.64 in that $R^2$ is ethylsulfonyl, $R^{12}$ is methylsulfonyl and $R^{13}$ is isopropyl.

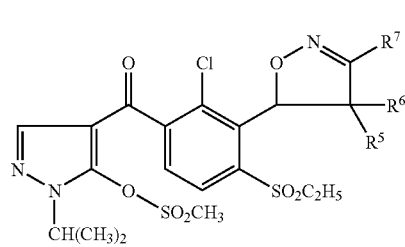

Ia243

Particular preference is likewise given to the compounds Ia244, in particular to the compounds Ia244.1–Ia244.64 which differ from compounds Ia1.1–Ia1.64 in that $R^2$ is ethylsulfonyl, $R^{12}$ is methylsulfonyl and $R^{13}$ is tert-butyl.

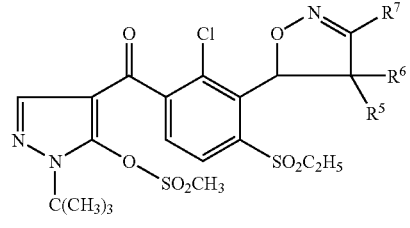

Ia244

Particular preference is likewise given to the compounds Ia245, in particular to the compounds Ia245.1–Ia245.64 which differ from compounds Ia1.1–Ia1.64 in that $R^2$ is ethylsulfonyl, $R^{12}$ is methylsulfonyl and $R^{14}$ is methyl.

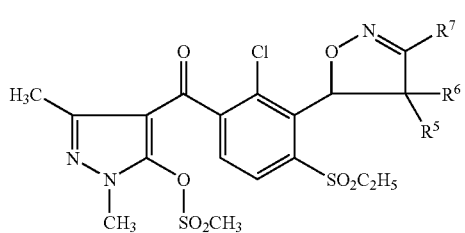

Ia245

Particular preference is likewise given to the compounds Ia246, in particular to the compounds Ia246.1–Ia246.64 which differ from compounds Ia1.1–Ia1.64 in that $R^2$ is ethylsulfonyl, $R^{12}$ is methylsulfonyl, $R^{13}$ is ethyl and $R^{14}$ is methyl.

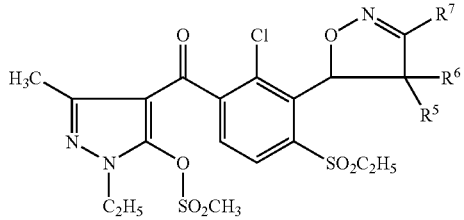

Ia246

Particular preference is likewise given to the compounds Ia247, in particular to the compounds Ia247.1–Ia247.64 which differ from compounds Ia1.1–Ia1.64 in that $R^2$ is ethylsulfonyl, $R^{12}$ is methylsulfonyl, $R^{13}$ is isopropyl and $R^{14}$ is methyl.

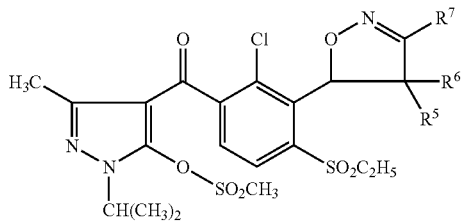

Ia247

Particular preference is likewise given to the compounds Ia248, in particular to the compounds Ia248.1–Ia248.64 which differ from compounds Ia1.1–Ia1.64 in that $R^2$ is ethylsulfonyl, $R^{12}$ is ethylsulfonyl, $R^{13}$ is tert-butyl and $R^{14}$ is methyl.

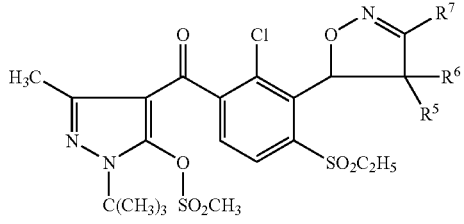

Ia248

Particular preference is likewise given to the compounds Ia249, in particular to the compounds Ia249.1–Ia249.64 which differ from compounds Ia1.1–Ia1.64 in that $R^1$ is methyl, $R^2$ is ethylsulfonyl and $R^{12}$ is methylsulfonyl.

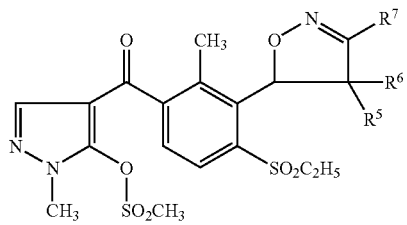

Ia249

Particular preference is likewise given to the compounds Ia250, in particular to the compounds Ia250.1–Ia250.64 which differ from compounds Ia1.1–Ia1.64 in that $R^1$ is methyl, $R^2$ is ethylsulfonyl, $R^{12}$ is methylsulfonyl and $R^{13}$ is ethyl.

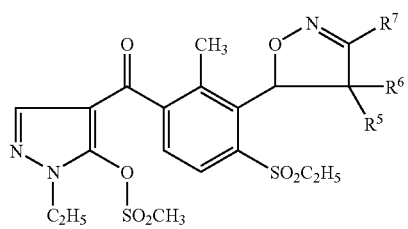

Ia250

Particular preference is likewise given to the compounds Ia251, in particular to the compounds Ia251.1–Ia251.64 which differ from compounds Ia1.1–Ia1.64 in that $R^1$ is methyl, $R^2$ is ethylsulfonyl, $R^{12}$ is methylsulfonyl and $R^{13}$ is isopropyl.

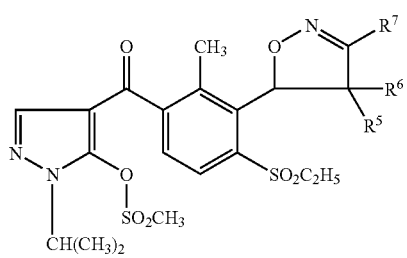

Ia251

Particular preference is likewise given to the compounds Ia252, in particular to the compounds Ia252.1–Ia252.64 which differ from compounds Ia1.1–Ia1.64 in that $R^1$ is methyl, $R^2$ is ethylsulfonyl, $R^{12}$ is methylsulfonyl and $R^{13}$ is tert-butyl.

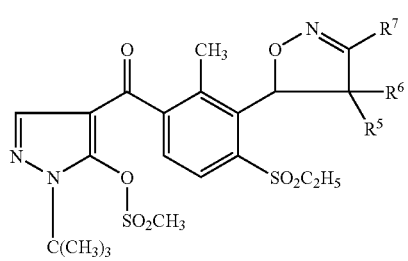

Ia252

Particular preference is likewise given to the compounds Ia253, in particular to the compounds Ia253.1–Ia253.64 which differ from compounds Ia1.1–Ia1.64 in that $R^1$ and $R^{14}$ are methyl, $R^2$ is ethylsulfonyl and $R^{12}$ is methylsulfonyl.

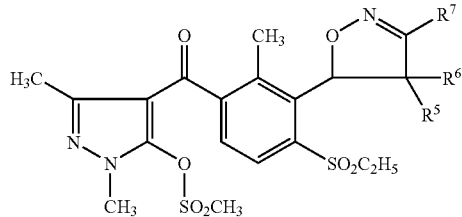

Ia254

Particular preference is likewise given to the compounds Ia254, in particular to the compounds Ia254.1–Ia254.64 which differ from compounds Ia1.1–Ia1.64 in that $R^1$ and $R^{14}$ are methyl, $R^2$ is ethylsulfonyl, $R^{12}$ is methylsulfonyl and $R^{13}$ is ethyl.

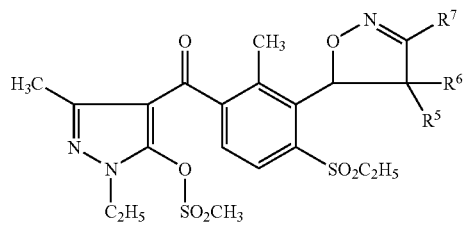

Ia254

Particular preference is likewise given to the compounds Ia255, in particular to the compounds Ia255.1–Ia255.64 which differ from compounds Ia1.1–Ia1.64 in that $R^1$ and $R^{14}$ are methyl, $R^2$ is ethylsulfonyl, $R^{12}$ is methylsulfonyl and $R^{13}$ is isopropyl.

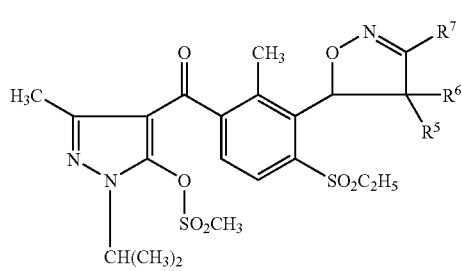

Ia255

Particular preference is likewise given to the compounds Ia256, in particular to the compounds Ia256.1–Ia256.64 which differ from compounds Ia1.1–Ia1.64 in that $R^1$ and $R^{14}$ are methyl, $R^2$ is ethylsulfonyl, $R^{12}$ is methylsulfonyl and $R^{14}$ is tert-butyl.

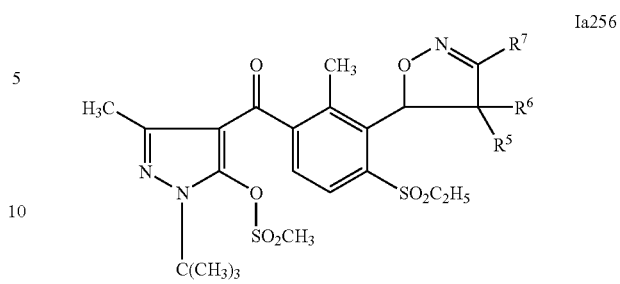

Ia256

Particular preference is likewise given to the compounds Ia257, in particular to the compounds Ia257.1–Ia257.64 which differ from compounds Ia1.1–Ia1.64 in that $R^2$ is chlorine and $R^{12}$ is ethylsulfonyl.

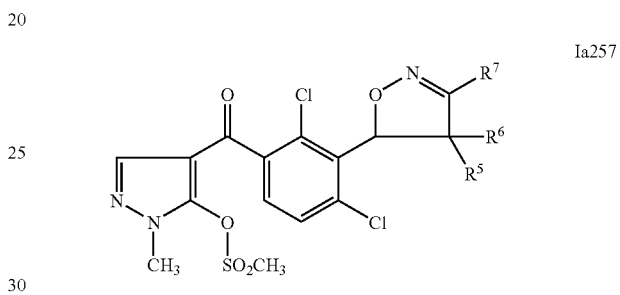

Ia257

Particular preference is likewise given to the compounds Ia258, in particular to the compounds Ia258.1–Ia258.64 which differ from compounds Ia1.1–Ia1.64 in that $R^2$ is chlorine, $R^{12}$ is methylsulfonyl and $R^{13}$ is ethyl.

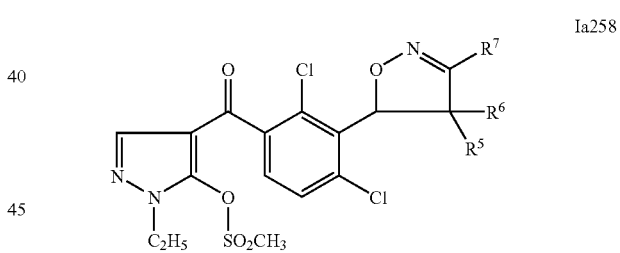

Ia258

Particular preference is likewise given to the compounds Ia259, in particular to the compounds Ia259.1–Ia259.64 which differ from compounds Ia1.1–Ia1.64 in that $R^2$ is chlorine, $R^{12}$ is methylsulfonyl and $R^{13}$ is isopropyl.

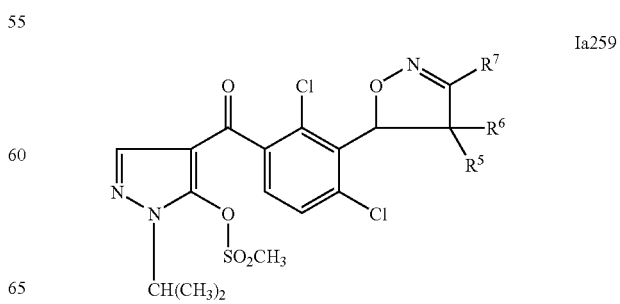

Ia259

Particular preference is likewise given to the compounds Ia260, in particular to the compounds Ia260.1–Ia260.64 which differ from compounds Ia1.1–Ia1.64 in that $R^2$ is chlorine, $R^{12}$ is methylsulfonyl and $R^{13}$ is tert-butyl.

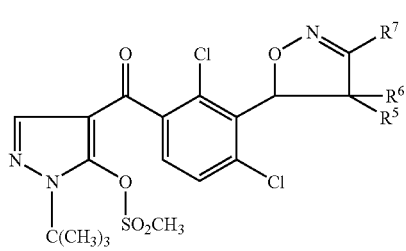

Ia260

Particular preference is likewise given to the compounds Ia261, in particular to the compounds Ia261.1–Ia261.64 which differ from compounds Ia1.1–Ia1.64 in that $R^2$ is chlorine, $R^{12}$ is methylsulfonyl and $R^{13}$ is methyl.

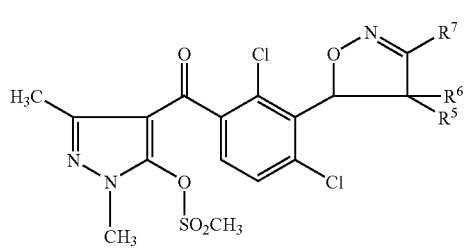

Ia261

Particular preference is likewise given to the compounds Ia262, in particular to the compounds Ia262.1–Ia262.64 which differ from compounds Ia1.1–Ia1.64 in that $R^2$ is chlorine, $R^{12}$ is methylsulfonyl, $R^{13}$ is ethyl and $R^{14}$ is methyl.

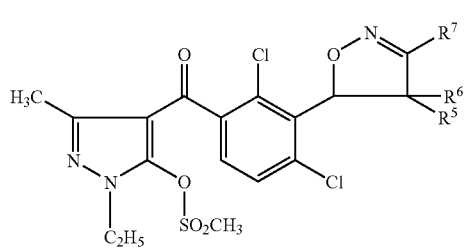

Ia262

Particular preference is likewise given to the compounds Ia263, in particular to the compounds Ia263.1–Ia263.64 which differ from compounds Ia1.1–Ia1.64 in that $R^2$ is chlorine, $R^{12}$ is methylsulfonyl, $R^{13}$ is isopropyl and $R^{14}$ is methyl.

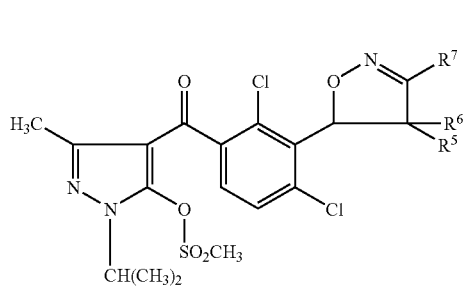

Ia263

Particular preference is likewise given to the compounds Ia264, in particular to the compounds Ia264.1–Ia264.64 which differ from compounds Ia1.1–Ia1.64 in that $R^2$ is chlorine, $R^{12}$ is methylsulfonyl, $R^{13}$ is tert-butyl and $R^{14}$ is methyl.

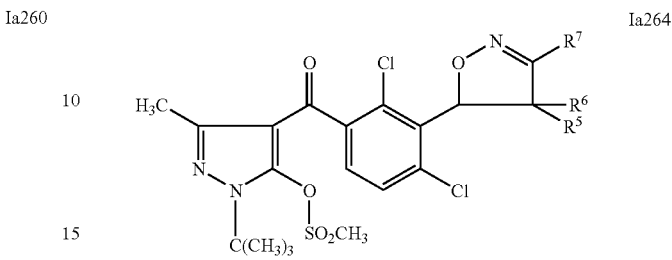

Ia264

Particular preference is likewise given to the compounds Ia265, in particular to the compounds Ia265.1–Ia265.64 which differ from compounds Ia1.1–Ia1.64 in that $R^1$ is methyl, $R^2$ is chlorine and $R^{12}$ is methylsulfonyl.

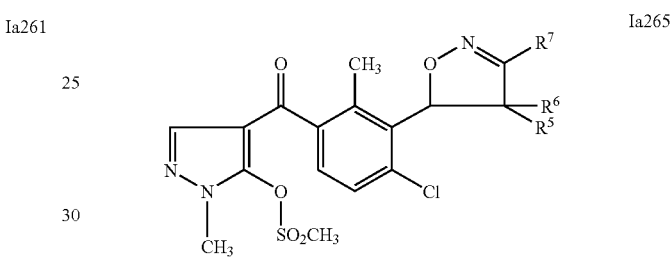

Ia265

Particular preference is likewise given to the compounds Ia266, in particular to the compounds Ia266.1–Ia266.64 which differ from compounds Ia1.1–Ia1.64 in that $R^1$ is methyl, $R^2$ is chlorine, $R^{12}$ is methylsulfonyl and $R^{13}$ is ethyl.

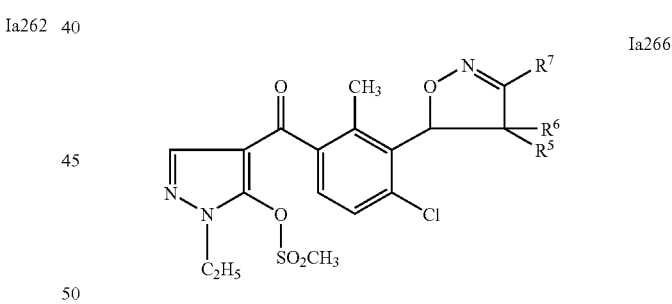

Ia266

Particular preference is likewise given to the compounds Ia267, in particular to the compounds Ia267.1–Ia267.64 which differ from compounds Ia1.1–Ia1.64 in that $R^1$ is methyl, $R^2$ is chlorine, $R^{12}$ is methylsulfonyl and $R^{13}$ is isopropyl.

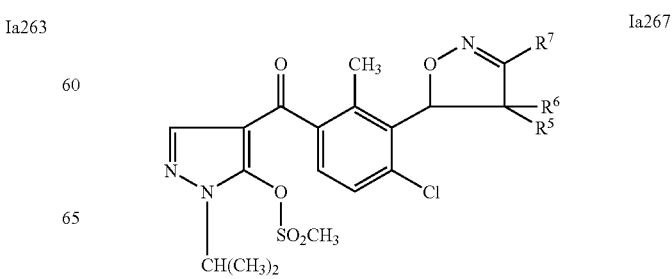

Ia267

Particular preference is likewise given to the compounds Ia268, in particular to the compounds Ia268.1–Ia268.64 which differ from compounds Ia1.1–Ia1.64 in that $R^1$ is methyl, $R^2$ is chlorine, $R^{12}$ is methylsulfonyl and $R^{13}$ is tert-butyl.

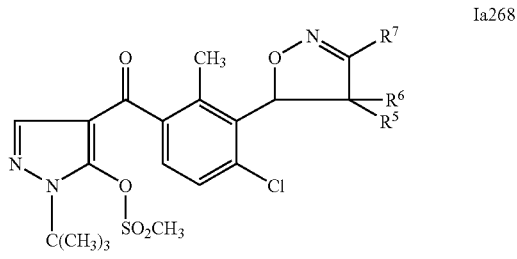

Ia268

Particular preference is likewise given to the compounds Ia269, in particular to the compounds Ia269.1–Ia269.64 which differ from compounds Ia1.1–Ia1.64 in that $R^1$ and $R^{14}$ are methyl, $R^2$ is chlorine and $R^{12}$ is methylsulfonyl.

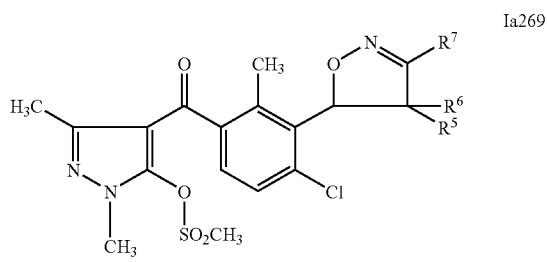

Ia269

Particular preference is likewise given to the compounds Ia270, in particular to the compounds Ia270.1–Ia270.64 which differ from compounds Ia1.1–Ia1.64 in that $R^1$ and $R^{14}$ are methyl, $R^2$ is chlorine, $R^{12}$ is methylsulfonyl and $R^{13}$ is ethyl.

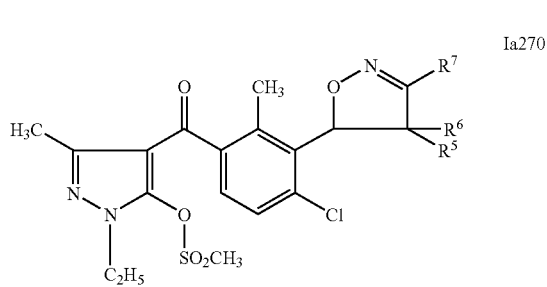

Ia270

Particular preference is likewise given to the compounds Ia271, in particular to the compounds Ia271.1–Ia271.64 which differ from compounds Ia1.1–Ia1.64 in that $R^1$ and $R^{14}$ are methyl, $R^2$ is chlorine, $R^{12}$ is methylsulfonyl and $R^{13}$ is isopropyl.

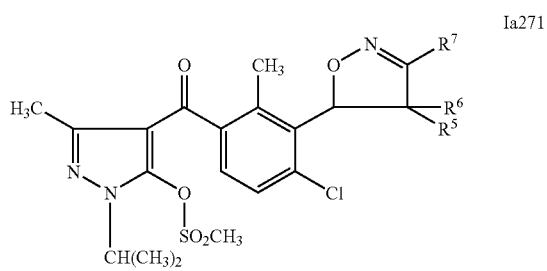

Ia271

Particular preference is likewise given to the compounds Ia272, in particular to the compounds Ia272.1–Ia272.64 which differ from compounds Ia1.1–Ia1.64 in that $R^1$ and $R^{14}$ are methyl, $R^2$ is chlorine, $R^3$ is methylsulfonyl and $R^{13}$ is tert-butyl.

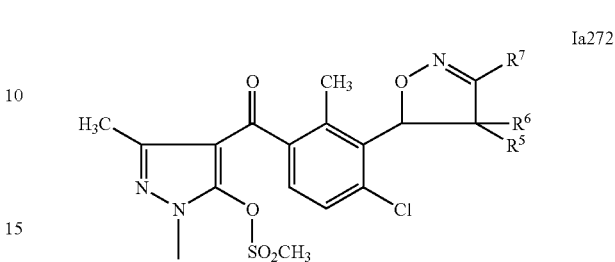

Ia272

Particular preference is likewise given to the compounds Ia273, in particular to the compounds Ia273.1–Ia273.64 which differ from compounds Ia1.1–Ia1.64 in that $R^{12}$ is phenylsulfonyl.

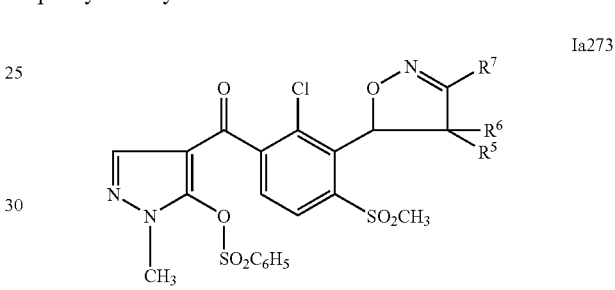

Ia273

Particular preference is likewise given to the compounds Ia274, in particular to the compounds Ia274.1–Ia274.64 which differ from compounds Ia1.1–Ia1.64 in that $R^{12}$ is phenylsulfonyl and $R^{13}$ is ethyl.

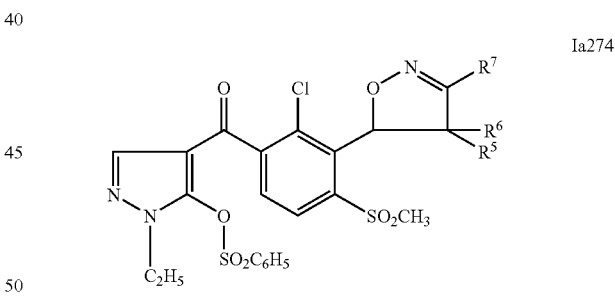

Ia274

Particular preference is likewise given to the compounds Ia275, in particular to the compounds Ia275.1–Ia275.64 which differ from compounds Ia1.1–Ia1.64 in that $R^{12}$ is phenylsulfonyl and $R^{13}$ is isopropyl.

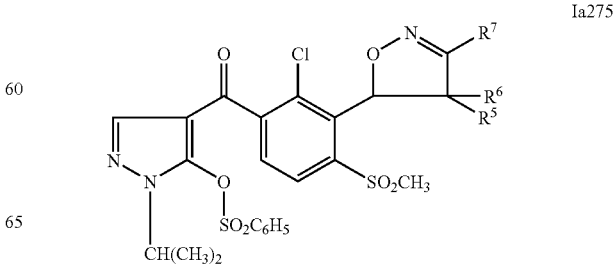

Ia275

Particular preference is likewise given to the compounds Ia276, in particular to the compounds Ia276.1–Ia276.64 which differ from compounds Ia1.1–Ia1.64 in that $R^{12}$ is phenylsulfonyl and $R^{13}$ is tert-butyl.

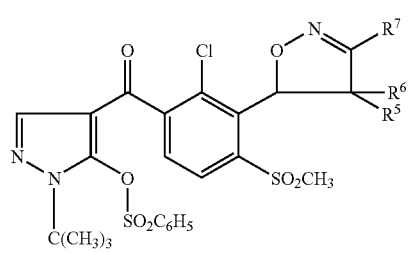

Ia276

Particular preference is likewise given to the compounds Ia277, in particular to the compounds Ia277.1–Ia277.64 which differ from compounds Ia1.1–Ia1.64 in that $R^{12}$ is phenylsulfonyl and $R^{14}$ is methyl.

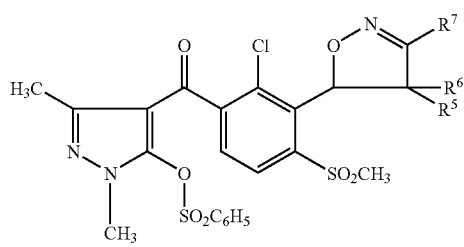

Ia277

Particular preference is likewise given to the compounds Ia278, in particular to the compounds Ia278.1–Ia278.64 which differ from compounds Ia1.1–Ia1.64 in that $R^{12}$ is phenylsulfonyl, $R^{13}$ is ethyl and $R^{14}$ is methyl.

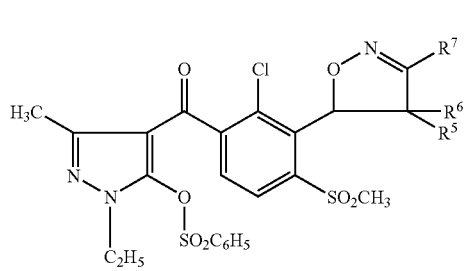

Ia278

Particular preference is likewise given to the compounds Ia279, in particular to the compounds Ia279.1–Ia279.64 which differ from compounds Ia1.1–Ia1.64 in that $R^{12}$ is phenylsulfonyl, $R^{13}$ is isopropyl and $R^{14}$ is methyl.

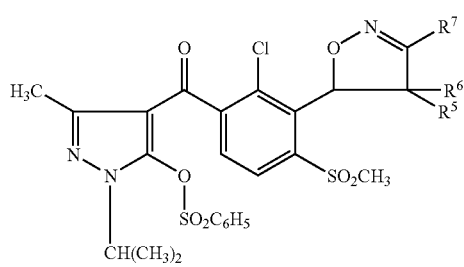

Ia279

Particular preference is likewise given to the compounds Ia280, in particular to the compounds Ia280.1–Ia280.64 which differ from compounds Ia1.1–Ia1.64 in that $R^{12}$ is phenylsulfonyl, $R^{13}$ is tert-butyl and $R^{14}$ is methyl.

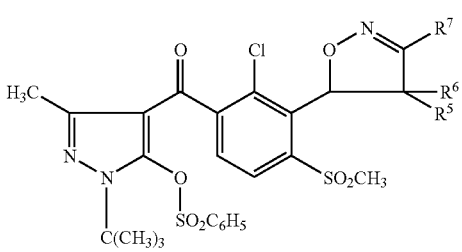

Ia280

Particular preference is likewise given to the compounds Ia281, in particular to the compounds Ia281.1–Ia281.64 which differ from compounds Ia1.1–Ia1.64 in that $R^{1}$ is methyl and $R^{12}$ is phenylsulfonyl.

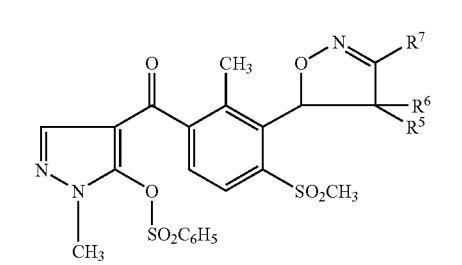

Ia281

Particular preference is likewise given to the compounds Ia282, in particular to the compounds Ia282.1–Ia282.64 which differ from compounds Ia1.1–Ia1.64 in that $R^{1}$ is methyl, $R^{12}$ is phenylsulfonyl and $R^{13}$ is ethyl.

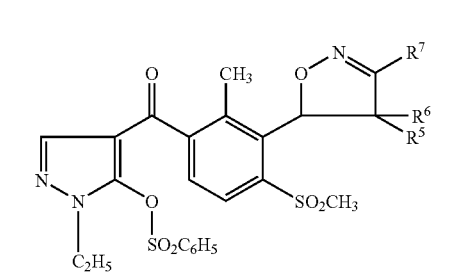

Ia282

Particular preference is likewise given to the compounds Ia283, in particular to the compounds Ia283.1–Ia283.64 which differ from compounds Ia1.1–Ia1.64 in that $R^{1}$ is methyl, $R^{12}$ is phenylsulfonyl and $R^{13}$ is isopropyl.

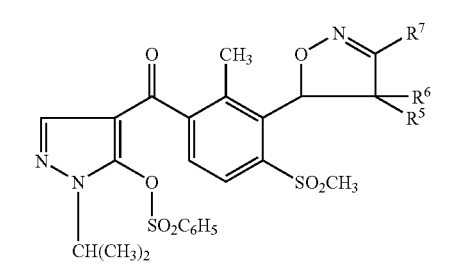

Ia283

Particular preference is likewise given to the compounds Ia284, in particular to the compounds Ia284.1–Ia284.64 which differ from compounds Ia1.1–Ia1.64 in that $R^1$ is methyl, $R^{12}$ is phenylsulfonyl and $R^{13}$ is tert-butyl.

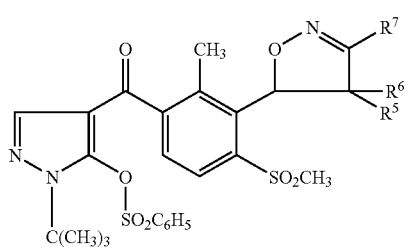
Ia284

Particular preference is likewise given to the compounds Ia285, in particular to the compounds Ia285.1–Ia285.64 which differ from compounds Ia1.1–Ia1.64 in that $R^1$ and $R^{14}$ are methyl and $R^{12}$ is phenylsulfonyl.

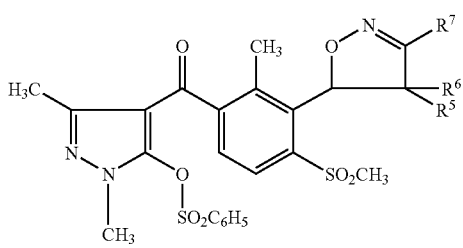
Ia285

Particular preference is likewise given to the compounds Ia286, in particular to the compounds Ia286.1–Ia286.64 which differ from compounds Ia1.1–Ia1.64 in that $R^1$ and $R^{14}$ are methyl, $R^{12}$ is phenylsulfonyl and $R^{13}$ is ethyl.

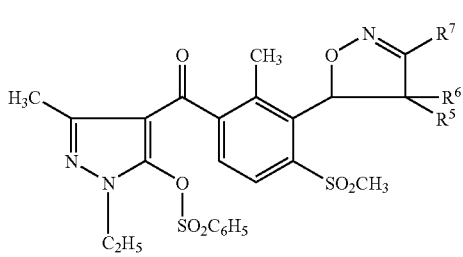
Ia286

Particular preference is likewise given to the compounds Ia287, in particular to the compounds Ia287.1–Ia287.64 which differ from compounds Ia1.1–Ia1.64 in that $R^1$ and $R^{14}$ are methyl, $R^{12}$ is phenylsulfonyl and $R^{13}$ is isopropyl.

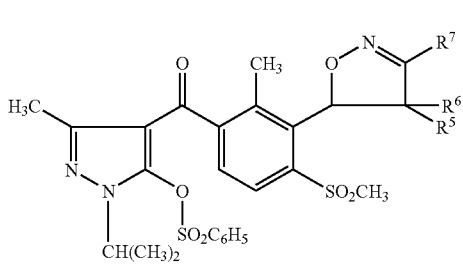
Ia287

Particular preference is likewise given to the compounds Ia288, in particular to the compounds Ia288.1–Ia288.64 which differ from compounds Ia1.1–Ia1.64 in that $R^1$ and $R^{14}$ are methyl, $R^{12}$ is phenylsulfonyl and $R^{13}$ is tert-butyl.

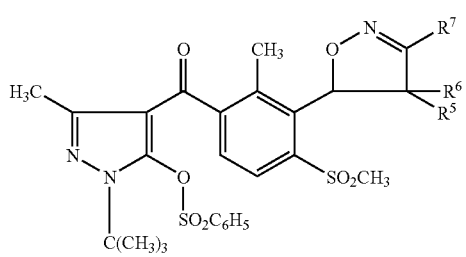
Ia288

Particular preference is likewise given to the compounds Ia289, in particular to the compounds Ia289.1–Ia289.64 which differ from compounds Ia1.1–Ia1.64 in that $R^2$ is ethylsulfonyl and $R^{12}$ is phenylsulfonyl.

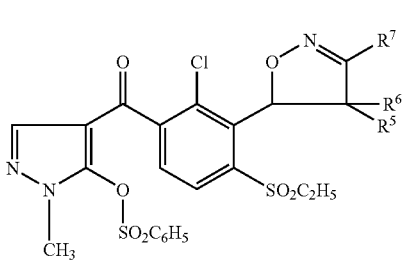
Ia289

Particular preference is likewise given to the compounds Ia290, in particular to the compounds Ia290.1–Ia290.64 which differ from compounds Ia1.1–Ia1.64 in that $R^2$ is ethylsulfonyl, $R^{12}$ is phenylsulfonyl and $R^{13}$ is ethyl.

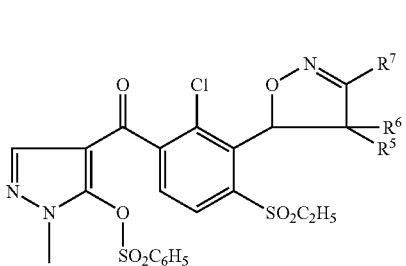
Ia290

Particular preference is likewise given to the compounds Ia291, in particular to the compounds Ia291.1–Ia291.64 which differ from compounds Ia1.1–Ia1.64 in that $R^2$ is ethylsulfonyl, $R^{12}$ is phenylsulfonyl and $R^{13}$ is isopropyl.

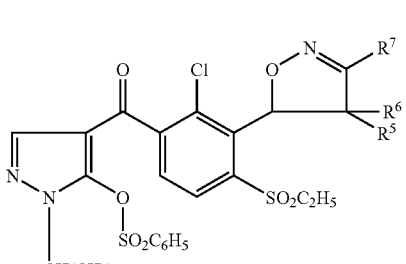
Ia291

Particular preference is likewise given to the compounds Ia292, in particular to the compounds Ia292.1–Ia292.64 which differ from compounds Ia1.1–Ia1.64 in that $R^2$ is ethylsulfonyl, $R^{12}$ is phenylsulfonyl and $R^{13}$ is tert-butyl.

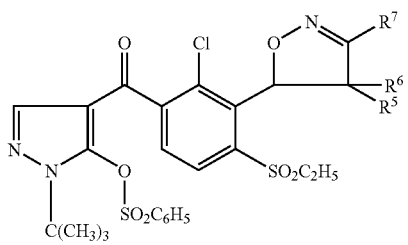

Ia292

Particular preference is likewise given to the compounds Ia293, in particular to the compounds Ia293.1–Ia293.64 which differ from compounds Ia1.1–Ia1.64 in that $R^2$ is ethylsulfonyl, $R^{12}$ is phenylsulfonyl and $R^{14}$ is methyl.

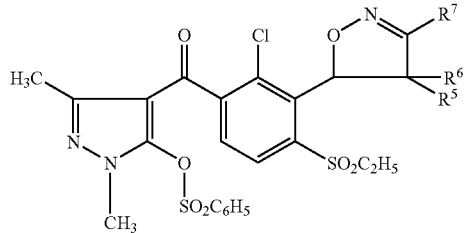

Ia293

Particular preference is likewise given to the compounds Ia294, in particular to the compounds Ia294.1–Ia294.64 which differ from compounds Ia1.1–Ia1.64 in that $R^2$ is ethylsulfonyl, $R^{12}$ is phenylsulfonyl, $R^{13}$ is ethyl and $R^{14}$ is methyl.

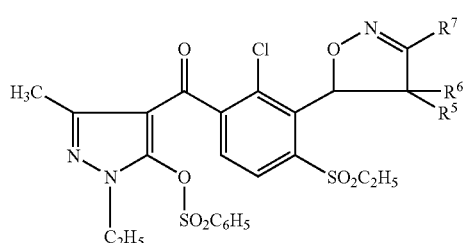

Ia294

Particular preference is likewise given to the compounds Ia295, in particular to the compounds Ia295.1–Ia295.64 which differ from compounds Ia1.1–Ia1.64 in that $R^2$ is ethylsulfonyl, $R^{12}$ is phenylsulfonyl, $R^{13}$ is isopropyl and $R^{14}$ is methyl.

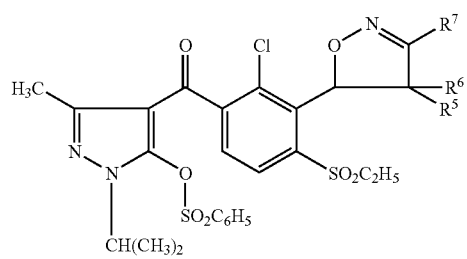

Ia295

Particular preference is likewise given to the compounds Ia296, in particular to the compounds Ia296.1–Ia296.64 which differ from compounds Ia1.1–Ia1.64 in that $R^2$ is ethylsulfonyl, $R^{12}$ is phenylsulfonyl, $R^{13}$ is tert-butyl and $R^{14}$ is methyl.

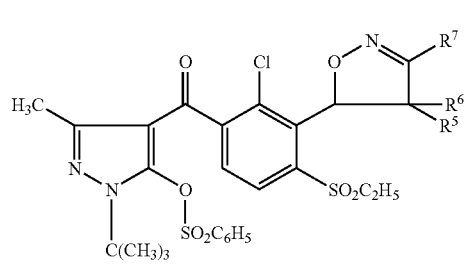

Ia296

Particular preference is likewise given to the compounds Ia297, in particular to the compounds Ia297.1–Ia297.64 which differ from compounds Ia1.1–Ia1.64 in that $R^1$ is methyl, $R^2$ is ethylsulfonyl and $R^{12}$ is phenylsulfonyl.

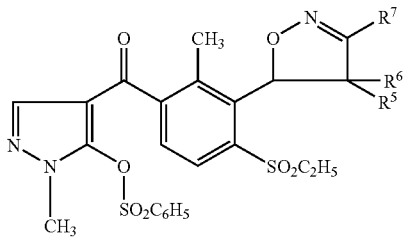

Ia297

Particular preference is likewise given to the compounds Ia298, in particular to the compounds Ia298.1–Ia298.64 which differ from compounds Ia1.1–Ia1.64 in that $R^1$ is methyl, $R^2$ is ethylsulfonyl, $R^{12}$ is phenylsulfonyl and $R^{13}$ is ethyl.

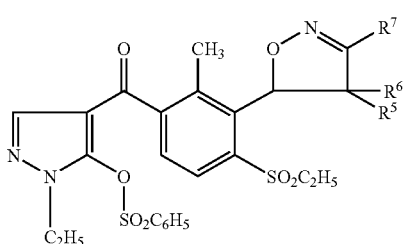

Ia298

Particular preference is likewise given to the compounds Ia299, in particular to the compounds Ia299.1–Ia299.64 which differ from compounds Ia1.1–Ia1.64 in that $R^1$ is methyl, $R^2$ is ethylsulfonyl, $R^{12}$ is phenylsulfonyl and $R^{13}$ is isopropyl.

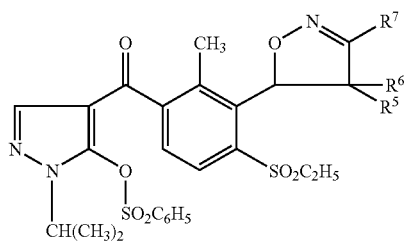
Ia299

Particular preference is likewise given to the compounds Ia300, in particular to the compounds Ia300.1–Ia300.64 which differ from compounds Ia1.1–Ia1.64 in that $R^1$ is methyl, $R^2$ is ethylsulfonyl, $R^{12}$ is phenylsulfonyl and $R^{13}$ is tert-butyl.

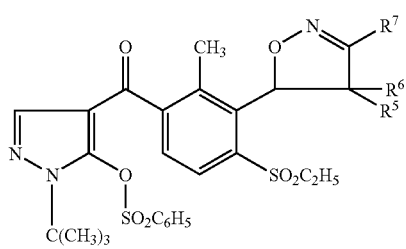
Ia300

Particular preference is likewise given to the compounds Ia301, in particular to the compounds Ia301.1–Ia301.64 which differ from compounds Ia1.1–Ia1.64 in that $R^1$ and $R^{14}$ are methyl, $R^2$ is ethylsulfonyl and $R^{12}$ is phenylsulfonyl.

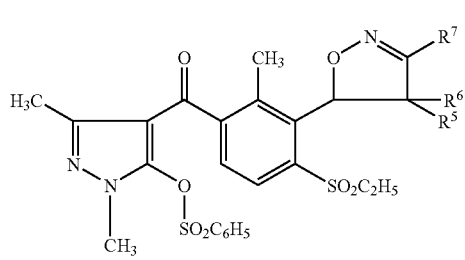
Ia301

Particular preference is likewise given to the compounds Ia302, in particular to the compounds Ia302.1–Ia302.64 which differ from compounds Ia1.1–Ia1.64 in that $R^1$ and $R^{14}$ are methyl, $R^2$ is ethylsulfonyl, $R^{12}$ is phenylsulfonyl and $R^{13}$ is ethyl.

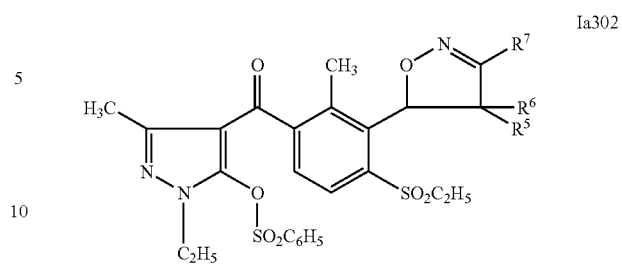
Ia302

Particular preference is likewise given to the compounds Ia303, in particular to the compounds Ia303.1–Ia303.64 which differ from compounds Ia1.1–Ia1.64 in that $R^1$ and $R^{14}$ are methyl, $R^2$ is ethylsulfonyl, $R^{12}$ is phenylsulfonyl and $R^{13}$ is isopropyl.

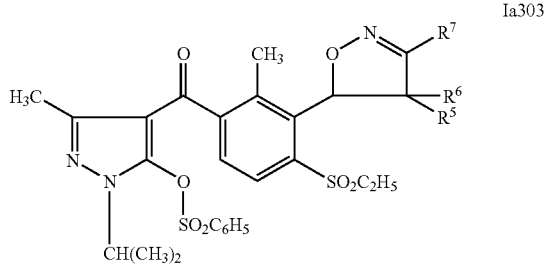
Ia303

Particular preference is likewise given to the compounds Ia304, in particular to the compounds Ia304.1–Ia304.64 which differ from compounds Ia1.1–Ia1.64 in that $R^1$ and $R^{14}$ are methyl, $R^2$ is ethylsulfonyl, $R^{12}$ is phenylsulfonyl and $R^{13}$ is tert-butyl.

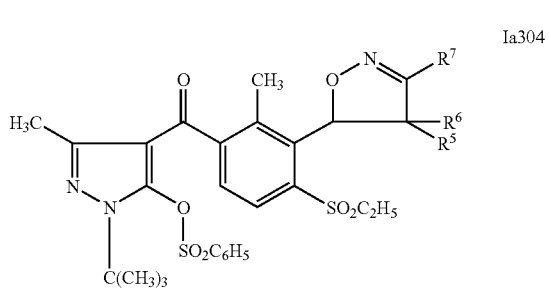
Ia304

Particular preference is likewise given to the compounds Ia305, in particular to the compounds Ia305.1–Ia305.64 which differ from compounds Ia1.1–Ia1.64 in that $R^2$ is chlorine and $R^{12}$ is phenylsulfonyl.

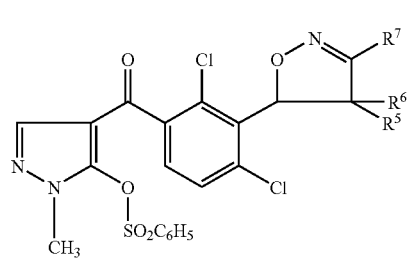
Ia305

Particular preference is likewise given to the compounds Ia306, in particular to the compounds Ia306.1–Ia306.64 which differ from compounds Ia1.1–Ia1.64 in that $R^2$ is chlorine, $R^{12}$ is phenylsulfonyl and $R^{13}$ is ethyl.

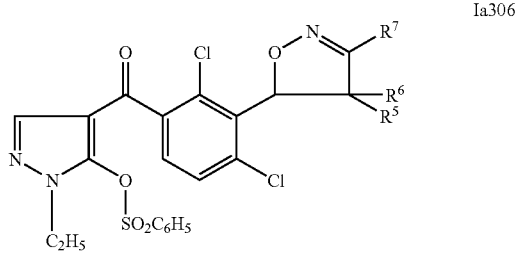

Ia306

Particular preference is likewise given to the compounds Ia307, in particular to the compounds Ia307.1–Ia307.64 which differ from compounds Ia1.1–Ia1.64 in that $R^2$ is chlorine, $R^{12}$ is phenylsulfonyl and $R^{13}$ is isopropyl.

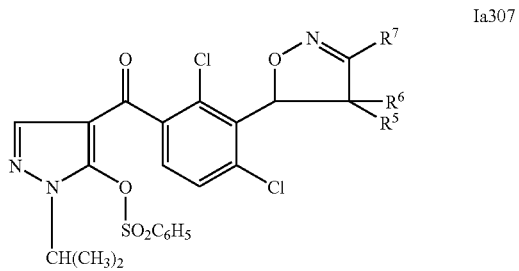

Ia307

Particular preference is likewise given to the compounds Ia308, in particular to the compounds Ia308.1–Ia308.64 which differ from compounds Ia1.1–Ia1.64 in that $R^2$ is chlorine, $R^{12}$ is phenylsulfonyl and $R^{13}$ is tert-butyl.

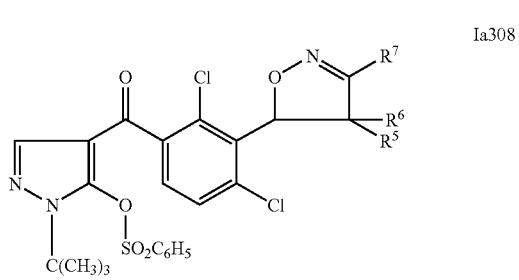

Ia308

Particular preference is likewise given to the compounds Ia309, in particular to the compounds Ia309.1–Ia309.64 which differ from compounds Ia1.1–Ia1.64 in that $R^2$ is chlorine, $R^{12}$ is phenylsulfonyl and $R^{14}$ is methyl.

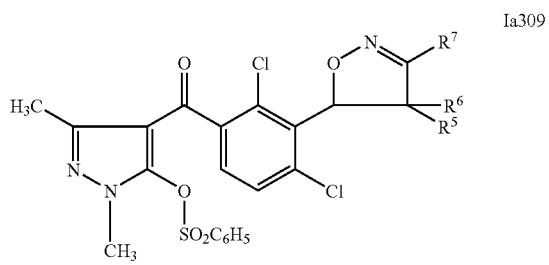

Ia309

Particular preference is likewise given to the compounds Ia310, in particular to the compounds Ia310.1–Ia310.64 which differ from compounds Ia1.1–Ia1.64 in that $R^2$ is chlorine, $R^{12}$ is phenylsulfonyl, $R^{13}$ is ethyl and $R^{14}$ is methyl.

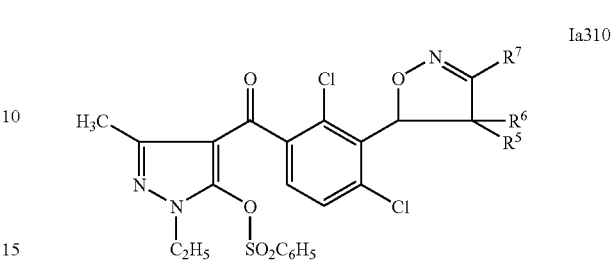

Ia310

Particular preference is likewise given to the compounds Ia311, in particular to the compounds Ia311.1–Ia311.64 which differ from compounds Ia1.1–Ia1.64 in that $R^2$ is chlorine, $R^{12}$ is phenylsulfonyl, $R^{13}$ is isopropyl and $R^{14}$ is methyl.

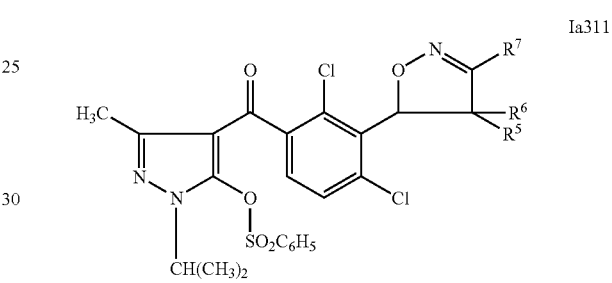

Ia311

Particular preference is likewise given to the compounds Ia312, in particular to the compounds Ia312.1–Ia312.64 which differ from compounds Ia1.1–Ia1.64 in that $R^2$ is chlorine, $R^{12}$ is phenylsulfonyl, $R^{13}$ is tert-butyl and $R^{14}$ is methyl.

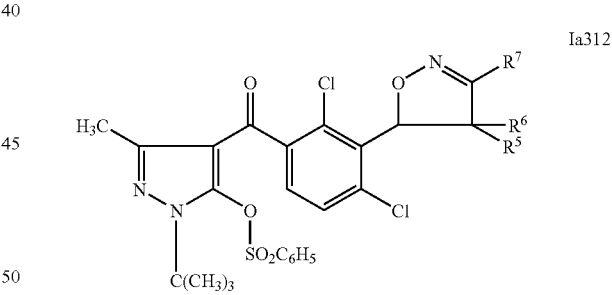

Ia312

Particular preference is likewise given to the compounds Ia313, in particular to the compounds Ia313.1–Ia313.64 which differ from compounds Ia1.1–Ia1.64 in that $R^1$ is methyl, $R^2$ is chlorine and $R^{12}$ is phenylsulfonyl.

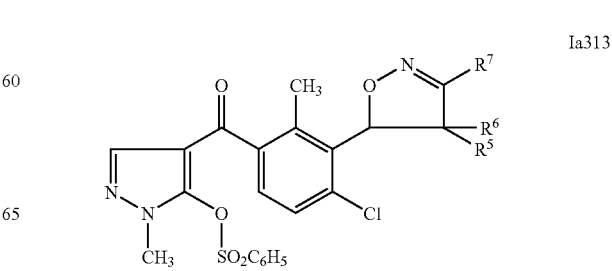

Ia313

Particular preference is likewise given to the compounds Ia314, in particular to the compounds Ia314.1–Ia314.64 which differ from compounds Ia1.1–Ia1.64 in that $R^1$ is methyl, $R^2$ is chlorine, $R^{12}$ is phenylsulfonyl and $R^{13}$ is ethyl.

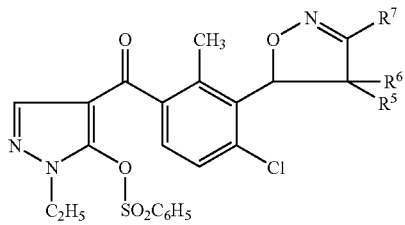

Ia314

Particular preference is likewise given to the compounds Ia315, in particular to the compounds Ia315.1–Ia315.64 which differ from compounds Ia1.1–Ia1.64 in that $R^1$ is methyl, $R^2$ is chlorine, $R^{12}$ is phenylsulfonyl and $R^{13}$ is isopropyl.

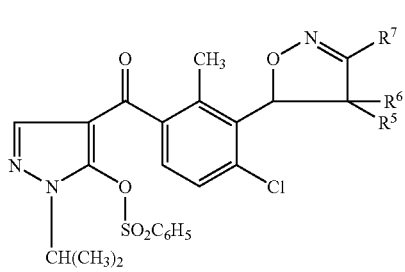

Ia315

Particular preference is likewise given to the compounds Ia316, in particular to the compounds Ia316.1–Ia316.64 which differ from compounds Ia1.1–Ia1.64 in that $R^1$ is methyl, $R^2$ is chlorine, $R^{12}$ is phenylsulfonyl and $R^{13}$ is tert-butyl.

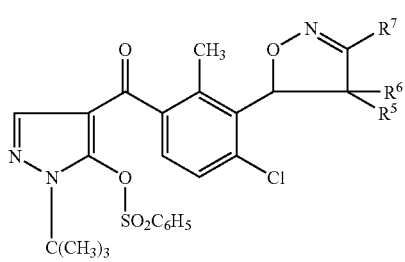

Ia316

Particular preference is likewise given to the compounds Ia317, in particular to the compounds Ia317.1–Ia317.64 which differ from compounds Ia1.1–Ia1.64 in that $R^1$ and $R^{14}$ are methyl, $R^2$ is chlorine and $R^{12}$ is phenylsulfonyl.

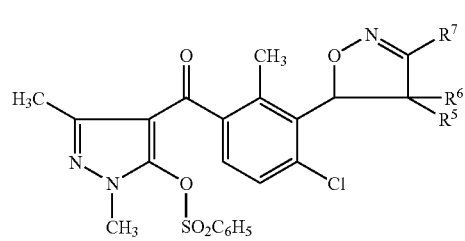

Ia317

Particular preference is likewise given to the compounds Ia318, in particular to the compounds Ia318.1–Ia318.64 which differ from compounds Ia1.1–Ia1.64 in that $R^1$ and $R^{14}$ are methyl, $R^2$ is chlorine, $R^{12}$ is phenylsulfonyl and $R^{13}$ is ethyl.

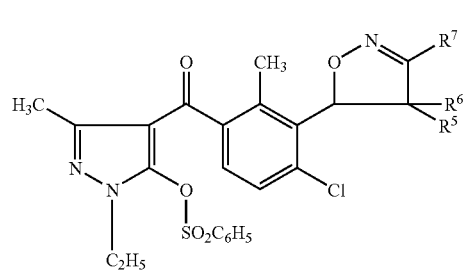

Ia318

Particular preference is likewise given to the compounds Ia319, in particular to the compounds Ia319.1–Ia319.64 which differ from compounds Ia1.1–Ia1.64 in that $R^1$ and $R^{14}$ are methyl, $R^2$ is chlorine, $R^{12}$ is phenylsulfonyl and $R^{13}$ is isopropyl.

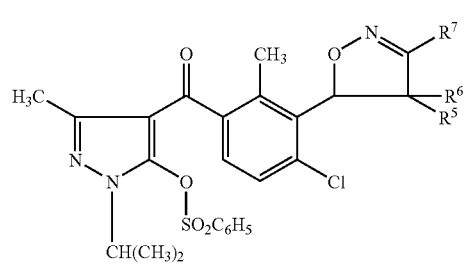

Ia319

Particular preference is likewise given to the compounds Ia320, in particular to the compounds Ia320.1–Ia320.64 which differ from compounds Ia1.1–Ia1.64 in that $R^1$ and $R^{14}$ are methyl, $R^2$ is chlorine, $R^{12}$ is phenylsulfonyl and $R^{13}$ is tert-butyl.

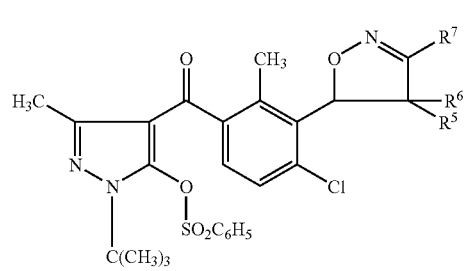

Ia320

Particular preference is likewise given to the compounds Ia321, in particular to the compounds Ia321.1–Ia321.64 which differ from compounds Ia1.1–Ia1.64 in that $R^{12}$ is 4-methylphenylsulfonyl.

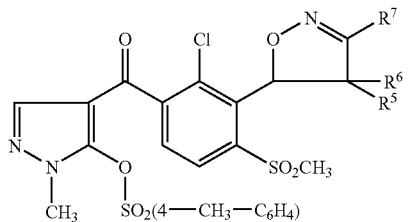

Ia321

Particular preference is likewise given to the compounds Ia322, in particular to the compounds Ia322.1–Ia322.64 which differ from compounds Ia1.1–Ia1.64 in that $R^{12}$ is 4-methylphenylsulfonyl and $R^{13}$ is ethyl.

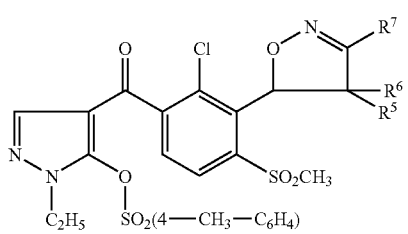

Ia322

Particular preference is likewise given to the compounds Ia323, in particular to the compounds Ia323.1–Ia323.64 which differ from compounds Ia1.1–Ia1.64 in that $R^{12}$ is 4-methylphenylsulfonyl and $R^{13}$ is isopropyl.

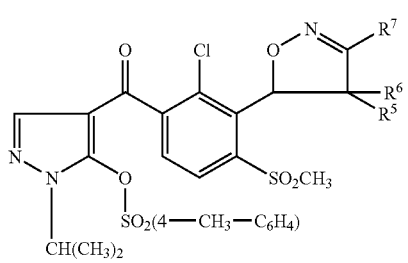

Ia323

Particular preference is likewise given to the compounds Ia324, in particular to the compounds Ia324.1–Ia324.64 which differ from compounds Ia1.1–Ia1.64 in that $R^{12}$ is 4-methylphenylsulfonyl and $R^{13}$ is tert-butyl.

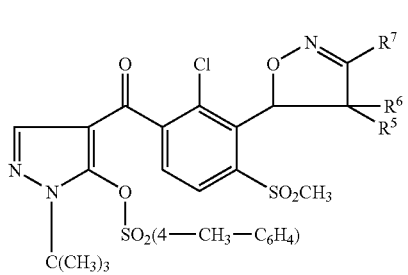

Ia324

Particular preference is likewise given to the compounds Ia325, in particular to the compounds Ia325.1–Ia325.64 which differ from compounds Ia1.1–Ia1.64 in that $R^{12}$ is 4-methylphenylsulfonyl and $R^{14}$ is methyl.

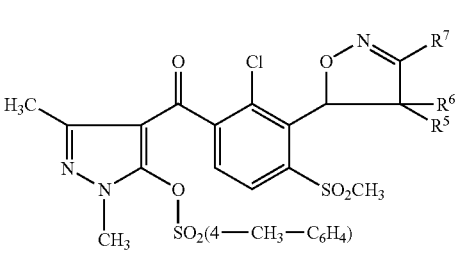

Ia325

Particular preference is likewise given to the compounds Ia326, in particular to the compounds Ia326.1–Ia326.64 which differ from compounds Ia1.1–Ia1.64 in that $R^{12}$ is 4-methylphenylsulfonyl, $R^{13}$ is ethyl and $R^{14}$ is methyl.

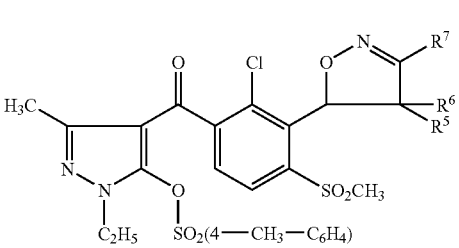

Ia326

Particular preference is likewise given to the compounds Ia327, in particular to the compounds Ia327.1–Ia327.64 which differ from compounds Ia1.1–Ia1.64 in that $R^{12}$ is 4-methylphenylsulfonyl, $R^{13}$ is isopropyl and $R^{14}$ is methyl.

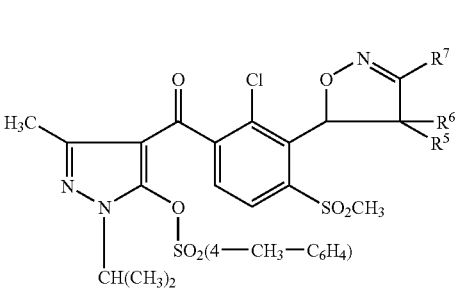

Ia327

Particular preference is likewise given to the compounds Ia328, in particular to the compounds Ia328.1–Ia328.64 which differ from compounds Ia1.1–Ia1.64 in that $R^{12}$ is 4-methylphenylsulfonyl, $R^{13}$ is tert-butyl and $R^{14}$ is methyl.

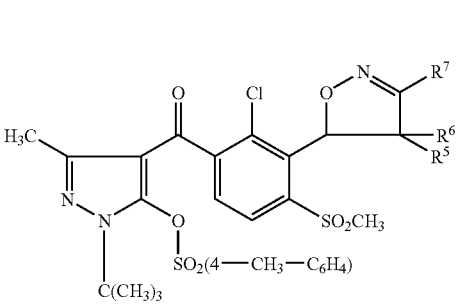

Ia328

Particular preference is likewise given to the compounds Ia329, in particular to the compounds Ia329.1–Ia329.64 which differ from compounds Ia1.1–Ia1.64 in that $R^1$ is methyl and $R^{12}$ is 4-methylphenylsulfonyl.

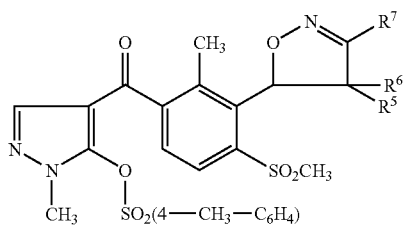
Ia329

Particular preference is likewise given to the compounds Ia330, in particular to the compounds Ia330.1–Ia330.64 which differ from compounds Ia1.1–Ia1.64 in that $R^1$ is methyl, $R^{12}$ is 4-methylphenylsulfonyl and $R^{13}$ is ethyl.

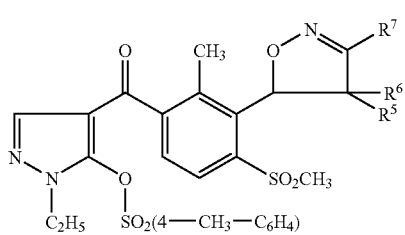
Ia330

Particular preference is likewise given to the compounds Ia331, in particular to the compounds Ia331.1–Ia331.64 which differ from compounds Ia1.1–Ia1.64 in that $R^1$ is methyl, $R^{12}$ is 4-methylphenylsulfonyl and $R^{13}$ is isopropyl.

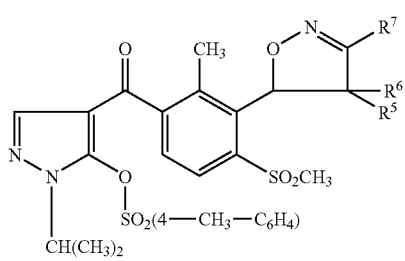
Ia331

Particular preference is likewise given to the compounds Ia332, in particular to the compounds Ia332.1–Ia332.64 which differ from compounds Ia1.1–Ia1.64 in that $R^1$ is methyl, $R^{12}$ is 4-methylphenylsulfonyl and $R^{13}$ is tert-butyl.

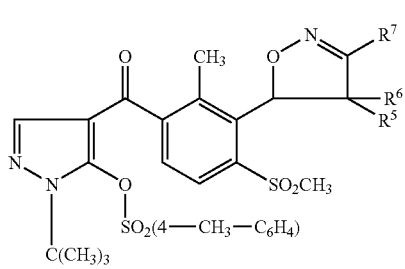
Ia332

Particular preference is likewise given to the compounds Ia333, in particular to the compounds Ia333.1–Ia333.64 which differ from compounds Ia1.1–Ia1.64 in that $R^1$ and $R^{14}$ are methyl and $R^{12}$ is 4-methylphenylsulfonyl.

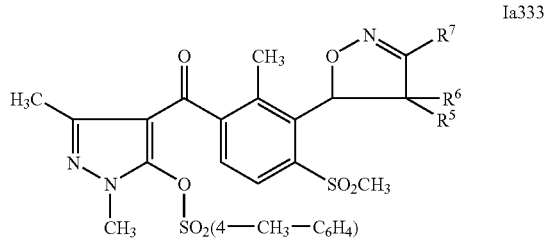
Ia333

Particular preference is likewise given to the compounds Ia334, in particular to the compounds Ia334.1–Ia334.64 which differ from compounds Ia1.1–Ia1.64 in that $R^1$ and $R^{14}$ are methyl, $R^{12}$ is 4-methylphenylsulfonyl and $R^{13}$ is ethyl.

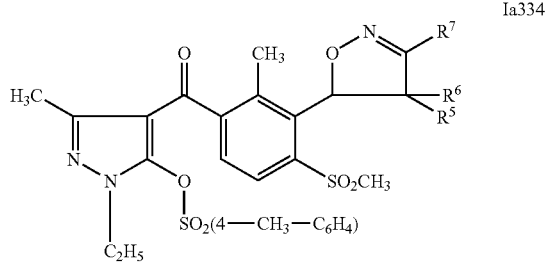
Ia334

Particular preference is likewise given to the compounds Ia335, in particular to the compounds Ia335.1–Ia334.64 which differ from compounds Ia1.1–Ia1.64 in that $R^1$ and $R^{14}$ are methyl, $R^{12}$ is 4-methylphenylsulfonyl and $R^{13}$ is isopropyl.

Ia335

Particular preference is likewise given to the compounds Ia336, in particular to the compounds Ia336.1–Ia336.64 which differ from compounds Ia1.1–Ia1.64 in that $R^1$ and $R^{14}$ are methyl, $R^{12}$ is 4-methylphenylsulfonyl and $R^{13}$ is tert-butyl.

Ia336

Particular preference is likewise given to the compounds Ia337, in particular to the compounds Ia337.1–Ia337.64 which differ from compounds Ia1.1–Ia1.64 in that $R^2$ is ethylsulfonyl and $R^{12}$ is 4-methylphenylsulfonyl.

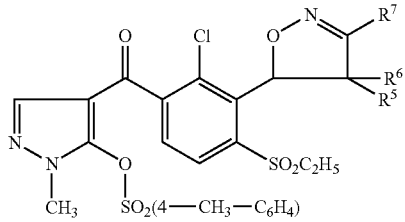

Ia337

Particular preference is likewise given to the compounds Ia338, in particular to the compounds Ia338.1–Ia338.64 which differ from compounds Ia1.1–Ia1.64 in that $R^2$ is ethylsulfonyl, $R^{12}$ is 4-methylphenylsulfonyl and $R^{13}$ is ethyl.

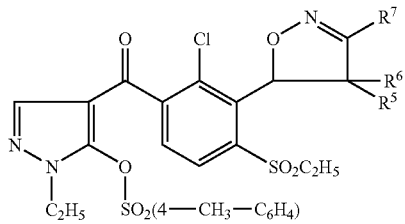

Ia338

Particular preference is likewise given to the compounds Ia339, in particular to the compounds Ia339.1–Ia339.64 which differ from compounds Ia1.1–Ia1.64 in that $R^2$ is ethylsulfonyl, $R^{12}$ is 4-methylphenylsulfonyl and $R^{13}$ is isopropyl.

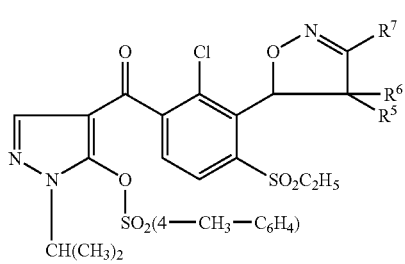

Ia339

Particular preference is likewise given to the compounds Ia340, in particular to the compounds Ia340.1–Ia340.64 which differ from compounds Ia1.1–Ia1.64 in that $R^2$ is ethylsulfonyl, $R^{12}$ is 4-methylphenylsulfonyl and $R^{13}$ is tert-butyl.

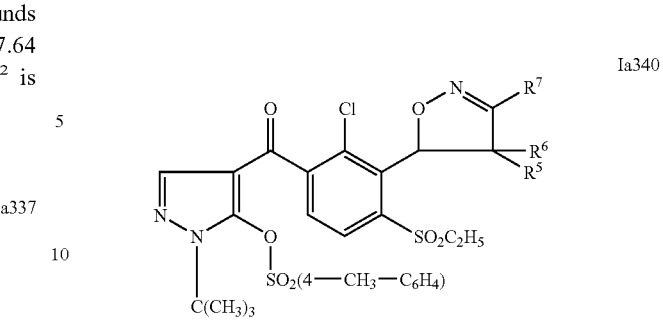

Ia340

Particular preference is likewise given to the compounds Ia341, in particular to the compounds Ia341.1–Ia341.64 which differ from compounds Ia1.1–Ia1.64 in that $R^2$ is ethylsulfonyl, $R^{12}$ is 4-methylphenylsulfonyl and $R^{14}$ is methyl.

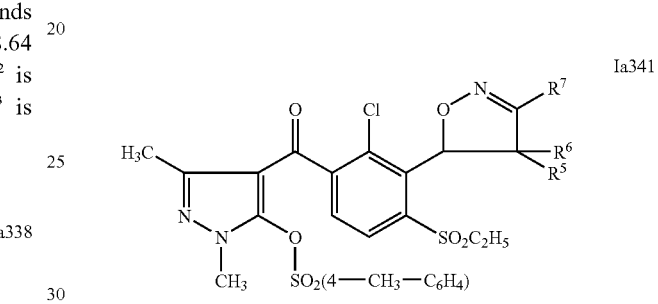

Ia341

Particular preference is likewise given to the compounds Ia342, in particular to the compounds Ia342.1–Ia342.64 which differ from compounds Ia1.1–Ia1.64 in that $R^2$ is ethylsulfonyl, $R^{12}$ is 4-methylphenylsulfonyl and $R^{14}$ is methyl.

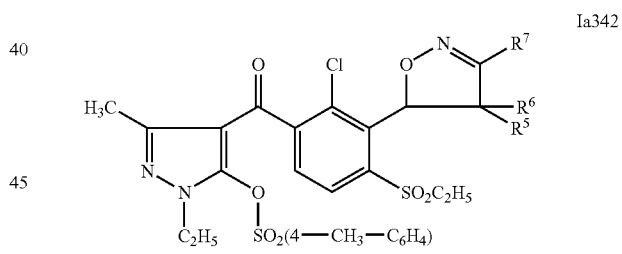

Ia342

Particular preference is likewise given to the compounds Ia343, in particular to the compounds Ia343.1–Ia343.64 which differ from compounds Ia1.1–Ia1.64 in that $R^2$ is ethylsulfonyl, $R^{12}$ is 4-methylphenylsulfonyl, $R^{13}$ is isopropyl and $R^{14}$ is methyl.

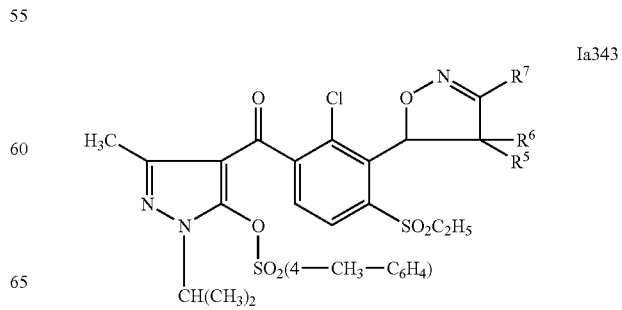

Ia343

Particular preference is likewise given to the compounds Ia344, in particular to the compounds Ia344.1–Ia344.64 which differ from compounds Ia1.1–Ia1.64 in that $R^2$ is ethylsulfonyl, $R^{12}$ is 4-methylphenylsulfonyl, $R^{13}$ is tert-butyl and $R^{14}$ is methyl.

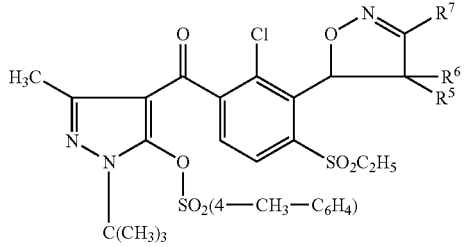

Ia344

Particular preference is likewise given to the compounds Ia345, in particular to the compounds Ia345.1–Ia345.64 which differ from compounds Ia1.1–Ia1.64 in that $R^1$ is methyl, $R^2$ is ethylsulfonyl and $R^{12}$ is 4-methylphenylsulfonyl.

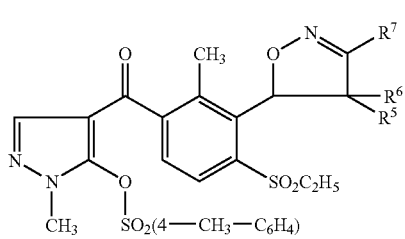

Ia345

Particular preference is likewise given to the compounds Ia346, in particular to the compounds Ia346.1–Ia346.64 which differ from compounds Ia1.1–Ia1.64 in that $R^1$ is methyl, $R^2$ is ethylsulfonyl, $R^{12}$ is 4-methylphenylsulfonyl and $R^{13}$ is ethyl.

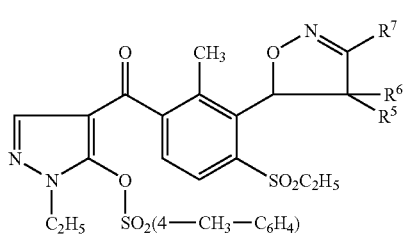

Ia346

Particular preference is likewise given to the compounds Ia347, in particular to the compounds Ia347.1–Ia347.64 which differ from compounds Ia1.1–Ia1.64 in that $R^1$ is methyl, $R^2$ is ethylsulfonyl, $R^{12}$ is 4-methylphenylsulfonyl and $R^{13}$ is isopropyl.

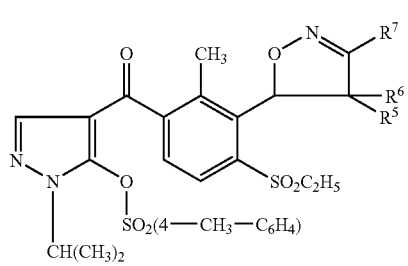

Ia347

Particular preference is likewise given to the compounds Ia348, in particular to the compounds Ia348.1–Ia348.64 which differ from compounds Ia1.1–Ia1.64 in that $R^1$ is methyl, $R^2$ is ethylsulfonyl, $R^{12}$ is 4-methylphenylsulfonyl and $R^{13}$ is tert-butyl.

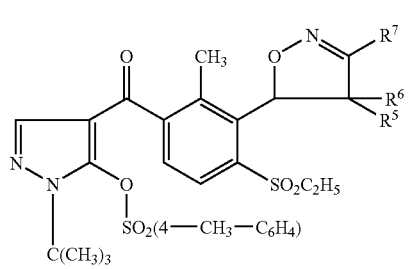

Ia348

Particular preference is likewise given to the compounds Ia349, in particular to the compounds Ia349.1–Ia348.64 [sic] which differ from compounds Ia1.1–Ia1.64 in that $R^1$ and $R^{14}$ are methyl, $R^2$ is ethylsulfonyl and $R^{12}$ is 4-methylphenylsulfonyl.

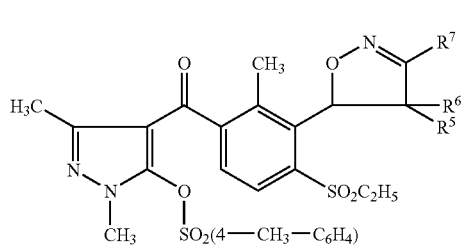

Ia349

Particular preference is likewise given to the compounds Ia350, in particular to the compounds Ia350.1–Ia350.64 which differ from compounds Ia1.1–Ia1.64 in that $R^1$ and $R^{14}$ are methyl, $R^2$ is ethylsulfonyl, $R^{12}$ is 4-methylphenylsulfonyl and $R^{13}$ is ethyl.

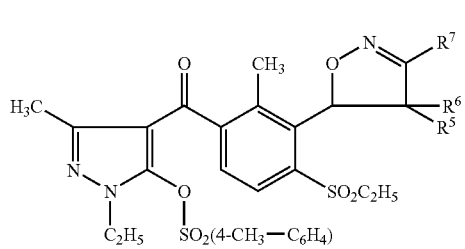

Ia350

Particular preference is likewise given to the compounds Ia351, in particular to the compounds Ia351.1–Ia351.64 which differ from compounds Ia1.1–Ia1.64 in that $R^1$ and $R^{14}$ are methyl, $R^2$ is ethylsulfonyl, $R^{12}$ is 4-methylphenylsulfonyl and $R^{13}$ is isopropyl.

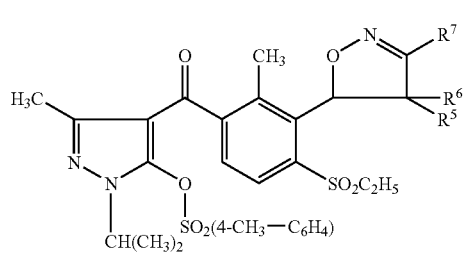

Particular preference is likewise given to the compounds Ia352, in particular to the compounds Ia352.1–Ia352.64 which differ from compounds Ia1.1–Ia1.64 in that $R^1$ and $R^{14}$ are methyl, $R^2$ is ethylsulfonyl, $R^{12}$ is 4-methylphenylsulfonyl and $R^{13}$ is tert-butyl.

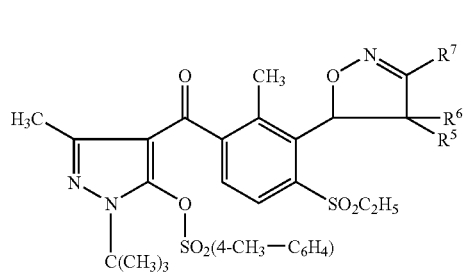

Particular preference is likewise given to the compounds Ia353, in particular to the compounds Ia353.1–Ia353.64 which differ from compounds Ia1.1–Ia1.64 in that $R^2$ is chlorine and $R^{12}$ is 4-methylphenylsulfonyl.

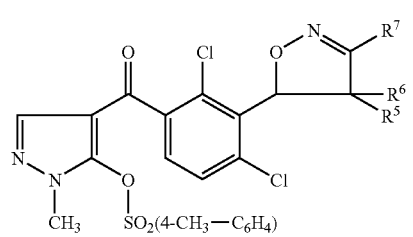

Particular preference is likewise given to the compounds Ia354, in particular to the compounds Ia354.1–Ia354.64 which differ from compounds Ia1.1–Ia1.64 in that $R^2$ is chlorine, $R^{12}$ is 4-methylphenylsulfonyl and $R^{13}$ is ethyl.

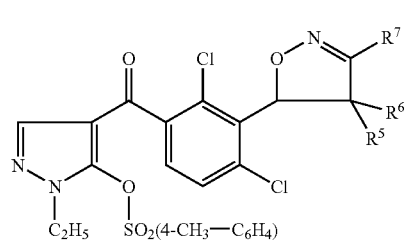

Particular preference is likewise given to the compounds Ia355, in particular to the compounds Ia355.1–Ia355.64 which differ from compounds Ia1.1–Ia1.64 in that $R^2$ is chlorine, $R^{12}$ is 4-methylphenylsulfonyl and $R^{13}$ is isopropyl.

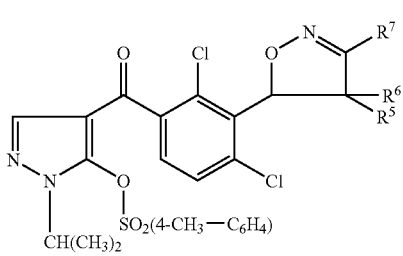

Particular preference is likewise given to the compounds Ia356, in particular to the compounds Ia356.1–Ia356.64 which differ from compounds Ia1.1–Ia1.64 in that $R^2$ is chlorine, $R^{12}$ is 4-methylphenylsulfonyl and $R^{13}$ is tert-butyl.

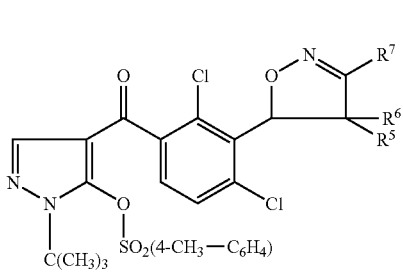

Particular preference is likewise given to the compounds Ia357, in particular to the compounds Ia357.1–Ia357.64 which differ from compounds Ia1.1–Ia1.64 in that $R^2$ is chlorine, $R^{12}$ is 4-methylphenylsulfonyl and $R^{14}$ is methyl.

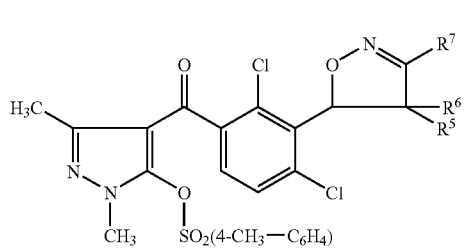

Particular preference is likewise given to the compounds Ia358, in particular to the compounds Ia358.1–Ia358.64 which differ from compounds Ia1.1–Ia1.64 in that $R^2$ is chlorine, $R^{12}$ is 4-methylphenylsulfonyl, $R^{13}$ is ethyl and $R^{14}$ is methyl.

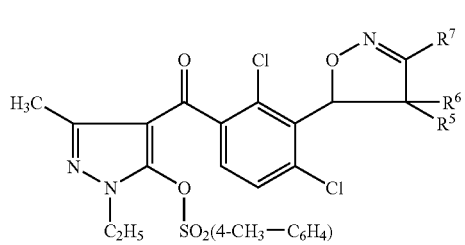

Particular preference is likewise given to the compounds Ia359, in particular to the compounds Ia359.1–Ia359.64 which differ from compounds Ia1.1–Ia1.64 in that $R^2$ is chlorine, $R^{12}$ is 4-methylphenylsulfonyl, $R^{13}$ is isopropyl and $R^{14}$ is methyl.

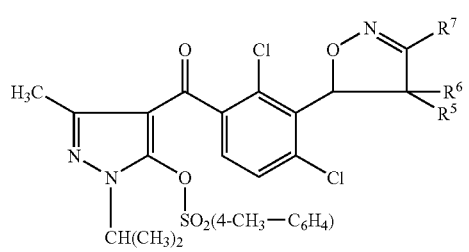

Ia359

Particular preference is likewise given to the compounds Ia360, in particular to the compounds Ia360.1–Ia360.64 which differ from compounds Ia1.1–Ia1.64 in that $R^2$ is chlorine, $R^{12}$ is 4-methylphenylsulfonyl, $R^{13}$ is tert-butyl and $R^{14}$ is methyl.

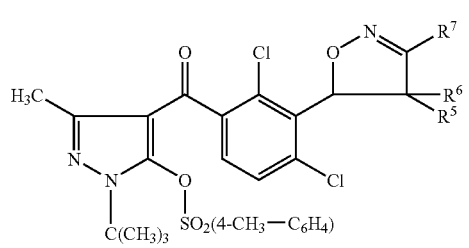

Ia360

Particular preference is likewise given to the compounds Ia361, in particular to the compounds Ia361.1–Ia361.64 which differ from compounds Ia1.1–Ia1.64 in that $R^1$ is methyl, $R^2$ is chlorine and $R^{12}$ is 4-methylphenylsulfonyl.

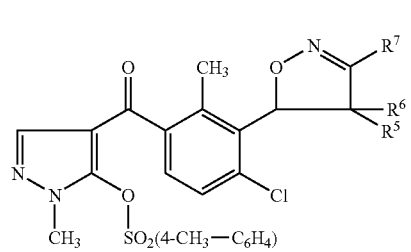

Ia361

Particular preference is likewise given to the compounds Ia362, in particular to the compounds Ia362.1–Ia362.64 which differ from compounds Ia1.1–Ia1.64 in that $R^1$ is methyl, $R^2$ is chlorine, $R^{12}$ is 4-methylphenylsulfonyl and $R^{13}$ is ethyl.

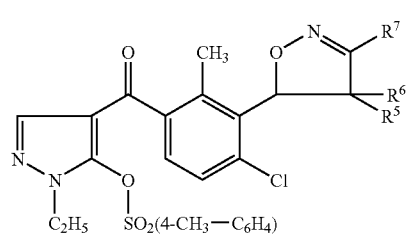

Ia362

Particular preference is likewise given to the compounds Ia363, in particular to the compounds Ia363.1–Ia363.64 which differ from compounds Ia1.1–Ia1.64 in that $R^1$ is methyl, $R^2$ is chlorine, $R^{12}$ is 4-methylphenylsulfonyl and $R^{13}$ is isopropyl.

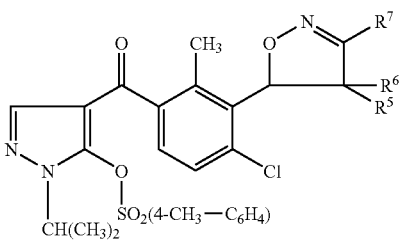

Ia363

Particular preference is likewise given to the compounds Ia364, in particular to the compounds Ia364.1–Ia364.64 which differ from compounds Ia1.1–Ia1.64 in that $R^1$ is methyl, $R^2$ is chlorine, $R^{12}$ is 4-methylphenylsulfonyl and $R^{13}$ is tert-butyl.

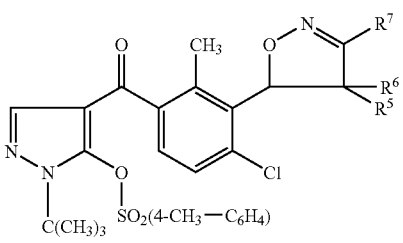

Ia364

Particular preference is likewise given to the compounds Ia365, in particular to the compounds Ia365.1–Ia365.64 which differ from compounds Ia1.1–Ia1.64 in that $R^1$ and $R^{14}$ are methyl, $R^2$ is chlorine and $R^{12}$ is 4-methylphenylsulfonyl.

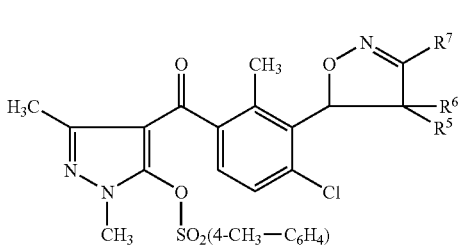

Ia365

Particular preference is likewise given to the compounds Ia366, in particular to the compounds Ia366.1–Ia366.64 which differ from compounds Ia1.1–Ia1.64 in that $R^1$ and $R^{14}$ are methyl, $R^2$ is chlorine, $R^{12}$ is 4-methylphenylsulfonyl and $R^{13}$ is ethyl.

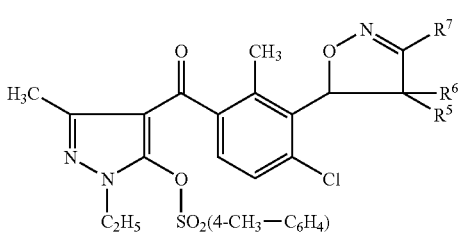

Ia366

Particular preference is likewise given to the compounds Ia367, in particular to the compounds Ia367.1–Ia367.64 which differ from compounds Ia1.1–Ia1.64 in that $R^1$ and $R^{14}$ are methyl, $R^2$ is chlorine, $R^{12}$ is 4-methylphenylsulfonyl and $R^{13}$ is isopropyl.

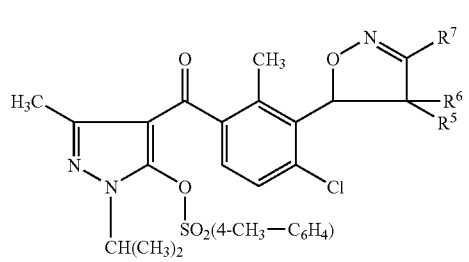

Ia367

Particular preference is likewise given to the compounds Ia368, in particular to the compounds Ia368.1–Ia368.64 which differ from compounds Ia1.1–Ia1.64 in that $R^1$ and $R^{14}$ are methyl, $R^2$ is chlorine, $R^{12}$ is 4-methylphenylsulfonyl and $R^{13}$ is tert-butyl.

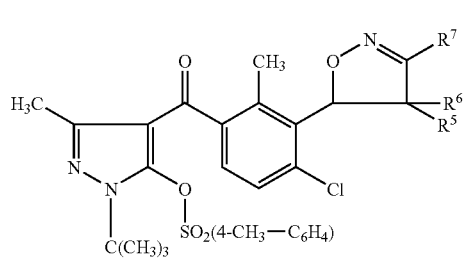

Ia368

Particular preference is likewise given to the compounds Ia369, in particular to the compounds Ia369.1–Ia369.64 which differ from compounds Ia1.1–Ia1.64 in that $R^{13}$ is cyclopropyl.

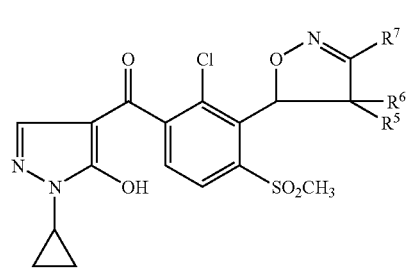

Ia369

Particular preference is likewise given to the compounds Ia370, in particular to the compounds Ia370.1 to Ia370.64 which differ from compounds Ia1.1–Ia1.64 in that $R^{13}$ is cyclopropyl and $R^{14}$ is methyl.

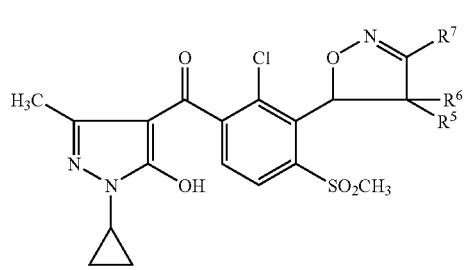

Ia370

Particular preference is likewise given to the compounds Ia371, in particular to the compounds Ia371.1 to Ia371.64 which differ from compounds Ia1.1–Ia1.64 in that $R^1$ is methyl and $R^{13}$ is cyclopropyl.

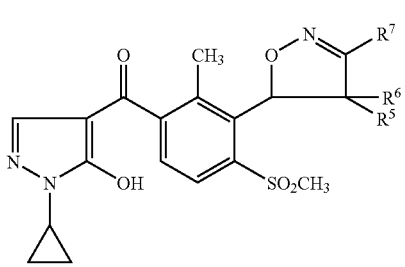

Ia371

Particular preference is likewise given to the compounds Ia372, in particular to the compounds Ia372.1 to Ia372.64 which differ from compounds Ia1.1–Ia1.64 in that $R^1$ is methyl, $R^{13}$ is cyclopropyl and $R^{14}$ is methyl.

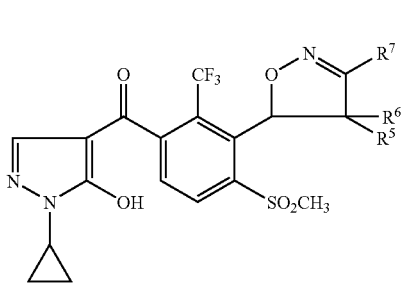

Ia372

Particular preference is likewise given to the compounds Ia373, in particular to the compounds Ia373.1 to Ia373.64 which differ from compounds Ia1.1–Ia1.64 in that $R^1$ is trifluoromethyl and $R^{13}$ is cyclopropyl.

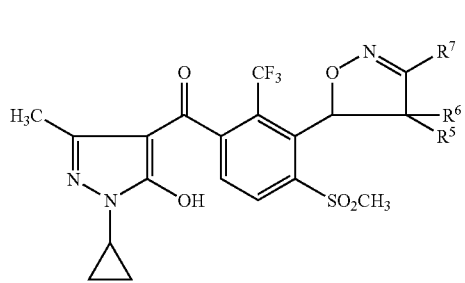

Ia373

Particular preference is likewise given to the compounds Ia374, in particular to the compounds Ia374.1 to Ia374.64 which differ from compounds Ia1.1–Ia1.64 in that $R^1$ is trifluoromethyl, $R^{13}$ is cyclopropyl and $R^{14}$ is methyl.

Ia374

Particular preference is likewise given to the compounds Ia375, in particular to the compounds Ia375.1 to Ia375.64 which differ from compounds Ia1.1–Ia1.64 in that R¹ is methoxy and R¹³ is cyclopropyl.

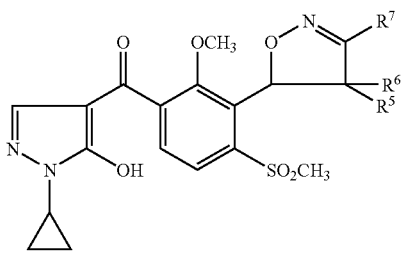
Ia375

Particular preference is likewise given to the compounds Ia376, in particular to the compounds Ia376.1 to Ia376.64 which differ from compounds Ia1.1–Ia1.64 in that R¹ is methoxy, R¹³ is cyclopropyl and R¹⁴ is methyl.

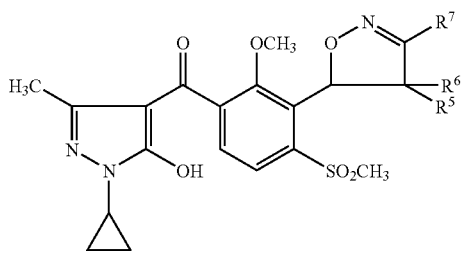
Ia376

Particular preference is likewise given to the compounds Ia377, in particular to the compounds Ia377.1 to Ia377.64 which differ from compounds Ia1.1–Ia1.64 in that R² is ethylsulfonyl and R¹³ is cyclopropyl.

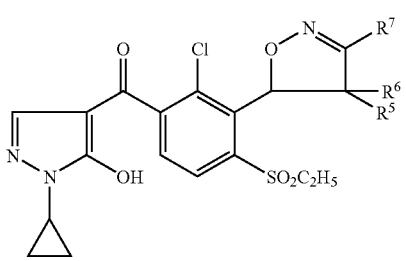
Ia377

Particular preference is likewise given to the compounds Ia378, in particular to the compounds Ia378.1 to Ia378.64 which differ from compounds Ia1.1–Ia1.64 in that R² is ethylsulfonyl, R¹³ is cyclopropyl and R¹⁴ is methyl.

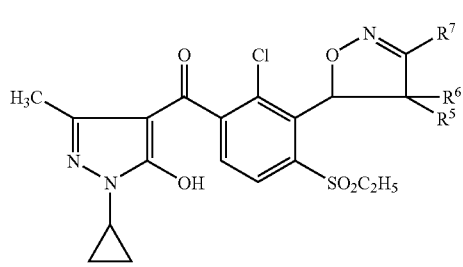
Ia378

Particular preference is likewise given to the compounds Ia379, in particular to the compounds Ia379.1 to Ia379.64 which differ from compounds Ia1.1–Ia1.64 in that R¹ is methyl, R² is ethylsulfonyl and R¹³ is cyclopropyl.

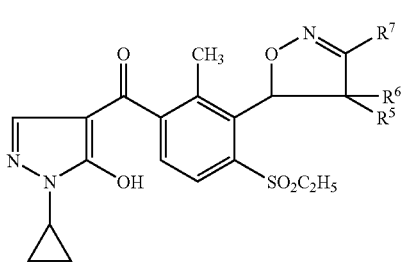
Ia379

Particular preference is likewise given to the compounds Ia380, in particular to the compounds Ia380.1 to Ia380.64 which differ from compounds Ia1.1–Ia1.64 in that R¹ is methyl, R² is ethylsulfonyl, R¹³ is cyclopropyl and R¹⁴ is methyl.

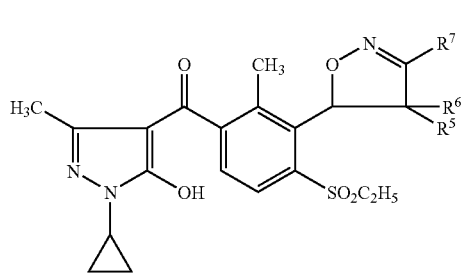
Ia380

Particular preference is likewise given to the compounds Ia381, in particular to the compounds Ia381.1 to Ia381.64 which differ from compounds Ia1.1–Ia1.64 in that R¹ is trifluoromethyl, R² is ethylsulfonyl and R¹³ is cyclopropyl.

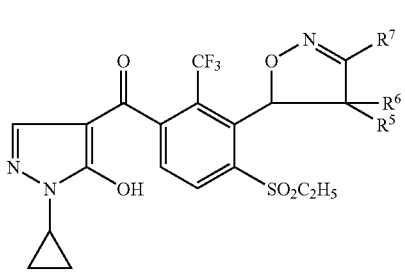
Ia381

Particular preference is likewise given to the compounds Ia382, in particular to the compounds Ia382.1 to Ia382.64 which differ from compounds Ia1.1–Ia1.64 in that $R^1$ is trifluoromethyl, $R^2$ is ethylsulfonyl, $R^{13}$ is cyclopropyl and $R^{14}$ is methyl.

Ia382

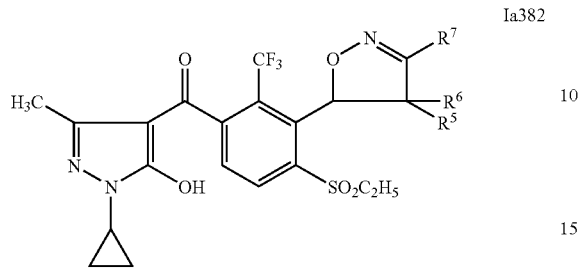

Particular preference is likewise given to the compounds Ia383, in particular to the compounds Ia383.1 to Ia383.64 which differ from compounds Ia1.1–Ia1.64 in that $R^1$ is methoxy, $R^2$ is ethylsulfonyl and $R^{13}$ is cyclopropyl.

Ia383

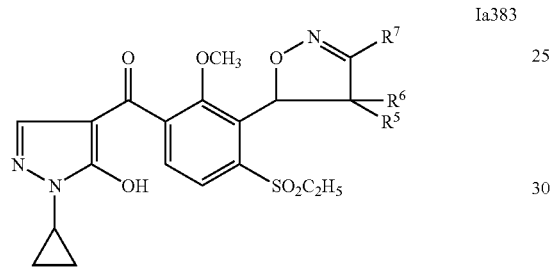

Particular preference is likewise given to the compounds Ia384, in particular to the compounds Ia384.1 to Ia384.64 which differ from compounds Ia1.1–Ia1.64 in that $R^1$ is methoxy, $R^2$ is ethylsulfonyl, $R^{13}$ is cyclopropyl and $R^{14}$ is methyl.

Ia384

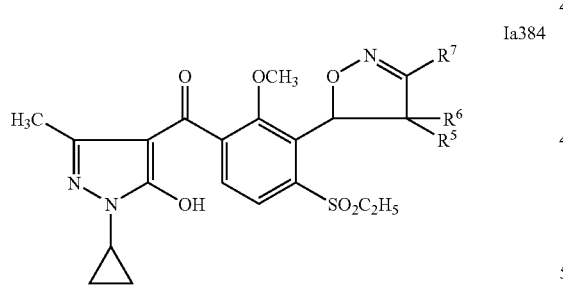

Particular preference is likewise given to the compounds Ia385, in particular to the compounds Ia385.1 to Ia385.64 which differ from compounds Ia1.1–Ia1.64 in that $R^2$ is chlorine and $R^{13}$ is cyclopropyl.

Ia385

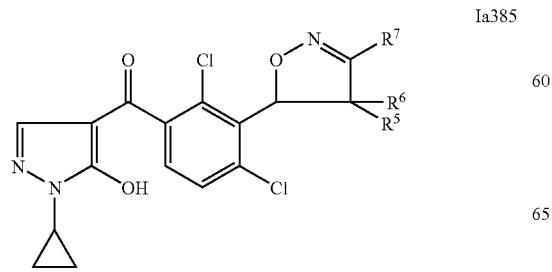

Particular preference is likewise given to the compounds Ia386, in particular to the compounds Ia386.1 to Ia386.64 which differ from compounds Ia1.1–Ia1.64 in that $R^2$ is chlorine, $R^{13}$ is cyclopropyl and $R^{14}$ is methyl.

Ia386

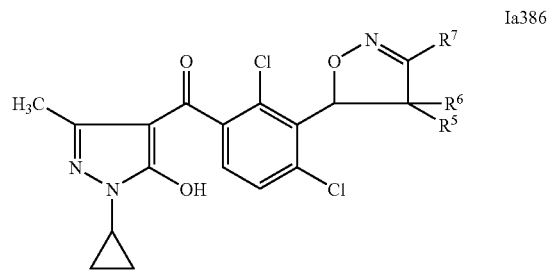

Particular preference is likewise given to the compounds Ia387, in particular to the compounds Ia387.1 to Ia387.64 which differ from compounds Ia1.1–Ia1.64 in that $R^1$ is methyl, $R^2$ is chlorine and $R^{13}$ is cyclopropyl.

Ia387

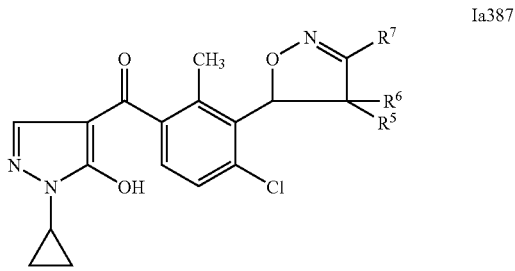

Particular preference is likewise given to the compounds Ia388, in particular to the compounds Ia388.1 to Ia388.64 which differ from compounds Ia1.1–Ia1.64 in that $R^1$ is methyl, $R^2$ is chlorine, $R^{13}$ is cyclopropyl and $R^{14}$ is methyl.

Ia388

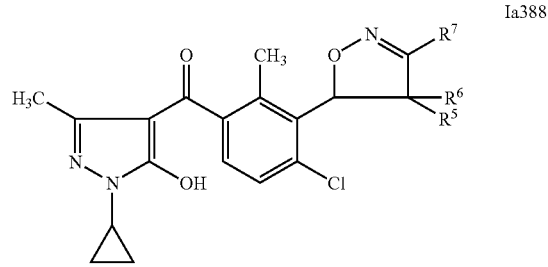

Particular preference is likewise given to the compounds Ia389, in particular to the compounds Ia389.1 to Ia389.64 which differ from compounds Ia1.1–Ia1.64 in that $R^1$ is trifluoromethyl, $R^2$ is chlorine and $R^{13}$ is cyclopropyl.

Ia389

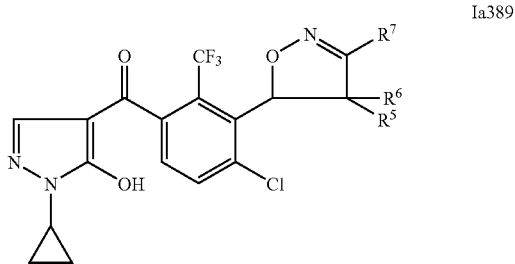

Particular preference is likewise given to the compounds Ia390, in particular to the compounds Ia390.1 to Ia390.64 which differ from compounds Ia1.1–Ia1.64 in that $R^1$ is trifluoromethyl, $R^2$ is chlorine, $R^{13}$ is cyclopropyl and $R^{14}$ is methyl.

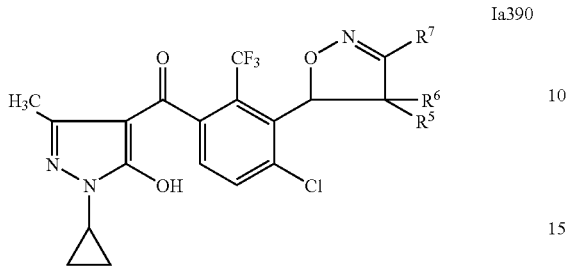

Ia390

Particular preference is likewise given to the compounds Ia391, in particular to the compounds Ia391.1 to Ia391.64 which differ from compounds Ia1.1–Ia1.64 in that $R^1$ is methoxy, $R^2$ is chlorine and $R^{13}$ is cyclopropyl.

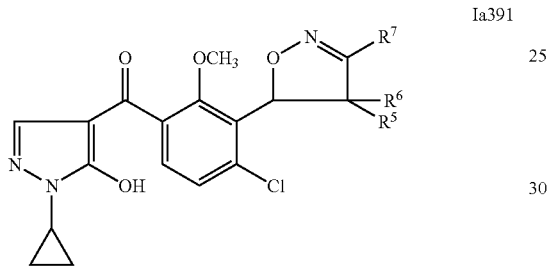

Ia391

Particular preference is likewise given to the compounds Ia392, in particular to the compounds Ia392.1 to Ia392.64 which differ from compounds Ia1.1–Ia1.64 in that $R^1$ is methoxy, $R^2$ is chlorine, $R^{13}$ is cyclopropyl and $R^{14}$ is methyl.

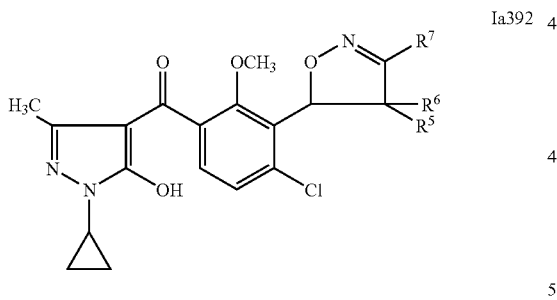

Ia392

Particular preference is likewise given to the compounds Ia393, in particular to the compounds Ia393.1 to Ia393.64 which differ from compounds Ia1.1–Ia1.64 in that $R^2$ is trifluoromethyl and $R^{13}$ is cyclopropyl.

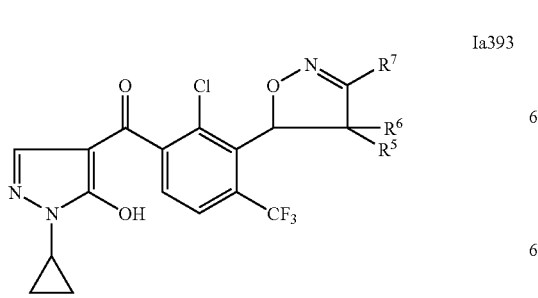

Ia393

Particular preference is likewise given to the compounds Ia394, in particular to the compounds Ia394.1 to Ia394.64 which differ from compounds Ia1.1–Ia1.64 in that $R^1$ is trifluoromethyl, $R^{13}$ is cyclopropyl and $R^{14}$ is methyl.

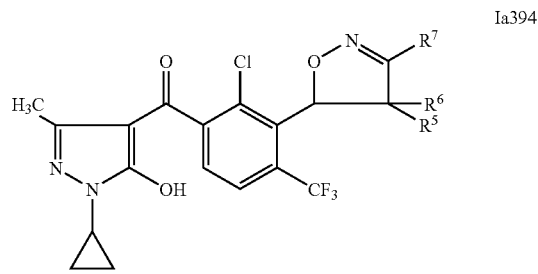

Ia394

Particular preference is likewise given to the compounds Ia395, in particular to the compounds Ia395.1 to Ia395.64 which differ from compounds Ia1.1–Ia1.64 in that $R^1$ methyl, $R^2$ is trifluoromethyl and $R^{13}$ is cyclopropyl.

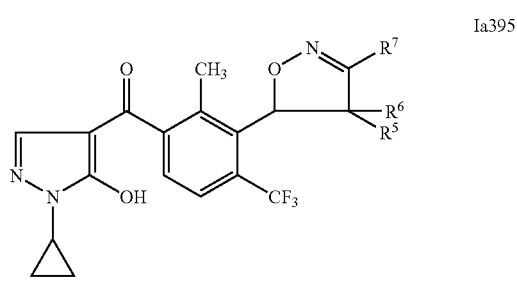

Ia395

Particular preference is likewise given to the compounds Ia396, in particular to the compounds Ia396.1 to Ia396.64 which differ from compounds Ia1.1–Ia1.64 in that $R^1$ is methyl, $R^2$ is trifluoromethyl, $R^{13}$ is cyclopropyl and $R^{14}$ is methyl.

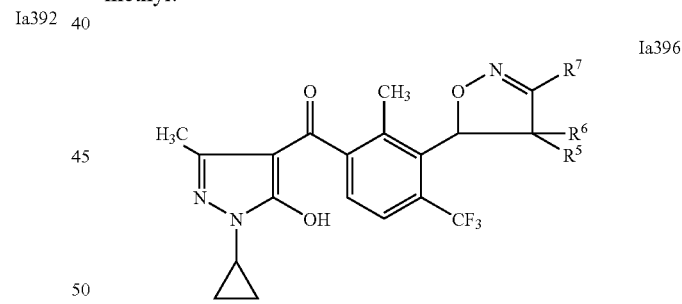

Ia396

Particular preference is likewise given to the compounds Ia397, in particular to the compounds Ia397.1 to Ia397.64 which differ from compounds Ia1.1–Ia1.64 in that $R^1$ and $R^2$ are trifluoromethyl and $R^{13}$ is cyclopropyl.

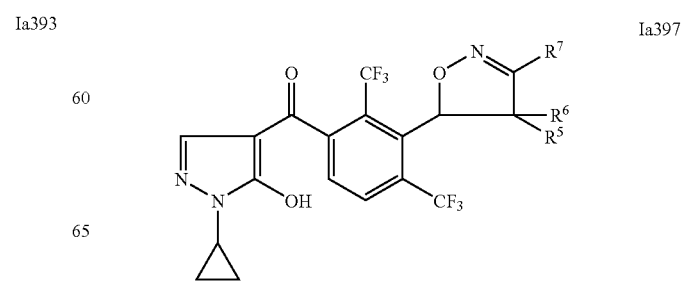

Ia397

Particular preference is likewise given to the compounds Ia398, in particular to the compounds Ia398.1 to Ia398.64 which differ from compounds Ia1.1–Ia1.64 in that $R^1$ and $R^2$ are trifluoromethyl, $R^{13}$ is cyclopropyl and $R^{14}$ is methyl.

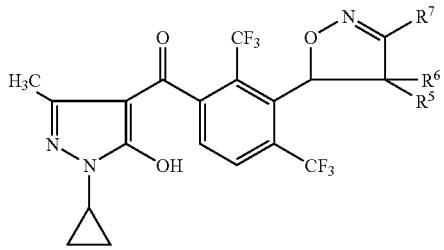

Ia398

Particular preference is likewise given to the compounds Ia399, in particular to the compounds Ia399.1 to Ia399.64 which differ from compounds Ia1.1–Ia1.64 in that $R^1$ is methoxy, $R^2$ is trifluoromethyl and $R^{13}$ is cyclopropyl.

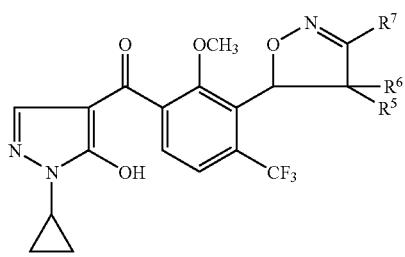

Ia399

Particular preference is likewise given to the compounds Ia400, in particular to the compounds Ia400.1 to Ia400.64 which differ from compounds Ia1.1–Ia1.64 in that $R^1$ is methoxy, $R^2$ is trifluoromethyl, $R^{13}$ is cyclopropyl and $R^{14}$ is methyl.

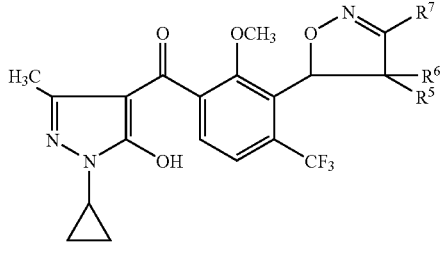

Ia400

Particular preference is likewise given to the compounds Ia401, in particular to the compounds Ia401.1 to Ia401.64 which differ from compounds Ia1.1–Ia1.64 in that $R^3$ is chlorine and $R^{13}$ is cyclopropyl.

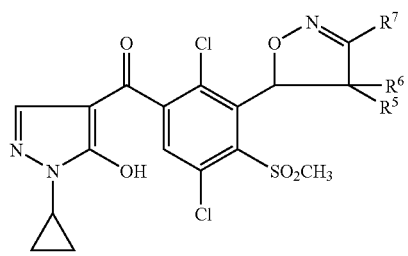

Ia401

Particular preference is likewise given to the compounds Ia402, in particular to the compounds Ia402.1 to Ia402.64 which differ from compounds Ia1.1–Ia1.64 in that $R^3$ is chlorine, $R^{13}$ is cyclopropyl and $R^{14}$ is methyl.

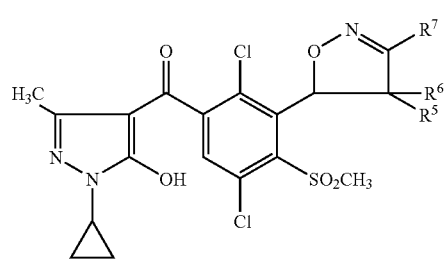

Ia402

Particular preference is likewise given to the compounds Ia403, in particular to the compounds Ia403.1 to Ia403.64 which differ from compounds Ia1.1–Ia1.64 in that $R^2$ is ethylsulfonyl, $R^3$ is chlorine and $R^{13}$ is cyclopropyl.

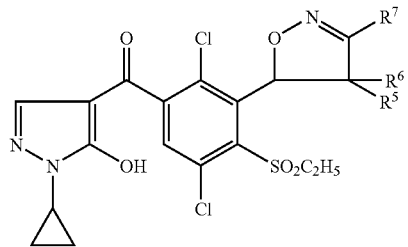

Ia403

Particular preference is likewise given to the compounds Ia404, in particular to the compounds Ia404.1 to Ia404.64 which differ from compounds Ia1.1–Ia1.64 in that $R^2$ is ethylsulfonyl, $R^3$ is chlorine, $R^{13}$ is cyclopropyl and $R^{14}$ is methyl.

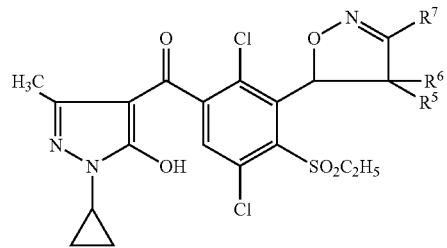

Ia404

Particular preference is likewise given to the compounds Ia405, in particular to the compounds Ia405.1 to Ia405.64 which differ from compounds Ia1.1–Ia1.64 in that $R^1$ and $R^3$ are methyl, $R^{13}$ is cyclopropyl.

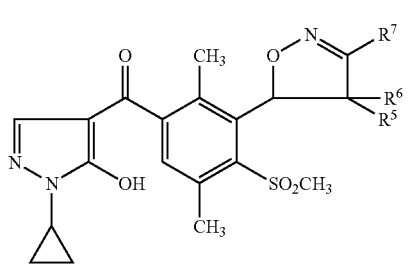

Ia405

Particular preference is likewise given to the compounds Ia406, in particular to the compounds Ia406.1 to Ia406.64 which differ from compounds Ia1.1–Ia1.64 in that $R^1$, $R^3$ and $R^{14}$ are methyl and $R^{13}$ is cyclopropyl.

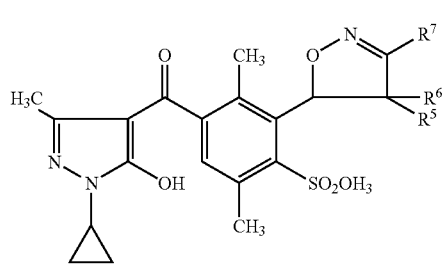

Ia406

Particular preference is likewise given to the compounds Ia407, in particular to the compounds Ia407.1 to Ia407.64 which differ from compounds Ia1.1–Ia1.64 in that $R^1$ and $R^3$ are methyl, $R^2$ is ethylsulfonyl and $R^{13}$ is cyclopropyl.

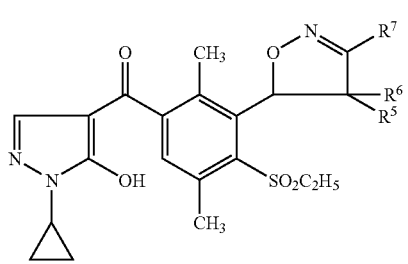

Ia407

Particular preference is likewise given to the compounds Ia408, in particular to the compounds Ia408.1 to Ia408.64 which differ from compounds Ia1.1–Ia1.64 in that $R^1$, $R^3$ and $R^{14}$ are methyl, $R^2$ is ethylsulfonyl and $R^{13}$ is cyclopropyl.

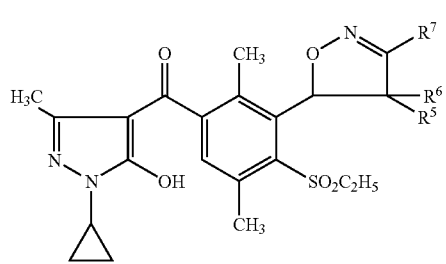

Ia408

Particular preference is likewise given to the compounds Ia409, in particular to the compounds Ia409.1 to Ia409.64 which differ from compounds Ia1.1–Ia1.64 in that $R^1$ and $R^3$ are methyl, $R^2$ is chlorine and $R^{13}$ is cyclopropyl.

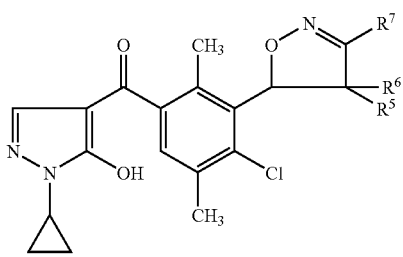

Ia409

Particular preference is likewise given to the compounds Ia410, in particular to the compounds Ia410.1 to Ia410.64 which differ from compounds Ia1.1–Ia1.64 in that $R^1$, $R^3$ and $R^{14}$ are methyl, $R^2$ is chlorine and $R^{13}$ is cyclopropyl.

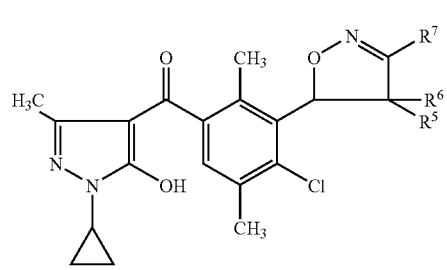

Ia410

Particular preference is likewise given to the compounds Ia411, in particular to the compounds Ia411.1 to Ia411.64 which differ from compounds Ia1.1–Ia1.64 in that is $R^{12}$ methylsulfonyl and $R^{13}$ is cyclopropyl.

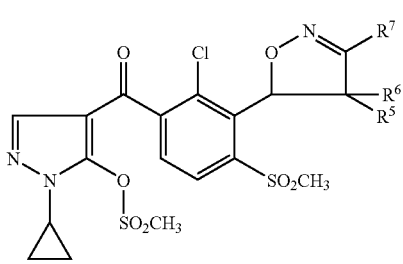

Ia411

Particular preference is likewise given to the compounds Ia412, in particular to the compounds Ia412.1 to Ia412.64 which differ from compounds Ia1.1–Ia1.64 in that is $R^{12}$ methylsulfonyl, $R^{13}$ is cyclopropyl and $R^{14}$ is methyl.

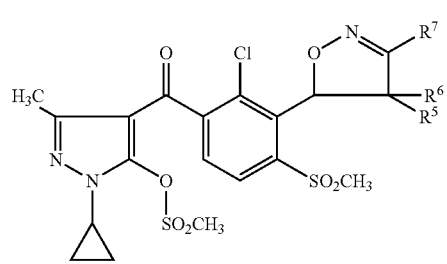

Ia412

Particular preference is likewise given to the compounds Ia413, in particular to the compounds Ia413.1 to Ia413.64 which differ from compounds Ia1.1–Ia1.64 in that $R^1$ is methyl, $R^{12}$ is methylsulfonyl and $R^{13}$ is cyclopropyl.

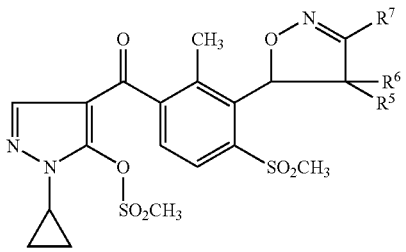

Ia413

Particular preference is likewise given to the compounds Ia414, in particular to the compounds Ia414.1 to Ia414.64 which differ from compounds Ia1.1–Ia1.64 in that $R^1$ and $R^{14}$ is methyl, $R^{12}$ is methylsulfonyl and $R^{13}$ is cyclopropyl.

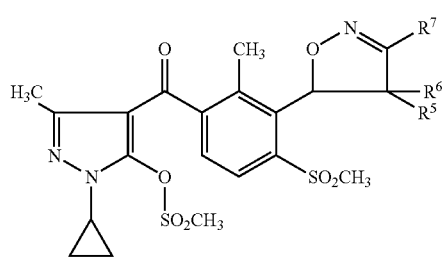

Ia414

Particular preference is likewise given to the compounds Ia414, in particular to the compounds Ia414.1 to Ia414.64 which differ from compounds Ia1.1–Ia1.64 in that $R^2$ is ethylsulfonyl, $R^{12}$ is methylsulfonyl and $R^{13}$ is cyclopropyl.

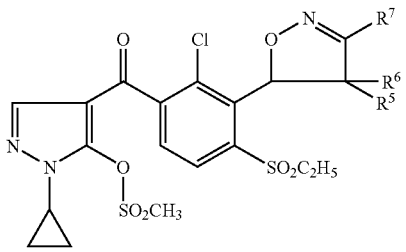

Ia415

Particular preference is likewise given to the compounds Ia416, in particular to the compounds Ia416.1 to Ia416.64 which differ from compounds Ia1.1–Ia1.64 in that $R^2$ is ethylsulfonyl, $R^{12}$ is methylsulfonyl, $R^{13}$ is cyclopropyl and $R^{14}$ is methyl.

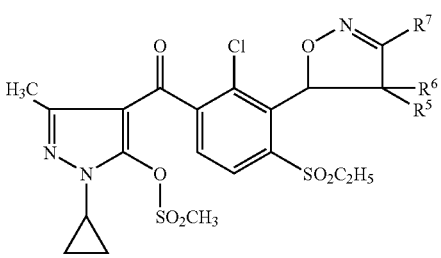

Ia416

Particular preference is likewise given to the compounds Ia417, in particular to the compounds Ia417.1 to Ia417.64 which differ from compounds Ia1.1–Ia1.64 in that $R^1$ is methyl, $R^2$ is ethylsulfonyl, $R^{12}$ is methylsulfonyl and $R^{13}$ is cyclopropyl.

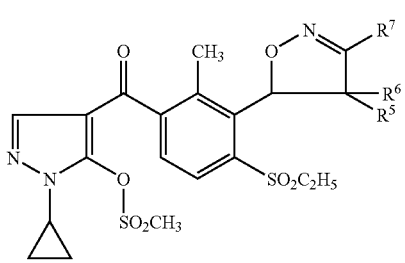

Ia417

Particular preference is likewise given to the compounds Ia418, in particular to the compounds Ia418.1 to Ia418.64 which differ from compounds Ia1.1–Ia1.64 in that $R^1$ and $R^{14}$ are methyl, $R^2$ is ethylsulfonyl, $R^{12}$ is methylsulfonyl and $R^{13}$ is cyclopropyl.

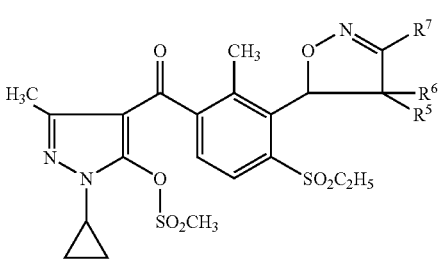

Ia418

Particular preference is likewise given to the compounds Ia419, in particular to the compounds Ia419.1 to Ia419.64 which differ from compounds Ia1.1–Ia1.64 in that $R^2$ is chlorine, $R^{12}$ is methylsulfonyl and $R^{13}$ is cyclopropyl.

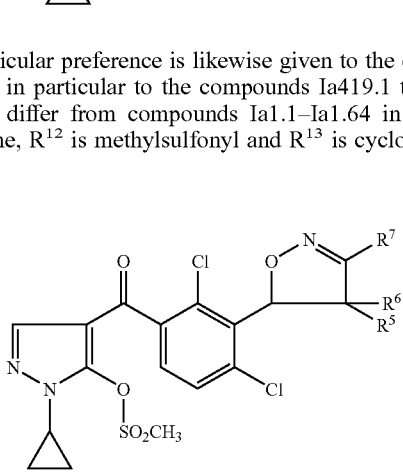

Ia419

Particular preference is likewise given to the compounds Ia420, in particular to the compounds Ia420.1 to Ia420.64 which differ from compounds Ia1.1–Ia1.64 in that $R^2$ is chlorine, $R^{12}$ is methylsulfonyl, $R^{13}$ is cyclopropyl and $R^{14}$ is methyl.

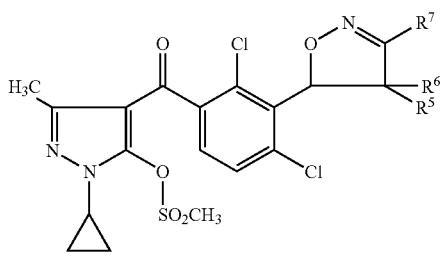

Ia420

Particular preference is likewise given to the compounds Ia421, in particular to the compounds Ia421.1 to Ia421.64 which differ from compounds Ia1.1–Ia1.64 in that $R^1$ is methyl, $R^2$ is chlorine, $R^{12}$ is methylsulfonyl and $R^{13}$ is cyclopropyl.

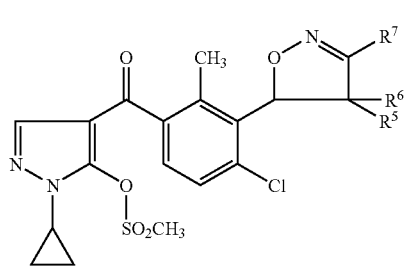

Ia421

Particular preference is likewise given to the compounds Ia422, in particular to the compounds Ia422.1 to Ia422.64 which differ from compounds Ia1.1–Ia1.64 in that $R^1$ and $R^{14}$ are methyl, $R^2$ is chlorine, $R^{12}$ is methylsulfonyl and $R^{13}$ is cyclopropyl.

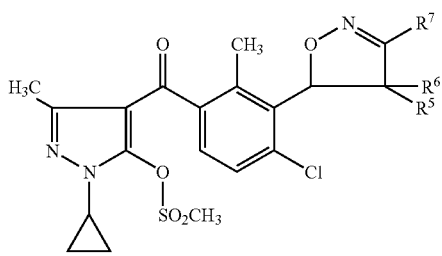

Ia422

Particular preference is likewise given to the compounds Ia423, in particular to the compounds Ia423.1 to Ia423.64 which differ from compounds Ia1.1–Ia1.64 in that $R^{12}$ is 4-methylphenylsulfonyl and $R^{13}$ is cyclopropyl.

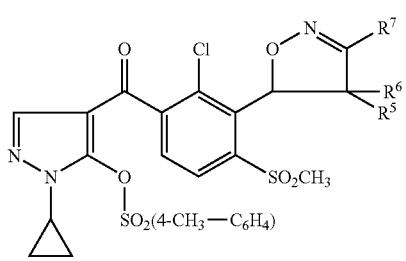

Ia423

Particular preference is likewise given to the compounds Ia424, in particular to the compounds Ia424.1 to Ia424.64 which differ from compounds Ia1.1–Ia1.64 in that $R^{12}$ is 4-methylphenylsulfonyl, $R^{13}$ is cyclopropyl and $R^{14}$ is methyl.

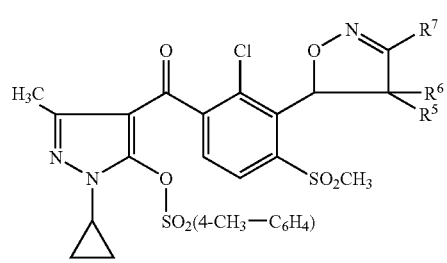

Ia424

Particular preference is likewise given to the compounds Ia425, in particular to the compounds Ia425.1 to Ia425.64 which differ from compounds Ia1.1–Ia1.64 in that $R^1$ is methyl, $R^{12}$ is 4-methylphenylsulfonyl and $R^{13}$ is cyclopropyl.

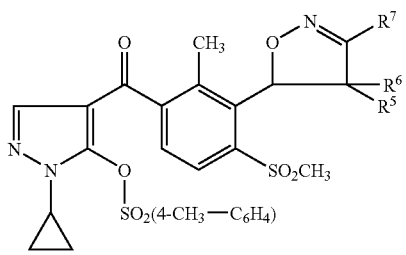

Ia425

Particular preference is likewise given to the compounds Ia426, in particular to the compounds Ia426.1 to Ia426.64 which differ from compounds Ia1.1–Ia1.64 in that $R^1$ and $R^{14}$ are methyl, $R^{12}$ is 4-methylphenylsulfonyl and $R^{13}$ is cyclopropyl.

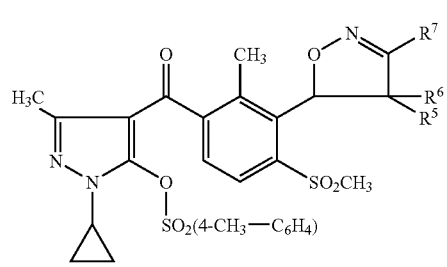

Ia426

Particular preference is likewise given to the compounds Ia427, in particular to the compounds Ia427.1 to Ia427.64 which differ from compounds Ia1.1–Ia1.64 in that $R^2$ is chlorine, $R^{12}$ is 4-methylphenylsulfonyl and $R^{13}$ is cyclopropyl.

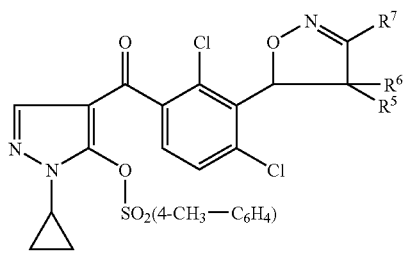

Ia427

Particular preference is likewise given to the compounds Ia428, in particular to the compounds Ia428.1 to Ia428.64 which differ from compounds Ia1.1–Ia1.64 in that $R^2$ is chlorine, $R^{12}$ is 4-methylphenylsulfonyl, $R^{13}$ is cyclopropyl and $R^{14}$ is methyl.

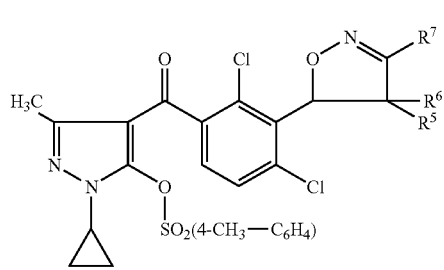

Ia428

Particular preference is likewise given to the compounds Ia429, in particular to the compounds Ia429.1 to Ia429.64 which differ from compounds Ia1.1–Ia1.64 in that $R^1$ is methyl, $R^2$ is chlorine, $R^{12}$ is 4-methylphenylsulfonyl and $R^{13}$ is cyclopropyl.

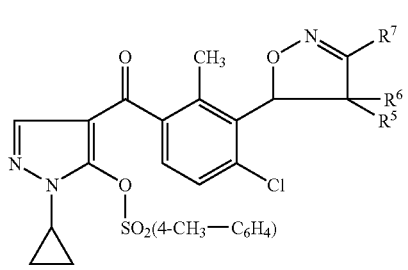

Ia429

Particular preference is likewise given to the compounds Ia430, in particular to the compounds Ia430.1 to Ia430.64 which differ from compounds Ia1.1–Ia1.64 in that $R^1$ and $R^{14}$ are methyl, $R^2$ is chlorine, $R^{12}$ is 4-methylphenylsulfonyl and $R^{13}$ is cyclopropyl.

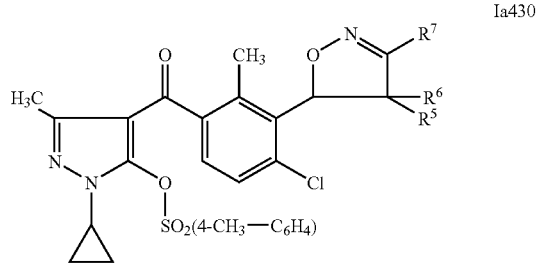

Ia430

The 3-(4,5-dihydroisoxazol-5-yl)benzoylpyrazoles of the formula I can be obtained by different routes, for example by the following processes:

Process A:

Reaction of pyrazoles of the formula II (where Z=H) with an activated benzoic acid IIIα or a benzoic acid IIIβ, which is preferably activated in situ, to give the acylation product, followed by rearrangement.

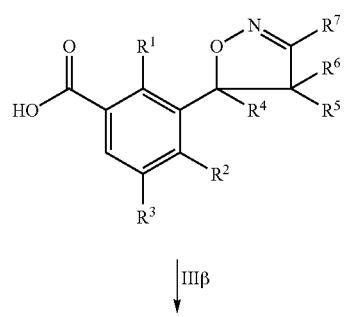

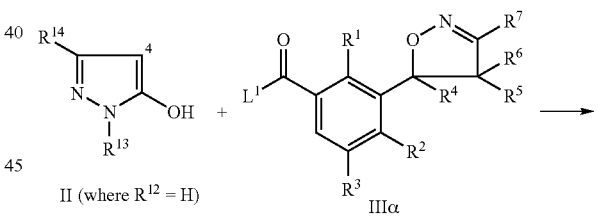

II (where $R^{12}$ = H)        IIIα

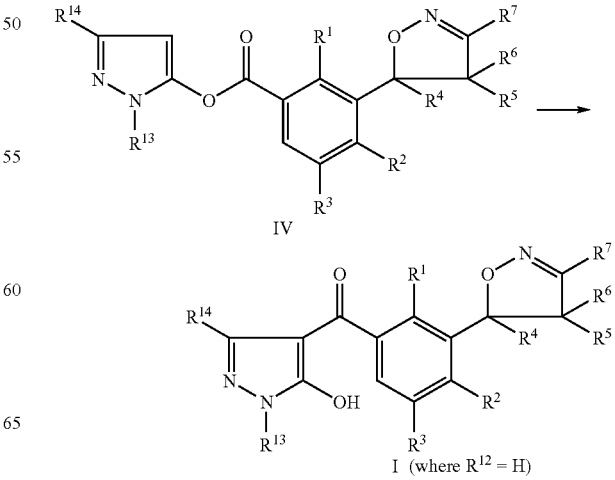

IV

I (where $R^{12}$ = H)

$L^1$ is a nucleophilically displaceable leaving group, such as halogen, for example bromine, chlorine, hetaryl, for example imidazolyl, pyridyl, carboxylate, for example acetate, trifluoroacetate, etc.

The activated benzoic acid can be employed directly, as in the case of the benzoyl halides, or be generated in situ, for example using dicyclohexylcarbodiimide, triphenylphosphane/azodicarboxylic acid esters, 2-pyridine disulfide/triphenylphosphane, carbonyldiimidazole, etc.

If appropriate, it may be advantageous to carry out the acylation reaction in the presence of a base. The reactants and the auxiliary base are advantageously employed in equimolar amounts. A slight excess of auxiliary base, for example from 1.2 to 1.5 molar equivalents, based on II, may be advantageous in some cases.

Suitable auxiliary bases are tertiary alkylamines, pyridine or alkali metal carbonates. Suitable solvents are, for example, chlorinated hydrocarbons, such as methylene chloride, 1,2-dichloroethane, aromatic hydrocarbons, such as toluene, xylene, chlorobenzene, ethers, such as diethyl ether, methyl tert-butyl ether, tetrahydrofuran, dioxane, dimethoxyethane, polar aprotic solvents, such as acetonitrile, dimethylformamide, dimethyl sulfoxide, or esters, such as ethyl acetate, or mixtures thereof.

If the activated carboxylic acid component used is a benzoyl halide, it may be advantageous to cool the reaction mixture to 0–10° C. when adding this reactant. The mixture is subsequently stirred at 20–100° C., preferably at 25–50° C., until the reaction has gone to completion. Work-up is carried out in a customary manner, for example by pouring the reaction mixture into water and extracting the product of value. Solvents which are particularly suitable for this purpose are methylene chloride, diethyl ether and ethyl acetate. The organic phase is dried and the solvent removed, and the crude ester can then be used for the rearrangement without further purification.

The rearrangement of the esters to the compounds of the formula I is advantageously carried out at 20–40° C. in a solvent and in the presence of a base and, if appropriate, using a cyano compound as catalyst.

Suitable solvents are, for example, acetonitrile, methylene chloride, 1,2-dichloroethane, dioxane, dimethoxyethane, ethyl acetate, toluene or mixtures thereof. Preferred solvents are acetonitrile, dioxane and dimethoxyethane.

Suitable bases are tertiary amines, such as triethylamine, pyridine or alkali metal carbonates, such as sodium carbonate, potassium carbonate, which are preferably employed in equimolar amounts or in excess of up to four times, based on the ester. Preference is given to using triethylamine or alkali metal carbonate, preferably in twice the equimolar ratio, based on the ester.

Suitable cyano compounds are inorganic cyanides, such as sodium cyanide, potassium cyanide, and organic cyano compounds, such as acetone cyanohydrin, trimethylsilyl cyanide. They are employed in an amount of from 1 to 50 mole percent, based on the ester. Preference is given to using acetone cyanohydrin or trimethylsilyl cyanide, for example in an amount of from 5 to 15, preferably 10, mole percent, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, dried and concentrated. (Examples of the preparation of esters of hydroxypyrazoles and the rearrangement of the esters are given, for example, in EP-A 282 944 and U.S. Pat. No. 4,643,757).

However, it may also be advantageous to generate the crude ester in situ and to carry out the rearrangement without isolation or purification of the ester.

Process B:

Reaction of 3-(4,5-dihydroisoxazol-5-yl)benzoylpyrazoles of the formula I (where $R^{12}$=H) with a compound of the formula V:

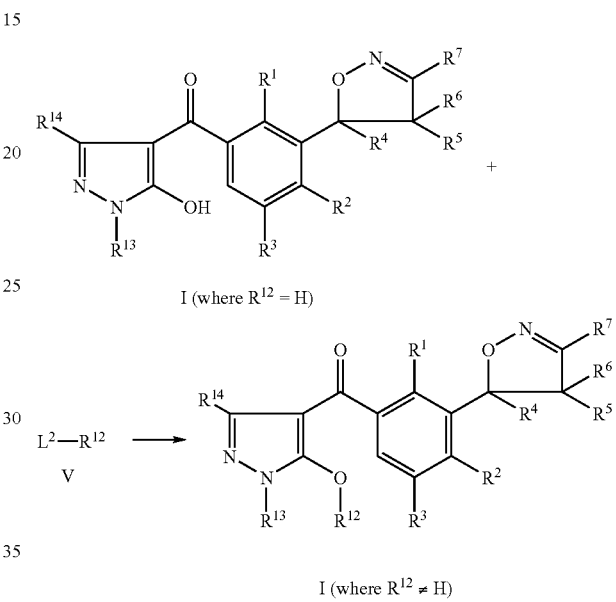

$L^2$ is a nucleophilically replaceable leaving groups, such as halogen, for example bromine, chlorine, hetaryl, for example imidazolyl, pyridyl, sulfonate.

The compounds of the formula V can be employed directly, such as, for example, in the case of the sulfonyl halides, sulfonic anhydrides, or be generated in situ, for example activated sulfonic acids (using sulfonic acid and dicyclohexylcarbonyldiimide, carbonyldiimidazole, etc.).

The starting materials are generally employed in eguimolar amounts. However, it can also be advantageous to use an excess of one component or the other.

If appropriate, it may be advantageous to carry out the reaction in the presence of a base. The reactants and the auxiliary base are then advantageously employed in equimolar amounts. An excess of auxiliary base, for example 1.5 to 3 molar equivalents, based on II, may be advantageous in certain cases.

Suitable auxiliary bases are tertiary alkylamines, such as triethylamine, pyridine, alkali metal carbonates, for example sodium carbonate, potassium carbonate, and alkali metal hydrides, for example sodium hydride. Preference is given to using triethylamine and pyridine.

Suitable solvents are, for example, chlorinated hydrocarbons, such as methylene chloride, 1,2-dichloroethane, aromatic hydrocarbons, for example toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide or esters, such as ethyl acetate, or mixtures thereof.

In general, the reaction temperature is in the range from 0° C. to the boiling point of the reaction mixture.

Work-up can be carried out in a manner known per se to afford the product.

The pyrazoles of the formula II (where $R^{12}$=H) used as starting materials are known or can be prepared by processes known per se (for example EP-A 240 001 and J. Prakt. Chem. 315 (1973), 383).

3-(4,5-Dihydroisoxazol-5-yl)benzoic acid derivatives of the formula III

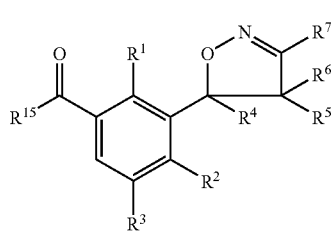

III where:

$R^1$, $R^2$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

$R^3$ is hydrogen, halogen or $C_1$–$C_6$-alkyl;

$R^4$ is hydrogen or $C_1$–$C_4$-alkyl;

$R^5$, $R^6$ are hydrogen, halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, di($C_1$–$C_4$-alkyl)aminoimino-$C_1$–$C_4$-alkyl, hydroxyimino-$C_1$–$C_4$-alkyl, $C_1$–$C_6$-alkoxyimino-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, where the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

or $R^5$ and $R^6$ together form a $C_2$–$C_6$-alkanediyl chain which may be mono- to tetrasubstituted by $C_1$–$C_4$-alkyl and/or may be interrupted by oxygen or an unsubstituted or $C_1$–$C_4$-alkyl-substituted nitrogen;

$R^7$ is halogen, cyano, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, amino, $C_1$–$C_6$-alkylamino, di($C_1$–$C_6$-alkyl)amino, di($C_1$–$C_4$-alkoxy)methyl, hydroxyimino-$C_1$–$C_4$-alkyl, $C_1$–$C_6$-alkoxyimino-$C_1$–$C_4$-alkyl or $COR^8$;

$R^8$ is hydrogen, $C_1$–$C_4$-alkyl, $C_1$–$C_4$-haloalkyl, hydroxyl, $C_1$–$C_4$-alkoxy, $C_1$–$C_4$-alkoxy-$C_2$–$C_4$-alkoxy, $C_1$–$C_4$-haloalkoxy, $C_3$–$C_6$-alkenyloxy, $C_3$–$C_6$-alkynyloxy or $NR^9R^{10}$;

$R^9$ is hydrogen or $C_1$–$C_4$-alkyl;

$R^{10}$ is $C_1$–$C_4$-alkyl;

$R^{15}$ is hydroxyl or a radical which can be removed by hydrolysis;

are novel.

Examples of radicals which can be removed by hydrolysis are alkoxy, phenoxy, alkylthio and phenylthio radicals, which may be substituted, halides, hetaryl radicals which are attached via nitrogen, amino and imino radicals, which may be substituted, etc.

Preference is given to 3-(4,5-dihydroisoxazol-5-yl)benzoyl halides of the formula IIIα' where $L^{1'}$=halogen (≙ III where $R^{15}$=halogen)

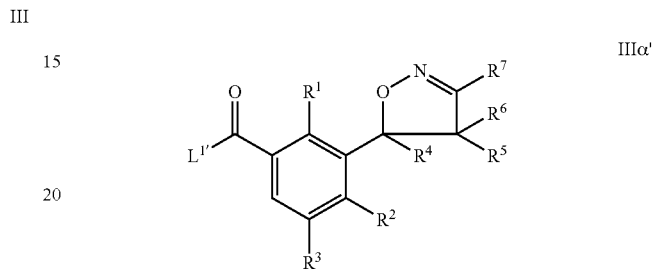

IIIα' where the variables $R^1$ to $R^7$ are as defined under formula III and $L^{1'}$ is halogen, in particular chlorine or bromine.

Preference is likewise given to 3-(4,5-dihydroisoxazol-5-yl)benzoic acids of the formula IIIβ (≙ III where $R^{15}$=hydroxyl)

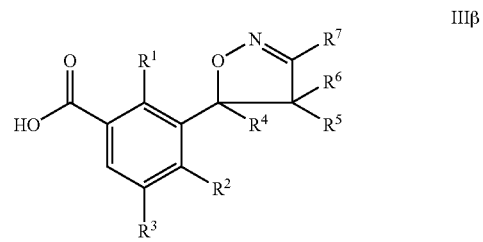

IIIβ where the variables $R^1$ to $R^7$ are as defined under formula III.

Preference is likewise given to 3-(4,5-dihydroisoxazol-5-yl)benzoic esters of the formula IIIγ (≙ III where $R^{15}$=$C_1$–$C_6$-alkoxy)

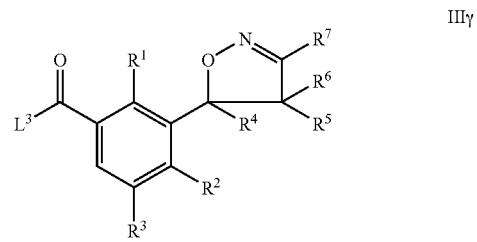

IIIγ where the variables $R^1$ to $R^7$ are as defined under III and $L^3$ is $C_1$–$C_6$-alkoxy.

The particularly preferred embodiments of the 3-(4,5-dihydroisoxazol-5-yl)benzoic acid derivatives of the formula III with respect to the variables $R^1$ to $R^7$ correspond to those of the 3-(4,5-dihydroisoxazol-5-yl)benzoylpyrazoles of the formula I.

The 3-(4,5-dihydroisoxazol-5-yl)benzoyl halides of the formula IIIα' (where $L^{1'}$=Cl, Br) can be prepared in a manner known per se by reacting the 3-(4,5-dihydroisoxazol-5-yl)benzoic acids of the formula IIIβ with halogenating agents, such as thionyl chloride, thionyl bromide, phosgene, diphosgene, triphosgene, oxalyl chloride, oxalyl bromide.

The 3-(4,5-dihydroisoxazol-5-yl)benzoic acids of the formula IIIβ can be prepared in a known manner by acidic or basic hydrolysis from the corresponding esters of the formula IIIγ ($L^3$=$C_1$–$C_6$-alkoxy).

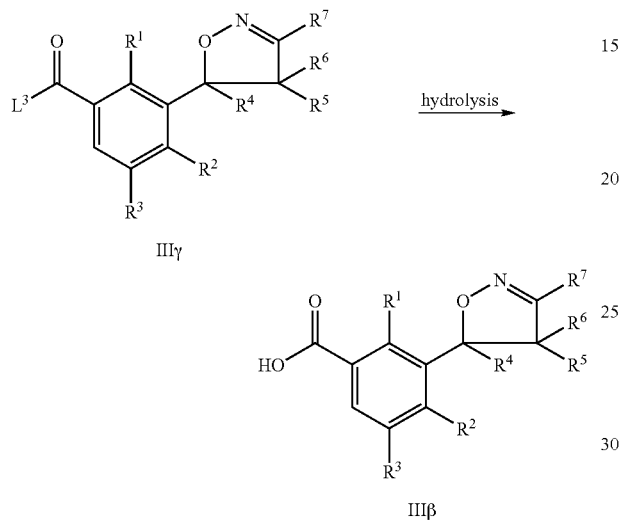

Likewise, the 3-(4,5-dihydroisoxazol-5-yl)benzoic acids of the formula IIIβ can be obtained by reacting the corresponding halogen-substituted compounds of the formula VI ($L^4$=Hal), in particular the iodine or bromine compounds, in the presence of a palladium, nickel, cobalt or rhodium transition metal catalyst and a base with carbon monoxide and water under elevated pressure.

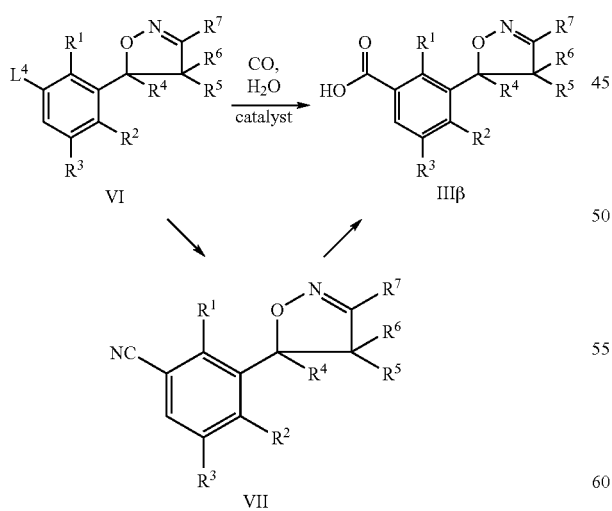

Furthermore, it is possible to convert, by Rosenmund-von Braun-reaction, compounds of the formula VI into the corresponding nitriles of the formula VII (cf., for example, Org. Synth. Vol. III (1955), 212), and to convert these by subsequent hydrolysis into the compounds of the formula IIIβ.

The compounds of the formulae VI and VII

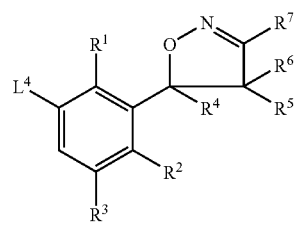

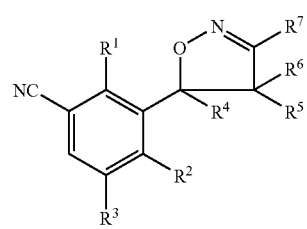

where:
$R^1$, $R^2$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

$R^3$ is hydrogen, halogen or $C_1$–$C_6$-alkyl;

$R^4$ is hydrogen or $C_1$–$C_4$-alkyl;

$R^5$, $R^6$ are hydrogen, halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, di($C_1$–$C_4$-alkyl)aminoimino-$C_1$–$C_4$-alkyl, hydroxyimino-$C_1$–$C_4$-alkyl, $C_1$–$C_6$-alkoxyimino-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, where the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

or $R^5$ and $R^6$ together form a $C_2$–$C_6$-alkanediyl chain which may be mono- to tetrasubstituted by $C_1$–$C_4$-alkyl and/or may be interrupted by oxygen or an unsubstituted or $C_1$–$C_4$-alkyl-substituted nitrogen;

$R^7$ is halogen, cyano, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, amino, $C_1$–$C_6$-alkylamino, di($C_1$–$C_6$-alkyl)amino, di-($C_1$–$C_4$-alkoxy)methyl, hydroxyimino-$C_1$–$C_4$-alkyl, $C_1$–$C_6$-alkoxyimino-$C_1$–$C_4$-alkyl or $COR^8$;

$R^8$ is hydrogen, $C_1$–$C_4$-alkyl, $C_1$–$C_4$-haloalkyl, hydroxyl, $C_1$–$C_4$-alkoxy, $C_1$–$C_4$-alkoxy-$C_2$–$C_4$-alkoxy, $C_1$–$C_4$-haloalkoxy, $C_3$–$C_6$-alkenyloxy, $C_3$–$C_6$-alkynyloxy or $NR^9R^{10}$;

$R^9$ is hydrogen or $C_1$–$C_4$-alkyl;

$R^{10}$ is $C_1$–$C_4$-alkyl;

$L^4$ is halogen;

are likewise novel.

The particular embodiments of the compounds of the formulae VI and VII with respect to the variables $R^1$ to $R^7$ correspond to those of the 3-(4,5-dihydroisoxazol-5-yl)benzoylpyrazoles of the formula I.

The esters of the formula IIIγ and the halogen compounds of the formula VI can be prepared by 1,3-dipolar cycloaddition of nitrile oxides to appropriate alkenes of the formula VIII and IX, respectively.

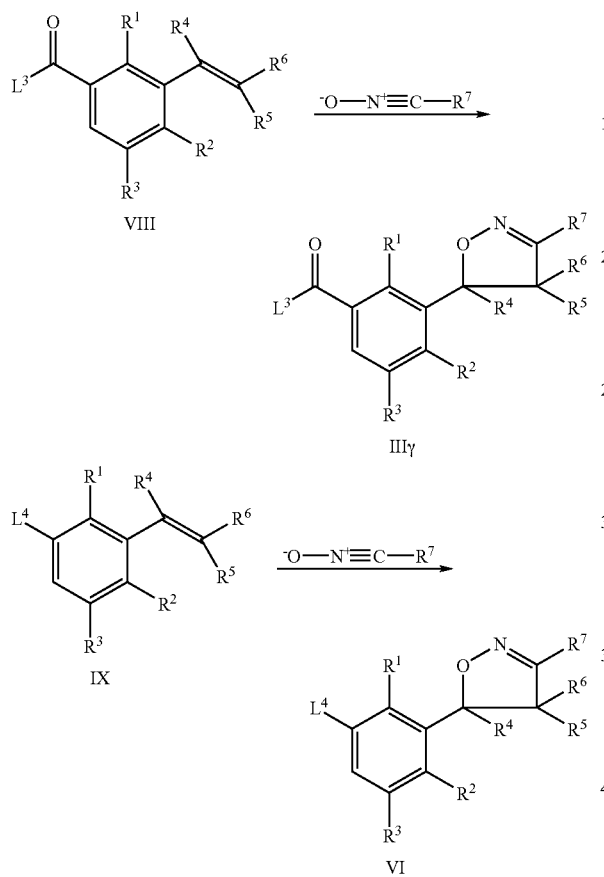

The nitrile oxides are prepared in situ in a manner known per se. Suitable starting materials are, for example, aldoximes (cf., for example, Houben-Weyl X5, p. 858ff.) or nitroalkanes (cf., for example, Houben-Weyl E5/2, p. 1594ff.). The synthesis the compounds of the formulae VIII and IX is known (cf., for example, WO 98/50337 or WO 98/50366), or is carried out analogously to processes known from the literature.

PREPARATION EXAMPLES

4-[2-Chloro-3-(3-methyl-4,5-dihydroisoxazol-5-yl)-4-methylsulfonylbenzoyl]-5-hydroxy-1-methyl-1H-pyrazole (Compound 2.8)

At 0–5° C., a solution of 6.7 g (20 mmol) of 2-chloro-3-(3-methyl-4,5-dihydroisoxazol-5-yl)-4-methylsulfonylbenzoyl chloride in 80 ml of dimethoxyethane was added dropwise to a solution of 2.0 g (20 mmol) of 5-hydroxy-1-methylpyrazole and 3.3 g (24 mmol) of potassium carbonate in 30 ml of anhydrous dimethoxyethane. After 12 hours of stirring at room temperature, a further 8.2 g (60 mmol) of potassium carbonate were added, and the batch was refluxed for six hours. After cooling, the reaction mixture was stirred into 1 l of water and extracted with methylene chloride. The aqueous phase was then adjusted to pH 4 using 10% strength hydrochloric acid and extracted repeatedly with methylene chloride, with readjustment of the pH. The organic phase was dried and the solvent removed, giving 5.3 g (13 mmol, 67%) of the desired compound.

M.p.: >215° C.

4-[2-Chloro-3-(3-methyl-4,5-dihydroisoxazol-5-yl)-4-methylsulfonylbenzoyl]-5-hydroxy-1-cyclopropyl-1H-pyrazole (Compound 2.36)

At 0–5° C., a solution of 1.0 g (3 mmol) of 2-chloro-3-(3-methyl-4,5-dihydroisoxazol-5-yl)-4-methylsulfonylbenzoyl chloride in 50 ml of dimethoxyethane was added dropwise to a solution of 0.47 g (3 mmol) of 5-hydroxy-1-cyclopropylpyrazole and 0.5 g (3.6 mmol) of potassium carbonate in 36 ml of anhydrous dimethoxyethane. After 12 hours of stirring at room temperature, a further 1.0 g (7.2 mmol) of potassium carbonate were added and the batch was refluxed for 6 hours. After cooling, the reaction mixture was stirred into 600 ml of water and extracted with methylene chloride. The aqueous phase was then adjusted to pH 4 using 10% strength hydrochloric acid and extracted with methylene chloride. Drying of the organic phase and removal of the solvent gave 0.8 g (1.8 mmol, 63%) of the desired compound.

M.p.: >220° C.

In addition to the compounds mentioned above, further derivatives of the formula I which were prepared or are preparable in an analogous manner are listed in Table 2.

TABLE 2

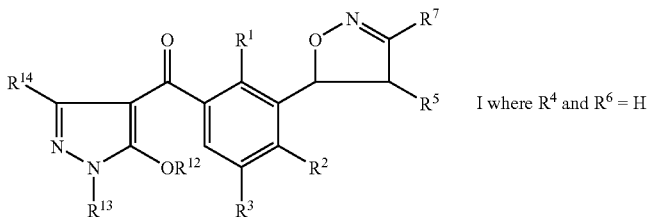

I where $R^4$ and $R^6$ = H

| No. | $R^1$ | $R^2$ | $R^3$ | $R^5$ | $R^7$ | $R^{12}$ | $R^{13}$ | $R^{14}$ | Physical data m.p. [° C.] |
|---|---|---|---|---|---|---|---|---|---|
| 2.1 | Cl | Cl | H | H | $C(CH_3)_3$ | H | $CH_3$ | H | 92–96 |
| 2.2 | Cl | $SO_2CH_3$ | H | H | $C(CH_3)_3$ | H | $CH_3$ | H | 116–120 |

TABLE 2-continued

I where $R^4$ and $R^6$ = H

| No. | $R^1$ | $R^2$ | $R^3$ | $R^5$ | $R^7$ | $R^{12}$ | $R^{13}$ | $R^{14}$ | Physical data m.p. [° C.] |
|---|---|---|---|---|---|---|---|---|---|
| 2.3 | Cl | Cl | H | H | COOC$_2$H$_5$ | H | CH$_3$ | H | 98–104 |
| 2.4 | Cl | SO$_2$CH$_3$ | H | H | COOCH$_3$ | H | CH$_3$ | H | 130–135 |
| 2.5 | Cl | Cl | H | H | COOH | H | CH$_3$ | H | 96–104 |
| 2.6 | Cl | Cl | H | H | CH$_3$ | H | CH$_3$ | H | 83–98 |
| 2.7 | CH$_3$ | SO$_2$CH$_3$ | H | H | CH$_3$ | H | CH$_3$ | H | 216–223 |
| 2.8 | Cl | SO$_2$CH$_3$ | H | H | CH$_3$ | H | CH$_3$ | H | >215 |
| 2.9 | Cl | SO$_2$CH$_3$ | H | H | CH$_3$ | H | CH(CH$_3$)$_2$ | H | 241–244 |
| 2.10 | Cl | Cl | H | CH$_3$ | C(CH$_3$)$_3$ | H | CH$_3$ | H | |
| 2.11 | Cl | Cl | H | CH$_3$ | CH$_3$ | H | CH$_3$ | H | |
| 2.12 | Cl | SO$_2$CH$_3$ | H | H | CH(OC$_2$H$_5$)$_2$ | H | CH$_3$ | H | 87–98 |
| 2.13 | Cl | SO$_2$CH$_3$ | H | H | COCH$_3$ | H | CH$_3$ | H | |
| 2.14 | Cl | SO$_2$CH$_3$ | H | OCH$_3$ | CH$_3$ | H | CH$_3$ | H | |
| 2.15 | Cl | SO$_2$CH$_3$ | H | H | Cl | H | CH$_3$ | H | |
| 2.16 | Cl | SO$_2$CH$_3$ | H | H | OCH$_3$ | H | CH$_3$ | H | |
| 2.17 | Cl | SO$_2$CH$_3$ | H | H | SCH$_3$ | H | CH$_3$ | H | |
| 2.18 | Cl | SO$_2$CH$_3$ | H | H | SOCH$_3$ | H | CH$_3$ | H | |
| 2.19 | Cl | SO$_2$CH$_3$ | H | H | SO$_2$CH$_3$ | H | CH$_3$ | H | |
| 2.20 | Cl | SO$_2$CH$_3$ | H | H | NH$_2$ | H | CH$_3$ | H | |
| 2.21 | Cl | SO$_2$CH$_3$ | H | H | NHCH$_3$ | H | CH$_3$ | H | |
| 2.22 | Cl | SO$_2$CH$_3$ | H | H | N(CH$_3$)$_2$ | H | CH$_3$ | H | |
| 2.23 | Cl | SO$_2$CH$_3$ | H | H | C$_2$H$_5$ | H | CH$_3$ | H | |
| 2.24 | Cl | SO$_2$CH$_3$ | H | H | CH(CH$_3$)$_2$ | H | CH$_3$ | H | |
| 2.25 | Cl | SO$_2$CH$_3$ | H | H | CH$_3$ | CO(2-F—C$_6$H$_4$) | CH$_3$ | H | 62–65 |
| 2.26 | Cl | SO$_2$CH$_3$ | H | H | CH$_3$ | H | C$_2$H$_5$ | H | 230–231 |
| 2.27 | Cl | SO$_2$CH$_3$ | H | H | CH$_3$ | H | C(CH$_3$)$_3$ | H | |
| 2.28 | Cl | SO$_2$CH$_3$ | H | H | CH$_3$ | H | CH$_3$ | CH$_3$ | |
| 2.29 | CH$_3$ | SO$_2$CH$_3$ | H | H | CH$_3$ | H | C$_2$H$_5$ | H | 213–215 |
| 2.30 | CH$_3$ | SO$_2$CH$_3$ | H | H | CH$_3$ | H | CH(CH$_3$)$_2$ | H | 217–221 |
| 2.31 | CH$_3$ | SO$_2$CH$_3$ | H | H | CH$_3$ | H | C(CH$_3$)$_3$ | H | 210–213 |
| 2.32 | CH$_3$ | SO$_2$CH$_3$ | H | H | CH$_3$ | H | CH$_3$ | CH$_3$ | 192–196 |
| 2.33 | CH$_3$ | SO$_2$CH$_3$ | H | H | CH$_3$ | CH$_2$—C$_6$H$_5$ | CH$_3$ | H | Oil |
| 2.34 | Cl | SO$_2$CH$_3$ | H | H | COOCH$_3$ | CO(2-F—C$_6$H$_4$) | CH$_3$ | H | Oil |
| 2.35 | CH$_3$ | SO$_2$CH$_3$ | H | H | CH(CH$_3$)$_2$ | H | CH$_3$ | H | 210–211 |
| 2.36 | Cl | SO$_2$CH$_3$ | H | H | CH$_3$ | H | cyclo-C$_3$H$_5$ | H | >220 |
| 2.37 | CH$_3$ | SO$_2$CH$_3$ | H | H | CH(CH$_3$)$_2$ | H | CH(CH$_3$)$_2$ | H | 233–237 |
| 2.38 | CH$_3$ | SO$_2$CH$_3$ | H | H | CH(CH$_3$)$_2$ | H | CH$_3$ | CH$_3$ | 180–183 |
| 2.39 | Cl | Cl | H | H | CH$_3$ | H | CH$_2$CH$_3$ | H | 63–66 |
| 2.40 | Cl | Cl | H | H | CH$_3$ | H | (CH$_2$)$_2$CH$_3$ | H | 205–208 |
| 2.41 | Cl | Cl | H | H | CH$_3$ | H | CH$_3$ | CH$_3$ | 89–95 |
| 2.42 | Cl | Cl | H | H | CH$_3$ | H | cyclo-C$_3$H$_5$ | H | 159–163 |
| 2.43 | OCH$_3$ | SO$_2$CH$_3$ | H | H | CH$_3$ | H | CH$_3$ | H | 165–175 |
| 2.44 | OCH$_3$ | SO$_2$CH$_3$ | H | H | CH$_3$ | H | cyclo-C$_3$H$_5$ | H | 160–165 |
| 2.45 | OCH$_3$ | SO$_2$CH$_3$ | H | H | CH$_3$ | H | CH(CH$_3$)$_2$ | H | 140–145 |
| 2.46 | Cl | Cl | H | H | CH$_3$ | CH$_2$—C$_6$H$_5$ | CH$_3$ | CH$_3$ | 50–55 |
| 2.47 | Cl | Cl | H | H | CH$_3$ | CH$_2$—C$_6$H$_5$ | cyclo-C$_3$H$_5$ | H | oil |
| 2.48 | Cl | Cl | H | H | CH$_3$ | CH$_2$—C$_6$H$_5$ | CH$_2$CH$_3$ | H | oil |
| 2.49 | Cl | SO$_2$CH$_3$ | H | H | CH$_3$ | CH$_2$—C$_6$H$_5$ | C(CH$_3$)$_3$ | H | 70–72 |
| 2.50 | Cl | SO$_2$CH$_3$ | H | H | CH$_3$ | CH$_2$—C$_6$H$_5$ | CH(CH$_3$)$_2$ | cyclo-C$_3$H$_5$ | 76–82 |
| 2.51 | Cl | SO$_2$CH$_3$ | H | H | CH$_3$ | H | CH(CH$_3$)$_2$ | CH(CH$_3$)$_2$ | oil |
| 2.52 | Cl | SO$_2$CH$_3$ | H | H | CH$_3$ | CH$_2$—C$_6$H$_5$ | CH(CH$_3$)$_2$ | H | oil |
| 2.53 | CH$_3$ | SO$_2$CH$_3$ | H | H | CH$_3$ | H | cyclo-C$_3$H$_5$ | H | 189–191 |
| 2.54 | CH$_3$ | SO$_2$CH$_3$ | H | H | CH$_3$ | CH$_2$—CO(4-CH$_3$—C$_6$H$_4$) | CH(CH$_3$)$_2$ | H | 148–150 |
| 2.55 | Cl | Cl | H | H | CH$_3$ | H | CH$_2$CF$_3$ | CH$_3$ | 46–55 |
| 2.56 | CH$_3$ | SO$_2$CH$_3$ | H | H | CH$_3$ | SO$_2$-(4-CH$_3$—C$_6$H$_4$) | CH(CH$_3$)$_2$ | H | 212–213 |
| 2.57 | CH$_3$ | SO$_2$CH$_3$ | H | H | CH$_3$ | CH$_2$—C$_6$H$_5$ | CH(CH$_3$)$_2$ | H | 91–95 |
| 2.58 | Cl | Cl | H | H | CH$_3$ | CH$_2$—C$_6$H$_5$ | CH$_2$CF$_3$ | H | oil |
| 2.59 | Cl | Cl | H | H | CH$_3$ | H | CH$_2$CF$_3$ | H | 75–80 |
| 2.60 | Cl | Cl | H | H | CH$_3$ | CH$_2$—CO(4-CH$_3$—C$_6$H$_4$) | cyclo-C$_3$H$_5$ | H | 70–75 |
| 2.61 | Cl | Cl | H | H | CH$_3$ | SO$_2$-(4-CH$_3$—C$_6$H$_4$) | cyclo-C$_3$H$_5$ | H | 67–75 |
| 2.62 | CH$_3$ | SO$_2$CH$_3$ | H | H | CH$_3$ | CH$_2$-(3-thienyl) | CH$_3$ | H | oil |
| 2.63 | CH$_3$ | SO$_2$CH$_3$ | H | H | CH$_3$ | CH$_2$-(3-thienyl) | CH(CH$_3$)$_2$ | H | |
| 2.64 | CH$_3$ | SO$_2$CH$_3$ | H | H | CH$_3$ | CH$_2$C≡CH | CH$_3$ | H | oil |
| 2.65 | CH$_3$ | SO$_2$CH$_3$ | H | H | CH$_3$ | CH$_2$CO(4-CH$_3$—C$_6$H$_4$) | CH$_3$ | H | 170–176 |

TABLE 2-continued

[Structure: I where R⁴ and R⁶ = H]

| No. | R¹ | R² | R³ | R⁵ | R⁷ | R¹² | R¹³ | R¹⁴ | Physical data m.p. [° C.] |
|---|---|---|---|---|---|---|---|---|---|
| 2.66 | CH₃ | SO₂CH₃ | H | H | CH₃ | CH₂—C₆H₅ | cyclo-C₃H₅ | H | 78–82 |
| 2.67 | CH₃ | SO₂CH₃ | H | H | CH₃ | CH₂-(3-thienyl) | cyclo-C₃H₅ | H | |

The syntheses of some starting materials are given below:

Methyl 2,4-dichloro-3-(3-tert-butyl-4,5-dihydroisoxazol-5-yl)benzoate

At room temperature, 17 ml of a 12% strength aqueous sodium hypochlorite solution were added dropwise with vigorous stirring to a solution of 2.6 g (10 mmol) of methyl 2,4-dichloro-3-ethenylbenzoate and 1 g (10 mmol) of 2,2-dimethylpropionaldoxime in 100 ml of dichloromethane. Twice, in each case after 2 hours of stirring, a further 0.5 g (5 mmol) of the oxime and 9 ml of the hypochlorite solution were added. The reaction mixture was stirred at room temperature for a further 12 hours and then stirred into 350 ml of water. After extraction with dichloromethane, drying and removal of the solvent, the residue was chromatographed.

Yield: 1.5 g (45% of theory) of a yellow resin

Methyl 2-chloro-3-(3-ethoxycarbonyl-4,5-dihydroisoxazol-5-yl)-4-methyl-sulfonylbenzoate At room temperature, 6.4 ml (46 mmol) of triethylamine were slowly added dropwise to a solution of 8.5 g (31 mmol) of methyl 2-chloro-3-ethenyl-4-methylsulfonylbenzoate and 7.2 g (46 mmol) of ethyl 2-chloro-2-hydroxyiminoacetate in 200 ml of dichloromethane. 3 further portions of in each case 4.8 g (31 mmol) of ethyl 2-chloro-2-hydroxyiminoacetate and then 4.3 ml (31 mmol) of triethylamine were added, in each case after 2 hours of stirring. The reaction mixture was stirred at room temperature for another 12 hours and then stirred into 600 ml of water. After extraction with dichloromethane, drying and removal of the solvent, the residue was chromatographed.

Yield: 5.7 g (47% of theory) of a clear resin.

2-Chloro-3-(3-methyl-4,5-dihydroisoxazol-5-yl)-4-methylsulfonylbenzoic acid a) Methyl 2-chloro-3-(3-methyl-4,5-dihydroisoxazol-5-yl)-4-methylsulfonylbenzoate.

A spatula tip of 4-dimethylaminopyridine was added to a solution of 40 g (145 mmol) of methyl 2-chloro-3-ethenyl-4-methylsulfonylbenzoate and 50 g (220 mmol) of di-tert-butyl dicarbonate in 300 ml of acetonitrile, and 50 g (640 mmol) of nitroethane were then slowly added dropwise. The mixture was stirred at room temperature for 12 hours, and a further 32.8 g (145 mmol) of di-tert-butyl dicarbonate and 22.9 g (290 mmol) of nitroethane were then added. After a further 12 hours, the solvent was distilled off and the residue was digested with ethyl acetate. The mixture was filtered off with suction, giving 32.1 g of the desired compound. A further 6.3 g were obtained from the mother liquor after removal of the solvent, followed by chromatography.

Yield: 39.4 g (82% of theory)
M.p.: 175° C.

b) 2-Chloro-3-(3-methyl-4,5-dihydroisoxazol-5-yl)-4-methylsulfonylbenzoic acid 69.4 g (174 mmol) of 10% strength aqueous sodium hydroxide solution were added to a solution of 38.4 g (116 mmol) of methyl 2-chloro-3-(3-methyl-4,5-dihydroisoxazol-5-yl)-4-methylsulfonylbenzoate in 400 ml of methanol and 400 ml of tetrahydrofuran. The mixture was stirred at room temperature for 12 hours, the solvent volume was reduced to half of the original volume and the mixture was poured into 1 l of water. Using 10% strength hydrochloric acid the pH was adjusted to 1 and the resulting precipitate was filtered off with suction.

Yield: 35.2 g (96% of theory)
M.p.: >220° C.

2-Methyl-3-(3-methyl-4,5-dihydroisoxazol-5-yl)-4-methylsulfonylbenzoic acid a) 2-Methyl-3-(3-methyl-4,5-dihydroisoxazol-5-yl)-4-methylsulfonylbromobenzene A spatula tip of 4-dimethylaminopyridine was added to a solution of 13.6 g (50 mmol) of 2-methyl-3-ethenyl-4-methylsulfonylbromobenzene and 16.7 g (74 mmol) of di-tert-butyl dicarbonate in 100 ml of acetonitrile, and 17.9 g (229 mmol) of nitroethane were then slowly added dropwise. The mixture was stirred at room temperature for 6 hours, and a further 11.1 g (50 mmol) of di-tert-butyl dicarbonate and 7.8 g (100 mmol) of nitroethane were then added, and the mixture was stirred at room temperature for 12 hours. The solvent was removed and the residue was chromatographed.

Yield: 6.4 g (38% of theory)

b) 2-Methyl-3-(3-methyl-4,5-dihydroisoxazol-5-yl)-4-methylsulfonylbenzoic acid 6.4 g (19 mmol) of 2-methyl-3-(3-methyl-4,5-dihydroisoxazol-5-yl)-4-methylsulfonylbromobenzene were dissolved in 65 ml of toluene and 30 ml of water and admixed with 240 mg (1 mmol) of palladium acetate, 1.1 g (4 mmol) of tricyclohexylphosphane, 810 mg (19 mmol) of lithium chloride and 5.4 ml (38 mmol) of triethylamine. The resulting solution was then stirred in an autoclave at 140° C. and under a carbon monoxide pressure of 20 bar for 36 hours. After cooling and venting, insoluble components were filtered off and the phases were separated. The organic phase was then extracted twice with water containing a little triethylamine. The combined aqueous phases were then adjusted to pH 1 using 10% hydrochloric acid, and the resulting precipitate was filtered off.

Yield: 2.5 g (44% of theory)

M.p.: 199–205° C.

In addition to the compounds described above, Table 3 below lists further 3-(4,5-dihydroisoxazol-5-yl)benzoic acid derivatives of the formula III which are prepared or are preparable in a similar manner.

TABLE 3

I where $R^4$ and $R^6$ = H

| No. | $R^1$ | $R^2$ | $R^3$ | $R^5$ | $R^7$ | $R^{15}$ | Physical data [° C.] |
|-----|-------|-------|-------|-------|-------|----------|----------------------|
| 3.1 | Cl | Cl | H | H | $CH_3$ | $OCH_3$ | Resin |
| 3.2 | Cl | Cl | H | H | $CH_3$ | OH | Resin |
| 3.3 | Cl | Cl | H | H | $C(CH_3)_3$ | $OCH_3$ | Resin |
| 3.4 | Cl | Cl | H | H | $C(CH_3)_3$ | OH | |
| 3.5 | Cl | $SO_2CH_3$ | H | H | $C(CH_3)_3$ | $OCH_3$ | 54–55 |
| 3.6 | Cl | $SO_2CH_3$ | H | H | $C(CH_3)_3$ | OH | 97–100 |
| 3.7 | Cl | Cl | H | H | COOEt | $OCH_3$ | Oil |
| 3.8 | Cl | Cl | H | H | COOEt | OH | |
| 3.9 | Cl | $SO_2CH_3$ | H | H | COOEt | $OCH_3$ | Resin |
| 3.10 | Cl | $SO_2CH_3$ | H | H | COOEt | OH | 82–90 |
| 3.11 | Cl | Cl | H | H | COOH | OH | 182–183 |
| 3.12 | Cl | Cl | H | H | $CF_3$ | $OCH_3$ | Oil |
| 3.13 | Cl | Cl | H | H | $CF_3$ | OH | |
| 3.14 | Cl | $SO_2CH_3$ | H | H | $CH_3$ | $OCH_3$ | 175 |
| 3.15 | Cl | $SO_2CH_3$ | H | H | $CH_3$ | OH | >220 |
| 3.16 | $CH_3$ | $SO_2CH_3$ | H | H | $CH_3$ | $OCH_3$ | 120–121 |
| 3.17 | $CH_3$ | $SO_2CH_3$ | H | H | $CH_3$ | OH | 199–205 |
| 3.18 | Cl | $SO_2CH_3$ | H | H | $CH(OC_2H_5)_2$ | $OCH_3$ | Resin |
| 3.19 | Cl | $SO_2CH_3$ | H | H | $CH(OC_2H_5)_2$ | OH | |
| 3.20 | Cl | $SO_2CH_3$ | H | H | CHO | $OCH_3$ | |
| 3.21 | Cl | $SO_2CH_3$ | H | H | CHO | OH | |
| 3.22 | Cl | Cl | H | $CH_3$ | $C(CH_3)_3$ | $OCH_3$ | |
| 3.23 | Cl | Cl | H | $CH_3$ | $C(CH_3)_3$ | OH | |
| 3.24 | Cl | Cl | H | H | $COCH_3$ | $OCH_3$ | |
| 3.25 | Cl | Cl | H | H | $COCH_3$ | OH | |
| 3.26 | Cl | Cl | H | H | Cl | $OCH_3$ | |
| 3.27 | Cl | Cl | H | H | Cl | OH | |

The 3-(4,5-dihydroisoxazol-5-yl)benzoylpyrazoles of the formula I and their agriculturally useful salts are suitable as herbicides, both in the form of isomer mixtures and in the form of the pure isomers. The herbicidal compositions comprising compounds of the formula I effect very good control of vegetation on non-crop areas, especially at high rates of application. In crops such as wheat, rice, maize, soybeans and cotton they act against broad-leaved weeds and grass weeds without damaging the crop plants substantially. This effect is observed especially at low rates of application.

Depending on the application method in question, the compounds of the formula I, or herbicidal compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rusticaa), Olea europaea, Oryza sativa, Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera and Zea mays.

Moreover, the compounds of the formula I can also be used in crops which tolerate the action of herbicides due to breeding including genetic engineering methods.

The compounds of the formula I, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

The herbicidal compositions comprise a herbicidally active amount of at least one compound of the formula I or of an agriculturally useful salt of I and auxiliaries conventionally used for the formulation of crop protection products.

Suitable inert auxiliaries are essentially:

mineral oil fractions of medium to high boiling point such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, for example amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the 3-(4,5-dihydroisoxazol-5-yl) benzoylpyrazoles, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants (adjuvants) are the alkali metal, alkaline earth metal and ammonium salts of aromatic sulfonic acids, for example ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl, tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Solid carriers are mineral earths such as silicas, silica gels, silicates, talc, kaolin, limestone, lime, chalk, bolus, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the compounds of the formula I in the ready-to-use products can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples below illustrate the preparation of such products:

I. 20 parts by weight of the compound No. 2.7 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 2.7 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 2.7 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 2.7 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 2.7 are mixed with 97 parts by weight of finely divided kaolin. This gives a dust which comprises 3% by weight of the active ingredient.

VI. 20 parts by weight of the active ingredient No. 2.7 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active ingredient No. 2.7 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of active ingredient No. 2.7 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I, or the herbicidal compositions comprising them, can be applied pre- or post-emergence. If the active ingredients are less well tolerated by certain crop plants, application techniques may be used in which the herbicidal compositions are sprayed, with the aid of the spray apparatus, in such a way that they come into as little contact as possible, if any, with the leaves of the sensitive crop plants while reaching the leaves of undesirable plants which grow underneath, or the bare soil (post-directed, lay-by).

Depending on the intended aim of the control measures, the season, the target plants and the growth stage, the application rates of the compound of the formula I are from 0.001 to 3.0, preferably 0.01 to 1.0 kg/ha of active substance (a.s.).

To widen the spectrum of action and to achieve synergistic effects, the 3-(4,5-dihydroisoxazol-5-yl)benzoylpyrazoles of the formula I can be mixed and applied jointly with a large number of representatives of other groups of herbicidally or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, aryloxy-/hetaryloxyalkanic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofuranes, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolcarboxamides and uracils.

Moreover, it may be advantageous to apply the compounds of the formula I, alone or in combination with other herbicides, in the form of a mixture with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

USE EXAMPLES

The herbicidal action of the 3-(4,5-dihydroisoxazol-5-yl) benzoylpyrazoles of the formula I was demonstrated by the following greenhouse experiments:

The culture containers used were plastic flowerpots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants unless this was adversely affected by the active ingredients.

For the post-emergence treatment, the test plants were grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 125 or 62.5 g/ha a.s. (active substance).

Depending on the species, the plants were kept at from 10 to 25° C. and 20 to 35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific name | Common name |
|---|---|
| Avena fatua | wild oat |
| Bromus inermis | brome |
| Matricaria chamomilla | wild chamomile |
| Matricaria inodora | false chamomile |
| Tritricum aestivum | spring wheat |

At an application rate of 125 or 62.5 g/ha of a.s., the compound 2.7 showed very good activity against the above-mentioned harmful plants and was compatible with spring wheat.

In contrast, at the same application rates, the comparative compound A (compound 20 from Table 1) known from WO 97/41118 caused damage in the crop plant spring wheat, and had a weaker herbicidal activity against the harmful plants mentioned.

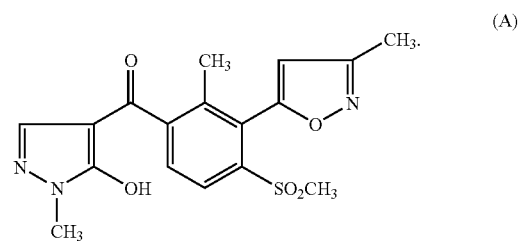

What is claimed is:

1. A 3(4,5-dihydroisoxazol-5-yl)benzoylpyrazole of the formula I

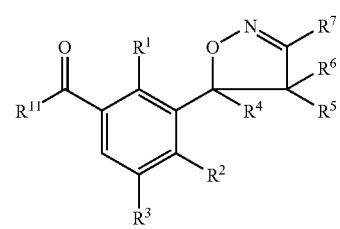

where:
$R^1$, $R^2$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

$R^3$ is hydrogen, halogen or $C_1$–$C_6$-alkyl;

$R^4$ is hydrogen or $C_1$–$C_4$-alkyl;

$R^5$, $R^6$ are hydrogen, halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, di($C_1$–$C_4$alkyl)aminoimino-$C_1$–$C_4$-alkyl, hydroxyimino-$C_1$–$C_4$-alkyl, $C_1$–$C_6$-alkoxyimino-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, where the two last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy;
or
$R^5$ and $R^6$ together form a $C_2$–$C_6$-alkanediyl chain which may be mono- to tetrasubstituted by $C_1$–$C_4$-alkyl and/or may be interrupted by oxygen or an unsubstituted or $C_1$–$C_4$-alkyl-substituted nitrogen;

$R^7$ is halogen, cyano, hydroxyl, $C_1$–$C_6$-alkyl, $C_1$–$C_6$haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, amino, $C_1$–$C_6$alkylamino, di($C_1$–$C_6$-alkyl)amino, di($C_1$–$C_4$- alkoxy)methyl, hydroxyimino-$C_1$–$C_4$-alkyl, $C_1$–$C_6$-alkoxyimino-$C_1$–$C_4$-alkyl or $COR^8$;

$R^8$ is hydrogen, $C_1$–$C_4$-alkyl, $C_1$–$C_4$-haloalkyl, hydroxyl, $C_1$–$C_4$-alkoxy, $C_1$–$C_4$-alkoxy-$C_2$–$C_4$-alkoxy, $C_1$–$C_4$-haloalkoxy, $C_3$–$C_6$-alkenyloxy, $C_3$–$C_6$-alkynyloxy or $NR^9R^{10}$;

$R^9$ is hydrogen or $C_1$–$C^4$-alkyl;

$R^{10}$ is $C_1$–$C_4$-alkyl;

$R^{11}$ is a pyrazole, attached in the 4-position, of the formula II

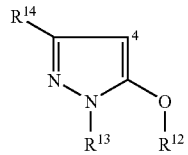

II where $H^{12}$ is hydrogen, $C_1$–$C_4$-alkyl, $C_1$–$C_4$-haloalkyl, $C_3$–$C_4$-alkenyl, $C_3$–$C_4$-alkynyl, $C_1$–$C_4$-alkylcarbonyl, $C_1$–$C_4$-haloalkylcarbonyl, $C_1$–$C_4$-alkylsulfonyl, $C_1$–$C_4$-haloalkylsulfonyl, thienylmethyl, phenyl, benzyl, phenylcarbonyl, phenylsulfonyl or phenylcarbonylmethyl, where the phenyl radical of the five last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_1$–$C_6$-alkyl, $C_1$–$C_6$-haloalkyl or $C_3$–$C_6$-cycloalkyl;

$R^{14}$ is hydrogen, $C_1$–$C_6$-alkyl or $C_3$–$C_6$-cycloalkyl;

and its agriculturally useful salts.

2. A 3-(4,5-dihydroisoxazol-5-yl)benzoylpyrazole of the formula I as claimed in claim 1 where $R^3$ is hydrogen.

3. A 3-(4,5-dihydroisoxazol-5-yl)benzoylpyrazole of the formula I as claimed in claim 1 where $R^1$, $R^2$ are nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl.

4. A 3-(4,5-dihydroisoxazol-5-yl)benzoylpyrazole of the formula I as claimed in claim 1 where $R^{12}$ is $C_1$–$C_4$-alkylsulfonyl, $C_1$–$C_4$-halosulfonyl or phenylsulfonyl, where the phenyl radical may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy.

5. A 3-(4,5-dihydroisoxazol-5-yl)benzoylpyrazole of the formula I as claimed in claim 1 where $R^{12}$ is benzyl, where the phenyl radical may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy.

6. A 3-(4,5-dihydroisoxazol-5-yl)benzoylpyrazole of the formula I as claimed in claim 1 where $R^{12}$ is hydrogen.

7. A 3-(4,5-dihydroisoxazol-5-yl)benzoylpyrazole of the formula I as claimed in claim 1 where $R^5$ is hydrogen, halogen, cyano, nitro, $C_1$–$C_4$-alkyl, $C_1$–$C_4$-alkoxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, where the two last mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$haloalkoxy;

$R^6$ is hydrogen or $C_1$–$C_4$-alkyl.

8. A 3-(4,5-dihydroisoxazol-5-yl)benzoylpyrazole of the formula I as claimed in claim 1 where $R^5$ and $R^6$ are hydrogen.

9. A process for preparing 3-(4,5-dihydroisoxazol-5-yl) benzoylpyrazoles of the formula I as claimed in claim 1, which comprises acylating the pyrazole of the formula II where $R^{12}$=H and where the variables $R^{13}$ and $R^{14}$ are as defined under claim 1

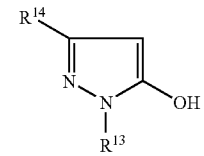

with an activated carboxylic acid IIIa or with a carboxylic acid IIIb,

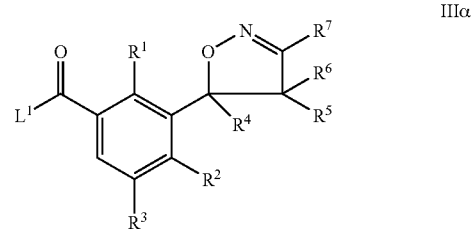

IIIα

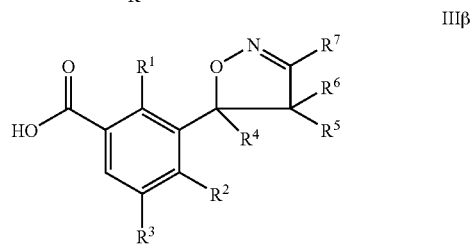

IIIβ where, the variables $R^1$ to $R^7$ are as defined under claim 1 and $L^1$ is a nucleophilically displaceable leaving group and rearranging the acylation product, if appropriate in the presence of a catalyst, to the compounds I (where $R^{12}$=H), followed, if desired, by reaction with a compound of the formula V $L^2$-$R^{12}$ where $R^{12}$ is as defined under claim 1 except for hydrogen and $L^2$ is a nucleophilically displaceable leaving group, to prepare 3-(4,5-dihydroisoxazol-5-yl)benzoylpyrazoles of the formula I where $R^{12}$≠hydrogen.

10. A composition comprising a herbicidally effective amount of at least one 3-(4,5-dihydroisoxazol-5-yl)benzoylpyrazole of the formula I or an agriculturally useful salt of I as claimed in claim 1 and auxiliaries which are customary for formulating crop protection agents.

11. A process for preparing compositions as claimed in claim 10 which comprises mixing a herbicidally effective amount of at least one 3-(4,5-dihydroisoxazol-5-yl)-benzoylpyrazole of the formula I or an agriculturally useful salt of I and auxiliaries which are customary for formulating crop protection agents.

12. A method for controlling undesirable vegetation, wherein a herbicidally effective amount of at least one 3-(4,5-dihydroisoxazol-5-yl)benzoylpyrazoles of the formula I or an agriculturally useful salts as claimed in claim 1 is allowed to act on plants, their habitat and/or seeds.

* * * * *